US008815880B2

(12) United States Patent
Matuura et al.

(10) Patent No.: US 8,815,880 B2
(45) Date of Patent: *Aug. 26, 2014

(54) CRYSTAL OF TRICYCLIC PYRAZOLOPYRIMIDINE DERIVATIVE

(71) Applicant: Daiichi Sankyo Company, Limited, Tokyo (JP)

(72) Inventors: Shinji Matuura, Kanagawa (JP); Hisaki Kajino, Kanagawa (JP); Tomoyuki Nagai, Kanagawa (JP); Keijiro Kobayashi, Kanagawa (JP)

(73) Assignee: Daiichi Sankyo Company, Limited, Chuo-ku (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/773,387

(22) Filed: Feb. 21, 2013

(65) Prior Publication Data

US 2013/0203989 A1 Aug. 8, 2013

Related U.S. Application Data

(63) Continuation of application No. PCT/JP2011/068890, filed on Aug. 22, 2011.

(30) Foreign Application Priority Data

Aug. 23, 2010 (JP) ................................. 2010-186514

(51) Int. Cl.
*A61K 31/55* (2006.01)
*C07D 417/06* (2006.01)
*C07D 495/16* (2006.01)

(52) U.S. Cl.
CPC ............... *C07D 495/16* (2013.01); *A61K 31/55* (2013.01); *C07D 417/06* (2013.01)
USPC .......................................... 514/267; 544/251

(58) Field of Classification Search
CPC .............................. C07D 417/06; A61K 31/55
USPC ........................................... 514/267; 544/251
See application file for complete search history.

(56) References Cited

U.S. PATENT DOCUMENTS 8,158,638 B2 4/2012 Ohsuki
8,236,813 B2 * 8/2012 Ohki et al. .................... 514/267

FOREIGN PATENT DOCUMENTS

| WO | 98/43991 A1 | 10/1998 | | |
|---|---|---|---|---|
| WO | 2004/047755 A2 | 6/2004 | | |
| WO | 2005/021568 A2 | 3/2005 | | |
| WO | 2005/028434 A2 | 3/2005 | | |
| WO | 2006/015263 A2 | 2/2006 | | |
| WO | 2008/035629 A1 | 3/2008 | | |
| WO | 2008/049105 A2 | 4/2008 | | |
| WO | 2008/093075 A2 | 8/2008 | | |
| WO | 2008/100447 A2 | 8/2008 | | |
| WO | 2010/098344 A1 | 9/2010 | | |
| WO | WO 2010/098344 | * | 9/2010 | ........... C07D 495/16 |

OTHER PUBLICATIONS

Blagg, B.S.J., and T.D. Kerr, "Hsp90 Inhibitors: Small Molecules That Transform the Hsp90 Protein Folding Machinery Into a Catalyst for Protein Degradation," Medical Research Reviews 26(3):310-338, May 2006.
Calderwood, S.K., et al., "Heat Shock Proteins in Cancer: Chaperones of Tumorigenesis," Trends in Biochemical Sciences 31(3):164-172, Mar. 2006.
Dymock, B.W., et al., "Novel, Potent Small-Molecule Inhibitors of the Molecular Chaperone Hsp90 Discovered Through Structure-Based Design," Journal of Medicinal Chemistry 48(13):4212-4215, Jun. 2005.
Hammond, D.M., et al., "The Syntheses of Tricyclic Analogues of O$^6$-Methylguanine," Organic & Biomolecular Chemistry 1(23):4166-4172, Dec. 2003.
He, H., et al., "Identification of Potent Water Soluble Purine-Scaffold Inhibitors of the Heat Shock Protein 90," Journal of Medicinal Chemistry 49(1):381-390, Jan. 2006.
Hornillo-Araujo, A.R., et al., "The Syntheses and Properties of Tricyclic Pyrrolo[2,3-d]pyrimidine Analogues of S$^6$-Methylthioguanine and O$^6$-Methylguanine," Organic & Biomolecular Chemistry 4(9):1723-1729, May 2006.
International Preliminary Report on Patentability and Written Opinion mailed Sep. 13, 2011, issued in corresponding International Application No. PCT/JP2011/068890, filed Aug. 22, 2011, 6 pages.
Kamal, A., et al., "Therapeutic and Diagnostic Implications of Hsp90 Activation," Trends in Molecular Medicine, 10(8):283-290, Jun. 2004.
Sõti, C. et al., "Heat Shock Proteins as Emerging Therapeutic Targets," British Journal of Pharmacology 146(6):769-780, Nov. 2005.

* cited by examiner

*Primary Examiner* — Erich A Leeser
(74) *Attorney, Agent, or Firm* — Christensen O'Connor Johnson Kindness PLLC

(57) ABSTRACT

To provide a hydrochloride of a tricyclic pyrazolopyrimidine compound inhibiting the effect of HSP90 and a crystal thereof. The present invention provides a hydrochloride of 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide which inhibits the ATPase activity of HSP90 and which has antitumor activity, a crystal thereof, a medicament comprising the same, an anticancer agent comprising the same, and the like.

17 Claims, 20 Drawing Sheets

CRYSTAL OF TRICYCLIC PYRAZOLOPYRIMIDINE DERIVATIVE

TECHNICAL FIELD

The present invention relates to a hydrochloride of a compound having a tricyclic pyrazolopyrimidine skeleton which inhibits the effect of heat shock protein 90 (HSP90).

BACKGROUND ART

HSP90 is a major intracellular chaperone protein. Chaperone proteins are proteins that bind to various proteins to assist in folding of the bound proteins. A group of proteins whose folding requires HSP90 are generally called HSP90 client proteins.

It is assumed that HSP90 as well as multiple proteins such as cochaperones, partner proteins and immunophilins are involved in the mechanism of folding of client proteins by HSP90 and that they collaboratively assist in folding of HSP90 client proteins (Non Patent Document 1); however, the details of the mechanism are still not sufficiently clear.

It is assumed that HSP90 client proteins form a complex with HSP90, cochaperones and the like and are then conformationally changed to mature proteins and that the proteins are ubiquitinated and degraded by proteasomes when they are not folded normally by HSP90 and the like (Non Patent Documents 1 to 4).

In recent years, HSP90 inhibitors have been expected as candidates for therapeutic agents for various diseases (for example, cancer, neurodegenerative diseases such as Alzheimer's disease, cardiovascular diseases, infections, autoimmune diseases, and diseases associated with apoptotic cell injury) (Non Patent Document 2).

In particular, since many cancer-associated proteins including molecular targets for anticancer agents are HSP90 client proteins, HSP90 inhibitors have been expected as candidates for anticancer agents. For example, multiple proteins involved in the occurrence and development of cancer such as Her2, Raf, Akt and telomerase are known as HSP90 client proteins (Non Patent Document 1). It is assumed that these cancer-associated proteins are changed from immature proteins to mature proteins and act to cause malignant transformation of cells, respectively, by use of HSP90 as a chaperone protein. HSP90 is a protein that exists not only in cancer cells but also in normal cells, and it is reported that the affinity with a client protein and the ATPase activity necessary for its chaperone activity are higher in cancer cells than in normal cells (Non Patent Documents 1 to 3). Therefore, HSP90 inhibitors are assumed to be capable of inactivating multiple cancer-associated proteins simultaneously in a cancer cell-specific manner, and have been expected as candidates for anticancer agents that are potent and have a broad antitumor spectrum.

Geldanamycin, herbimycin, 17-allylaminogeldanamycin (17-AAG) and the like are conventionally known as HSP90 inhibitors (Non Patent Documents 1 to 4). These compounds bind to the ATP binding pocket at the N-terminal of HSP90 and inhibit binding of HSP90 to ATP in order to inhibit the function of HSP90 as a chaperone protein. Various compounds inhibiting HSP90 are reported in addition to the above compounds (Patent Document 1, Patent Document 2, Patent Document 3, Non Patent Document 5 and Non Patent Document 6) and a tricyclic pyrazolopyrimidine derivative is also reported (Patent Document 4).

Moreover, several publications have reported the intended uses of tricyclic pyrazolopyrimidine derivatives and compounds having a condensed ring structure, which also have three constituent heterocyclic rings, for anticancer purposes (Patent Documents 5 to 9, and Non Patent Documents 7 and 8).

CITATION LIST

Patent Documents

Patent Document 1: WO 2005/28434
Patent Document 2: WO 2008/049105
Patent Document 3: WO 2008/093075
Patent Document 4: WO 2008/035629
Patent Document 5: WO 2004/047755
Patent Document 6: WO 2006/015263
Patent Document 7: WO 2005/021568
Patent Document 8: WO 1998/043991
Patent Document 9: WO 2008/100447

Non Patent Documents

Non Patent Document 1: Medicinal Research Reviews (2006) Vol. 26, No. 3, 310-338
Non Patent Document 2: TRENDS in Molecular Medicine (2004) Vol. 10, No. 6, 283-290
Non Patent Document 3: British Journal of Pharmacology (2005) 146, 769-780
Non Patent Document 4: TRENDS in Biochemical Sciences (2006) Mar. 31 (3), 164-172
Non Patent Document 5: Journal of Medicinal Chemistry (2005) Vol. 48, No. 13, 4212-4215
Non Patent Document 6: Journal of Medicinal Chemistry (2006) Vol. 49, No. 1, 381-390
Non Patent Document 7: Organic & Biomolecular Chemistry (2003) Vol. 1, No. 23, 4166-4172
Non Patent Document 8: Organic & Biomolecular Chemistry (2006) Vol. 4, No. 9, 1723-1729

SUMMARY OF INVENTION

Problem to be Solved by the Invention

A tricyclic pyrazolopyrimidine derivative exhibits excellent HSP90 inhibitory activity and is expected to be used as a medicament, and in particular, as an anticancer agent. Moreover, if its effectiveness can be improved by improving the physical properties of such a derivative, such as solubility, so as to enhance its absorbency, or if its side effects can be reduced by decreasing the dosage thereof, the usefulness of the derivative for medical purpose can be further improved.

Furthermore, a substance used in medicaments is required to have a particularly high purity, so as not to have unexpected side effects (e.g. toxicity) caused by its impurities. In addition, it is important for drug substances of medicaments to be stored for a long period of time, while their quality is maintained. Thus, it is industrially significant to find a highly stable crystal that can be stored for a long period of time.

Means for Solving the Problem

In order to enhance the usefulness of a tricyclic pyrazolopyrimidine derivative as a novel compound, which inhibits the ATPase activity of HSP90 and which has antitumor activity, for medical purpose, the present inventors have conducted extensive studies including the production of the salts of the derivative, etc., for the improvement of its solubility, purity, stability, and the like. As a result, the inventors have found a dihydrochloride and a monohydrochloride of the tricyclic pyrazolopyrimidine derivative, which are superior to the pyrazolopyrimidine derivative itself (a free form) in terms of solubility, and also a monohydrochloride of the tricyclic pyrazolopyrimidine derivative, which is superior to the tricyclic pyrazolopyrimidine derivative itself in terms of solubility and which has a small content of impurity, a small content of residual solvent as well as excellent stability. Still further, the present inventors have established a method for reliably producing such individual salts, thereby completing the present invention.

More specifically, the present invention relates to the following [1] to [18]:

[1] A hydrochloride of 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide represented by the following formula (1):

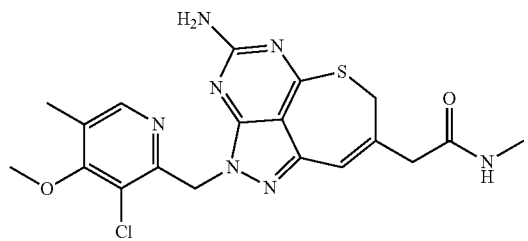

[2] A crystal of a dihydrochloride of 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide represented by the formula (1) according to [1].

[3] The crystal according to [2] which has the X-ray diffraction pattern shown in FIG. 1, in an X-ray powder diffraction pattern obtained by irradiation with a copper Kα radiation (wavelength λ=1.54 angstroms).

[4] The crystal according to [2] which shows characteristic peaks at angles of diffraction 2θ of 7.73, 24.70, 26.01 and 27.29, in an X-ray powder diffraction pattern obtained by irradiation with a copper Kα radiation (wavelength λ=1.54 angstroms).

[5] The crystal according to [2] or [4] which shows principal peaks at angles of diffraction 2θ of 7.73, 9.78, 12.58, 14.36, 15.84, 16.71, 17.17, 18.40, 19.58, 21.31, 22.85, 23.62, 24.13, 24.70, 26.01, 27.29, 28.58, 29.37, 30.65, 31.38, 33.52, 35.25 and 36.87, in an X-ray powder diffraction pattern obtained by irradiation with a copper Kα radiation (wavelength λ=1.54 angstroms).

[6] A crystal of a monohydrochloride of 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide represented by the formula (1) according to [1].

[7] The crystal according to [6] which has the X-ray diffraction pattern shown in FIG. 2, in an X-ray powder diffraction pattern obtained by irradiation with a copper Kα radiation (wavelength λ=1.54 angstroms).

[8] The crystal according to [6] which shows principal peaks at angles of diffraction 2θ of 9.43, 12.70, 13.03, 15.33, 16.10, 16.84, 18.55, 20.21, 20,89, 21.32, 22.93, 24.73, 25.10, 25.40, 26.10, 26.53, 26.95, 27.60, 27.88, 28.52, 29.63, 29.95, 31.55, 32.13, 33.40, 34.95 and 38.70, in an X-ray powder diffraction pattern obtained by irradiation with a copper Kα radiation (wavelength λ=1.54 angstroms).

[9] The crystal according to [6] which has the X-ray diffraction pattern shown in FIG. 3, in an X-ray powder diffraction pattern obtained by irradiation with a copper Kα radiation (wavelength λ=1.54 angstroms).

[10] The crystal according to [6] which shows principal peaks at angles of diffraction 2θ of 8.07, 9.45, 13.07, 15.39, 16.16, 16.90, 20.83, 24.29, 24.80, 28.56, 28.85, 31.26, 32.17, 32.87 and 34.11, in an X-ray powder diffraction pattern obtained by irradiation with a copper Kα radiation (wavelength λ=1.54 angstroms).

[11] A crystal of the hydrochloride of 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide represented by the formula (1) according to [1], wherein the content of ethanol is 5000 ppm or less.

[12] The crystal according to [11], wherein the hydrochloride is a monohydrochloride.

[13] A method for producing the hydrochloride according to [1] which comprises adding a hydrogen chloride solution dropwise to a solution or suspension of 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide represented by the formula (1) according to [1].

[14] A method for producing the crystal of the dihydrochloride according to [2] which comprises adding a hydrogen chloride solution dropwise to a solution or suspension of 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide represented by the formula (1) according to claim 1 in an amount of 2 equivalents or more relative to the above-mentioned compound.

[15] A method for producing the crystal of the monohydrochloride according to [6] which comprises adding a hydrogen chloride solution dropwise to a solution or suspension of 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide represented by the formula (1) according to claim 1 in an amount of 1 equivalent or more and 5 equivalents or less relative to the above-mentioned compound.

[16] A medicament comprising a hydrochloride according to [1] as an active ingredient.

[17] An antitumor agent comprising a hydrochloride according to [1].

[18] A pharmaceutical composition comprising a crystal according to any one of [2] to [12].

Advantages of the Invention

According to the present invention, there is provided a dihydrochloride and a monohydrochloride of 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide having HSP90 inhibitory activity, which have more excellent solubility. There is also provided a monohydrochloride, which has a small content of impurity, a small amount of residual solvent, as well as excellent stability. The compound of the present invention is useful as an anticancer agent.

DESCRIPTION OF EMBODIMENTS

The present invention relates to a hydrochloride of 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide (hereinafter also referred to as "compound (1)") represented by formula (1) shown below, and a crystal of the hydrochloride:

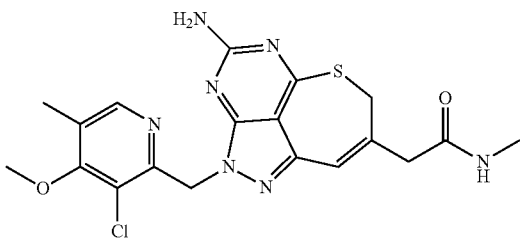

(1)

Herein, the term "crystal" means a solid whose internal structure is made of three-dimensionally regular repeats of constituent atoms (or a group thereof). Thus, the crystal can be distinguished from an amorphous solid that does not have such a regular internal structure.

Even from a single compound, there may be a case in which a plurality of crystals (crystalline polymorphism) having different internal structures and different physicochemical properties are generated, depending on conditions for crystallization. The crystal of the present invention may be any one of these polymorphic forms, and may also be a mixture of two or more polymorphic forms.

Moreover, the crystal of the invention of the present application, which is shown below as a preferred crystalline form, may only consist of the crystalline form, may be contained in a mixture with other crystals, or may be contained in a mixture with an amorphous substance. Hence, existence situation of the crystal of the present invention is not particularly limited.

The crystal of the present invention may absorb moisture by being left in the air, and as a result, water may adhere to the surface thereof, or the crystal of the present invention may form a hydrate by being heated to a temperature of 25° C. to 150° C. under ordinary atmospheric conditions. Furthermore, in the case of the crystal of the present invention, a solvent used in crystallization may be contained in a residual solvent or a solvate.

In the present specification, the crystal of the present invention is indicated based on the data of X-ray powder diffraction. The measurement and/or analysis of such X-ray powder diffraction may be carried out by means commonly used in the present technical field. For example, the X-ray powder diffraction may be carried out by the methods described in Examples. In general, the lattice constant of a hydrate or a dehydration product changes due to the attachment or removal of crystal water, and as a result, it may change an angle of diffraction (2θ) in the X-ray powder diffraction. In addition, the peak intensity may change depending on a difference in the growth face of crystal (crystal habit), etc. Accordingly, when the crystal of the present invention is indicated based on the data of X-ray powder diffraction, not only crystals having the same peak angle of diffraction and the same X-ray diffraction pattern in the X-ray powder diffraction, but also hydrates and dehydration products obtained from the aforementioned crystals, are included in the scope of the present invention.

Figure 1:
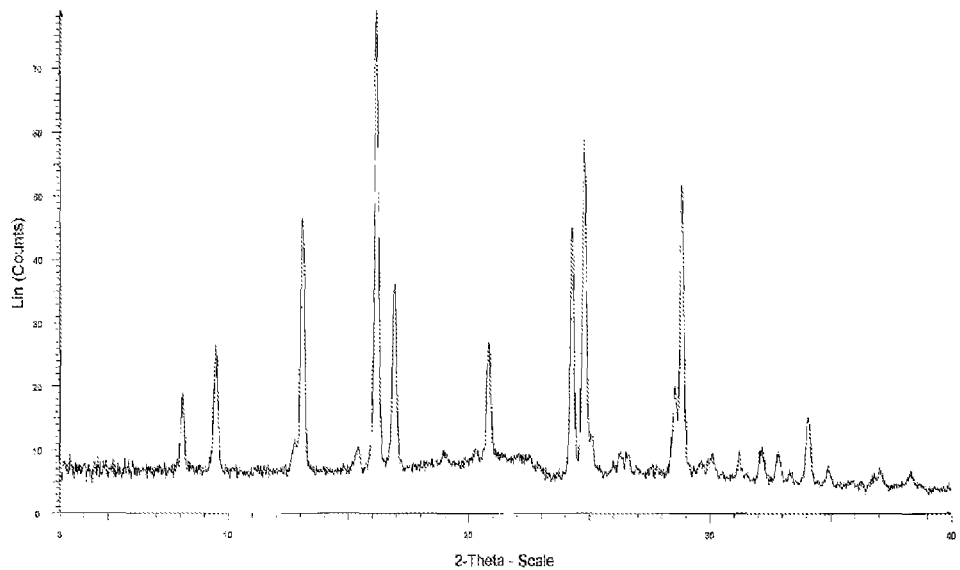
FIG. 1 shows an X-ray powder diffraction pattern of the crystal obtained in Example 2. The longitudinal axis of the pattern (numerical values added to the scale are 0, 10, 20, 30 and 40 from the bottom) shows diffraction intensity (Lin (Counts)), and the horizontal axis (numerical values added to the scale are 3, 10, 20, 30 and 40 from the left) shows the value of angle of diffraction 2θ.

One preferred form of the crystal of the present invention is a crystal of the dihydrochloride of the compound (1). The crystal of the dihydrochloride of the compound (1) has the X-ray diffraction pattern shown in FIG. 1, in an X-ray powder diffraction pattern obtained by irradiation with a copper Kα radiation (wavelength λ=1.54 angstroms). In addition, the crystal of the dihydrochloride of the compound (1) has characteristic peaks at angles of diffraction 2θ of 7.73, 24.70, 26.01 and 27.29 in the X-ray powder diffraction pattern obtained by irradiation with a copper Kα radiation (wavelength λ=1.54 angstroms). The term "characteristic peak" is used herein to mean a peak with a relative intensity of 50 or greater, when the maximum peak intensity is set at 100 in the X-ray powder diffraction pattern. Moreover, the crystal of the dihydrochloride of the compound (1) of the present invention is also a crystal that shows principal peaks at angles of diffraction 2θ of 7.73, 9.78, 12.58, 14.36, 15.84, 16.71, 17.17, 18.40, 19.58, 21.31, 22.85, 23.62, 24.13, 24.70, 26.01, 27.29, 28.58, 29.37, 30.65, 31.38, 33.52, 35.25 and 36.87 in the X-ray powder diffraction pattern obtained by irradiation with a copper Kα radiation (wavelength λ=1.54 angstroms). The term "principal peak" is used herein to mean a peak with a relative intensity of 15 or greater, when the maximum peak intensity is set at 100 in the X-ray powder diffraction pattern.

Another preferred form of the crystal of the present invention is a crystal of the monohydrochloride of the compound (1). One form of the crystal of the monohydrochloride of the compound (1) is a crystal having the X-ray diffraction pattern shown in FIG. 2, in an X-ray powder diffraction pattern obtained by irradiation with a copper Kα radiation (wavelength λ=1.54 angstroms). In addition, the crystal in the present form is also a crystal that shows principal peaks at angles of diffraction 2θ of 9.43, 12.70, 13.03, 15.33, 16.10, 16.84, 18.55, 20.21, 20.89, 21.32, 22.93, 24.73, 25.10, 25.40, 26.10, 26.53, 26.95, 27.60, 27.88, 28.52, 29.63, 29.95, 31.55, 32.13, 33.40, 34.95 and 38.70 in the X-ray powder diffraction pattern obtained by irradiation with a copper Kα radiation (wavelength λ=1.54 angstroms). The term "principal peak" is used herein to mean a peak with a relative intensity of 30 or greater, when the maximum peak intensity is set at 100 in the X-ray powder diffraction pattern.

Figure 3:
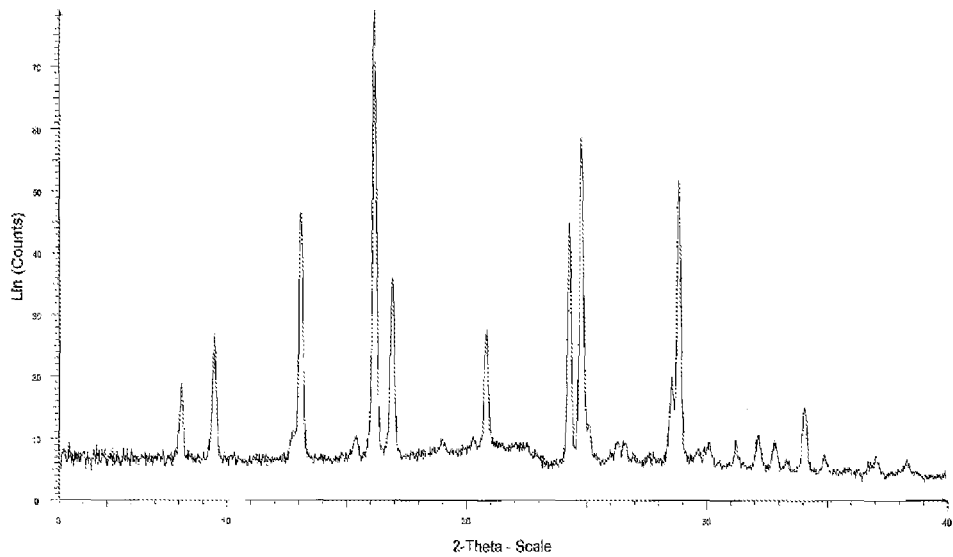
FIG. 3 shows an X-ray powder diffraction pattern of the crystal obtained in Example 6. The longitudinal axis of the pattern (numerical values added to the scale are 0, 10, 20, 30, 40, 50, 60 and 70 from the bottom) shows diffraction intensity (Lin (Counts)), and the horizontal axis (numerical values added to the scale are 3, 10, 20, 30 and 40 from the left) shows the value of angle of diffraction 2θ.

Another form of the crystal of the monohydrochloride of the compound (1) of the present invention is a crystal having the X-ray powder diffraction pattern shown in FIG. 3, in an X-ray powder diffraction pattern obtained by irradiation with a copper Kα radiation (wavelength λ=1.54 angstroms). In addition, the crystal in the present form is also a crystal that shows principal peaks at angles of diffraction 2θ of 8.07, 9.45, 13.07, 15.39, 16.16, 16.90, 20.83, 24.29, 24.80, 28.56, 28.85, 31.26, 32.17, 32.87 and 34.11 in the X-ray powder diffraction pattern obtained by irradiation with a copper Kα radiation (wavelength λ=1.54 angstroms). The term "principal peak" is used herein to mean a peak with a relative intensity of 12 or greater, when the maximum peak intensity is set at 100 in the X-ray powder diffraction pattern.

Conversion of 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide to a hydrochloride is generally carried out by adding a hydrogen chloride solution dropwise to a solution or suspension of 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide.

A solvent used is not particularly limited, as long as 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide and hydrogen chloride are dissolved in the solvent to a certain extent, and conversion of 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide to a hydrochloride is not inhibited by the solvent. Examples of such a solvent include: hydrocarbons such as pentane, hexane, heptane, octane, isooctane, cyclohexane, methylcyclohexane, benzene, toluene and xylene; halogenated hydrocarbons such as dichloromethane, chloroform, 1,2-dichloroethane and chlorobenzene; ethers such as diethyl ether, diisopropyl ether, dibutyl ether, tetrahydrofuran, 2-methyl tetrahydrofuran, dioxane and methyl cyclopentyl ether; esters such as methyl acetate, ethyl acetate, propyl acetate, butyl acetate, methyl propionate and ethyl propionate; ketones such as acetone, methyl ethyl ketone, cyclopentanone and cyclohexanone; nitriles such as acetonitrile and propionitrile; amides such as N,N-dimethylformamide, N,N-dimethylacetamide, N,N'-dimethylimidazolidinone and hexamethylphosphoric triamide; sulfoxides such as dimethyl sulfoxide; alcohols such as methanol, ethanol, propanol, isopropyl alcohol, butanol and isobutyl alcohol; water; and a mixture thereof. Preferred examples of the solvent include ketones, alcohols, water, and a mixture thereof. More preferred examples include alcohols, water, and a mixture thereof. Further preferred examples include methanol, ethanol, water, and a mixture thereof.

The solvent used in the preparation of a solution or suspension of 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide may be identical to or different from the solvent used in the preparation of a hydrogen chloride solution.

The concentration of the hydrogen chloride solution used is not particularly limited. It is generally a 0.1 mol/L to saturated solution, and preferably a 0.5 mol/L to saturated solution.

The temperature applied during conversion of the above-mentioned compound to a hydrochloride is not particularly limited, unless the solvent used is solidified at the temperature. It is generally between −70° C. and 70° C., and preferably between −20° C. and 50° C.

When a dihydrochloride is produced, the amount of the hydrogen chloride used is not particularly limited, as long as it is an amount necessary for conversion of 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide to a dihydrochloride. It is generally 2 equivalents or more and 100 equivalents or less, preferably 2 equivalents or more and 20 equivalents or less, and more preferably 2 equivalents or more and 10 equivalents or less.

When a monohydrochloride is produced, the amount of the hydrogen chloride used is not particularly limited, as long as it is an amount, which is necessary for conversion of 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide to a monohydrochloride and in which a dihydrochloride is not precipitated. Such an amount depends on the type of a solvent used, the amount of a solvent used, and the temperature. It is generally 1 equivalent or more and 10 equivalents or less, preferably 1 equivalent or more and 5 equivalents or less, and more preferably 1 equivalent or more and 3 equivalents or less.

When a dihydrochloride is produced, a seed crystal may be added. When such a seed crystal is added, the timing at which it is added is not particularly limited. In general, such a seed crystal is added in the range of the hydrogen chloride concentration, at which the dihydrochloride becomes supersaturated. The hydrogen chloride concentration is different depending on the composition of a solvent. In general, hydrogen chloride needs to be added in an amount of approximately 2 equivalents or more. The amount of a seed crystal used is not limited. It is generally 0.0000001 equivalent or more and 1 equivalent or less, preferably 0.000001 equivalent or more and 0.5 equivalent or less, and more preferably 0.00001 equivalent or more and 0.1 equivalent or less.

When a monohydrochloride is produced, a seed crystal of a monohydrochloride to be obtained may be added. When such a seed crystal is added, the timing at which it is added is not particularly limited. In general, such a seed crystal is added in the range of the hydrogen chloride concentration, at which the monohydrochloride becomes supersaturated. The hydrogen chloride concentration is different depending on the composition of a solvent. In general, hydrogen chloride needs to be added in an amount of approximately 1 equivalent or more. The amount of a seed crystal used is not limited. It is generally 0.0000001 equivalent or more and 1 equivalent or less, preferably 0.000001 equivalent or more and 0.5 equivalent or less, and more preferably 0.00001 equivalent or more and 0.1 equivalent or less.

Figure 2:
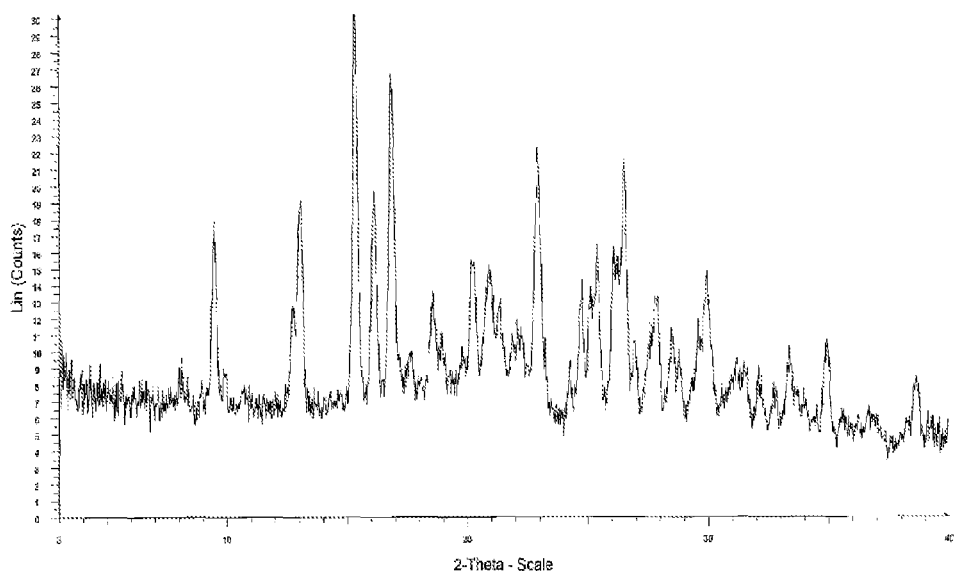
FIG. 2 shows an X-ray powder diffraction pattern of the crystal obtained in Example 3. The longitudinal axis of the pattern (numerical values added to the scale are 0, 1, 2, 3, 4, 5, 6, 7, 8, 9, 10, 11, 12, 13, 14, 15, 16, 17, 18, 19, 20, 21, 22, 23, 24, 25, 26, 27, 28, 29 and 30 from the bottom) shows diffraction intensity (Lin (Counts)), and the horizontal axis (numerical values added to the scale are 3, 10, 20, 30 and 40 from the left) shows the value of angle of diffraction 2θ.

With regard to crystals of monohydrochlorides, a crystal having the X-ray powder diffraction pattern shown in FIG. 2 and a crystal having the X-ray powder diffraction pattern shown in FIG. 3 can be produced by the methods described in Examples 3 to 5 as described below and by the methods described in Examples 6 to 33 as described below, respectively. However, production methods are not limited thereto. When the crystal having the X-ray powder diffraction pattern shown in FIG. 3 is produced, it is desired to increase the hydrogen chloride concentration in a stepwise manner, for example, by dividing the hydrogen chloride to be added into two to about ten small amounts, around the hydrogen chloride concentration at which the hydrochloride becomes supersaturated in the reaction solution. The crystal having the X-ray powder diffraction pattern shown in FIG. 3 had excellent stability, and also had a small amount of a residual solvent in the crystal, for example, a small amount of residual ethanol in the crystal. The amount of a residual solvent in the crystal is preferably 6000 ppm or less, and more preferably 5000 ppm or less.

Other embodiments of the present invention are a medicament comprising the hydrochloride or the crystal of the present invention as an active ingredient, and an antitumor agent comprising the hydrochloride or the crystal of the present invention. Another embodiment of the present invention also relates to a pharmaceutical composition comprising the hydrochloride or the crystal of the present invention.

The medicament comprising the hydrochloride or the crystal of the present invention as an active ingredient is preferably provided in the form of a pharmaceutical composition comprising the crystal of the present invention and one or two or more of pharmacologically acceptable carriers. The dosage form of the medicament of the present invention is not particularly limited, and the present medicament can be administered orally or parenterally. It is preferably administered orally.

The pharmaceutical composition of the present invention comprises at least a portion of the hydrochloride or the crystal of the present invention as a compound (I). The present pharmaceutical composition may also include a crystalline form other than the crystal of the invention of the present application as a compound (I). The ratio of the crystal of the invention of the present application in the present pharmaceutical composition may be in the range from 0.01% by weight to 99.9% by weight, for example, 0.01% by weight or more, 0.05% by weight or more, 0.1% by weight or more, 0.5% by weight or more, 1% by weight or more, 2% by weight or more, 3% by weight or more, 4% by weight or more, 5% by weight or more, 10% by weight or more, 20% by weight or more, 30% by weight or more, 40% by weight or more, 50% by weight or more, 60% by weight or more, 70% by weight or more, 80% by weight or more, 90% by weight or more, 95% by weight or more, 96% by weight or more, 97% by weight or more, 98% by weight or more, 99% by weight or more, 99.5% by weight or more, 99.6% by weight or more, 99.7% by weight or more, 99.8% by weight or more, or 99.9% by weight or more, based on the total weight of the compound (I) in the present pharmaceutical composition. The presence or absence of the crystal of the invention of the present application in the pharmaceutical composition can be confirmed by instrumental analysis methods described in the present specification (e.g. X-ray powder diffraction, thermal analysis, infrared absorption spectrum, etc.).

Since the hydrochloride or the crystal of the present invention can be used as an HSP90 inhibitor, an agent for inhibiting the ATPase activity of HSP90, or an agent for inhibiting the binding of HSP90 to ATP. Thus, it can be used as a medicament comprising the hydrochloride or the crystal of the present invention, and particularly preferably as an anticancer agent.

The ATPase activity of HSP90 can be examined by an ATPase assay commonly used by a person skilled in the art. For example, the ATPase activity of HSP90 can be detected using a recombinant HSP90 protein and ATP in the presence or absence of the test compound. Alternatively, in an ATPase assay, the method described in Analytical Biochemistry 327, 176-183 (2004) or Nature 425, 407-410 (2003) may be suitably performed, for example.

Inhibition of the expression of HSP90 can be examined by Northern blotting, Western blotting, ELISA or the like commonly used by a person skilled in the art. For example, mRNA is recovered from cells cultured in the presence or absence of the test compound to perform Northern blotting. When the amount of HSP90 mRNA in mRNA recovered from the cells cultured in the presence of the test compound is reduced from that in mRNA recovered from the cells cultured in the absence of the test compound, the test compound is identified as a compound inhibiting the expression of HSP90. Alternatively, the amount of HSP90 protein may be suitably examined by performing Western blotting using the method described in Cancer. Res. 65, 6401-6408 (2005), for example.

Inhibition of binding of HSP90 to a client protein can be examined by immunoprecipitation and Western blotting commonly used by a person skilled in the art, for example. In immunoprecipitation and Western blotting, the method described in J. Biol. Chem. 277, 10346-10353 (2002) may be suitably performed, for example.

The compound inhibiting binding of HSP90 to co-chaperones or immunophilins can be examined by immunoprecipitation and Western blotting commonly used by a person skilled in the art, for example. Binding of HSP90 to co-chaperones or immunophilins may be suitably examined in the presence or absence of the test compound by performing the method described in Nature 425, 407-410 (2003), for example.

Inhibition of binding of HSP90 to ATP can be examined by a test for binding of labeled ATP to HSP90, for example. Binding of HSP90 to labeled ATP may be suitably examined in the presence or absence of the test compound by performing the method described in J. Biol. Chem. 272, 18608-18613 (1997), for example.

Inhibition of the conformational change of HSP90 can be examined by a conformational assay using bis-ANS (1,1'-bis (4-anilino-5-naphthalenesulfonic acid)), for example. In the conformational assay, the method described in J. Med. Chem. 47, 3865-3873 (2004) may be suitably performed, for example.

Cell growth inhibitory activity can be examined using a growth inhibition test method that is commonly used by a person skilled in the art. The cell growth inhibition activity can be determined by, for example, comparing the levels of cellular growth (for example, tumor cells) in the presence or absence of a test compound as described in the following Test Example 1. The growth level can be examined using a test system for assaying living cells. Examples of the method for assaying living cells include a [$^3$H]-thymidine uptake test, a BrdU method and an MTT assay.

Moreover, in vivo antitumor activity can be examined using a method for testing antitumor activity commonly used by a person skilled in the art. For example, various types of tumor cells are transplanted into a mouse, a rat or the like, and after the confirmation of the survival of the transplanted cells, the compound of the present invention is administered to the animal via oral administration, intravenous administration, etc. Thereafter, several days to several weeks later, the growth of tumor in an agent non-administration group is compared with that in a compound administration group, so as to confirm the in vivo antitumor activity of the compound of the present invention.

The hydrochloride or the crystal of the present invention can be used for treatment of tumors or cancers, such as lung cancer, gastrointestinal cancer, ovarian cancer, uterine cancer, breast cancer, liver cancer, head and neck cancer, blood cancer, renal cancer, testicular neoplasm, prostate cancer, multiple myeloma, skin cancer such as malignant melanoma, sarcoma, for example.

Since the hydrochloride or the crystal of the present invention has HSP90 inhibitory action, it can be used for treatment of cancer in which HSP90 dependency is increased. Such cancers in which HSP90 dependency is increased include cancer in which an HSP90 client protein(s) is excessively expressed, cancer in which an HSP90 client protein(s) is mutated, and the like. More specific examples include cancer in which Her2, c-Met, Flt3 or the like is excessively expressed, and cancer in which c-kit, PDGFR, Raf or the like is mutated. However, examples are not limited thereto.

Furthermore, many factor groups associated with cancer (RAS-MAPK, PI3K, telomerase, etc.) are present downstream of HSP90. If HSP90 is inhibited, signalling to such factors is also inhibited. As a result, the activation of the aforementioned factors is also inhibited. Thus, from this viewpoint as well, the hydrochloride or the crystal of the present invention that is an HSP90 inhibitor can be preferably used for treatment of various types of cancers.

The pharmaceutical composition of the present invention comprises the hydrochloride or the crystal of the present invention and a pharmacologically acceptable carrier. It can be used as various types of injections such as an intravenous injection, an intramuscular injection or a subcutaneous injection, or it can be administered by various methods such as oral administration or a percutaneous administration. The pharmacologically acceptable carrier refers to a pharmacologically acceptable material (for example, an excipient, a diluent, an additive, a solvent, etc.), which is associated with the transportation of the hydrochloride or the crystal of the present invention or a composition comprising the hydrochloride or the crystal of the present invention from a certain apparatus or organ to another apparatus or organ.

As a method for preparing a formulation, a suitable formulation (for example, an oral formulation or an injection) is selected, and a commonly used method for preparing various types of formulations can be applied depending on the administration method. Examples of oral formulations include tablets, powders, granules, capsules, pills, troches, solutions, syrups, elixirs, emulsions, and oily or aqueous suspensions. In the case of oral administration, the agent may be either a free form or a salt form. The aqueous formulation can be produced by forming an acid adduct with a pharmacologically acceptable acid or forming a salt of an alkali metal such as sodium. When the formulation is an injection, a stabilizer, a preservative, a solubilizer or the like can also be used in the formulation. The injection may be provided as a formulation to be prepared before use by storing a solution which may contain such an adjuvant or the like in a container and then converting it to a solid formulation by lyophilization or the like. One dose may be stored in one container, or multiple doses may be stored in one container.

Examples of solid formulations include tablets, powders, granules, capsules, pills and troches. These solid formulations may contain a pharmaceutically acceptable additive together with the hydrochloride or the crystal of the present invention. Examples of the additive include fillers, bulking agents, binders, disintegrants, solubilizers, wetting agents and lubricants. These can be selectively mixed as necessary to provide a formulation.

Examples of liquid formulations include solutions, syrups, elixirs, emulsions and suspensions. These liquid formulations may contain a pharmaceutically acceptable additive together with the hydrochloride or the crystal of the present invention. Examples of the additive include suspending agents and emulsifiers. These can be selectively mixed as necessary to provide a formulation.

The crystal of the present invention can be used together with other antitumor agents. Examples of such other antitumor agents include an antitumor antibiotic, an antitumor plant ingredient, BRM (biological response modifier), hormone, vitamin, an antitumor antibody, a molecular-targeted agent, and other antitumor agents.

More specifically, examples of an alkylating agent include: alkylating agents such as nitrogen mustard, nitrogen mustard N-oxide, or chlorambucil; aziridine alkylating agents such as carboquone or thiotepa; epoxide alkylating agents such as dibromomannitol or dibromodulcitol; nitrosourea alkylating agents such as carmustine, lomustine, semustine, nimustine hydrochloride, streptozocin, chlorozotocin, or ranimustine; busulphan; improsulfan tosilate; and Dacarbazine.

Examples of various types of antimetabolites include: purine antimetabolites such as 6-mercaptopurine, 6-thioguanine, or thioinosine; pyrimidine antimetabolites such as fluorouracil, tegafur, tegafur-uracil, carmofur, doxifluridine, broxuridine, cytarabine, or enocitabine; and antifolics such as methotrexate or trimethotrexate.

Examples of an antitumor antibiotic include: anthracycline antibiotic antitumor agents such as mitomycin C, bleomycin, peplomycin, daunorubicin, aclarubicin, doxorubicin, pirarubicin, THP-adriamycin, 4'-epidoxorubicin, or epirubicin; chromomycin A3; and actinomycin D.

Examples of an antitumor plant ingredient include: vinca alkaloids such as vindesine, vincristine, or vinblastine; taxanes such as paclitaxel or docetaxel; and epipodophyllotoxins such as etoposide or teniposide.

Examples of a BRM include a tumor necrosis factor and indomethacin.

Examples of a hormone include hydrocortisone, dexamethasone, methylprednisolone, prednisolone, prasterone, betamethasone, triamcinolone, oxymetholone, nandrolone, methenolone, fosfestrol, ethinyl estradiol, chlormadinone, and medroxyprogesterone.

Examples of a vitamin include vitamin C and vitamin A.

Examples of an antitumor antibody and the molecular-targeted agent include trastuzumab, rituximab, cetuximab, nimotuzumab, denosumab, bevacizumab, infliximab, imatinib mesylate, gefitinib, erlotinib, sunitinib, lapatinib, and sorafenib.

Examples of other antitumor agents include cisplatin, carboplatin, oxaliplatin, tamoxifen, camptothecin, ifosfamide, cyclophosphamide, melphalan, L-asparaginase, aseclatone, schizophyllan, picibanil, procarbazine, pipobroman, neocarzinostatin, hydroxyurea, ubenimex, and krestin.

The present invention includes a method for preventing cancer and/or a method for treating cancer, which comprises the administration of the hydrochloride or the crystal of the present invention.

The dose of the pharmaceutical composition comprising the hydrochloride or the crystal of the present invention as an active ingredient is not particularly limited. It can be selected, as appropriate, depending on various conditions such as the age, body weight, and symptoms of a patient. It is desired that the active ingredient of the pharmaceutical composition is administered to an adult in a daily dose range of 1 mg to 1000 mg, preferably 5 mg to 500 mg, more preferably 5 mg to 300 mg, and further preferably 5 mg to 100 mg, once or divided over several administrations per day, and preferably once or twice per day, depending on symptoms.

2-{4-Amino-2-[(3-chloro-4-methoxy-5-methylpyridin-2-yl)methyl]-2,7-dihydro-6-thia-1,2,3,5-tetraazabenzo[cd] azulen-8-yl}-N-methylacetamide (a free form), which is a raw material for 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide hydrochloride of the present invention, can be produced, for example, in accordance with Reference Example 1 as described below.

The present invention will be described in detail in the following examples.

EXAMPLES

Reference Example 1

Production of 2-{4-amino-2-[(3-chloro-4-methoxy-5-methylpyridin-2-yl)methyl]-2,7-dihydro-6-thia-1, 2,3,5-tetraazabenzo[cd]azulen-8-yl}-N-methylacetamide (free form)

(1) 1-(2-Amino-4,6-dichloropyrimidin-5-yl)-3-buten-1-ol

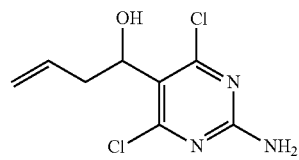

Indium powder (0.23 g) and zinc powder (1.31 g) were added to a mixture composed of commercially available 2-amino-4,6-dichloropyrimidine-5-carboaldehyde (1.92 g) and N,N-dimethylformamide (20 ml). Thereafter, sodium iodide (0.15 g) and allyl bromide (1.73 ml) were added to the mixture at room temperature. The resulting mixture was stirred for 3 hours. Thereafter, the reaction mixture was filtered through celite, and ethyl acetate was then added to the filtrate. The resulting mixture was successively washed with 1 N hydrochloric acid and a saturated saline in this order. The organic layer was dried over anhydrous sodium sulfate, and was then concentrated. Thereafter, hexane was added to the residue, and a precipitate was then collected by filtration, so as to obtain the above title compound (1.75 g) as a solid.

$^1$H-NMR (DMSO-D$_6$) δ: 2.55-2.69 (2H, m), 4.95-5.09 (3H, m), 5.37 (1H, d, J=4.1 Hz), 5.67-5.77 (1H, m), 7.42 (2H, s).

(2) 1-(2-Amino-4,6-dichloropyrimidin-5-yl)-2-(2,2-dimethyl-[1,3]dioxolan-4-yl)ethan-1-ol

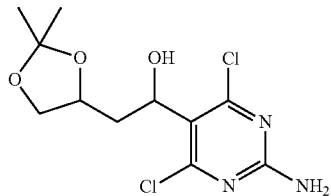 [SMILES: CC1(C)OCC(CC(O)c2c(Cl)nc(N)nc2Cl)O1]

A mixture composed of 1-(2-amino-4,6-dichloropyrimidin-5-yl)-3-buten-1-ol (57.24 g), N-methylmorpholine-N-oxide (147.6 g), tetrahydrofuran (500 ml), acetone (500 ml), water (500 ml) and osmium tetroxide (62 mg) was stirred at room temperature for 2 days. After the disappearance of the materials had been confirmed, a saturated aqueous sodium thiosulfate solution (1 L) was added to the reaction solution, and the reaction mixture was then concentrated to approximately 1.5 L under reduced pressure. The residue was saturated with sodium chloride, followed by extraction with tetrahydrofuran. The organic layer was dried over anhydrous sodium sulfate. After filtration, the filtrate was concentrated under reduced pressure, and the solvent was then distilled away. N,N-Dimethylformamide (500 ml), 2,2-dimethoxypropane (210 ml) and p-toluenesulfonic acid monohydrate (18.61 g) were added to the resulting residue. The resulting mixture was stirred at room temperature for 14 hours. A saturated sodium bicarbonate solution (1 L) and water (1 L) were added to the reaction mixture, followed by extraction with ethyl acetate. The organic layer was successively washed with water and saturated saline in this order, and it was then dried over anhydrous sodium sulfate. After filtration, the filtrate was concentrated to about 100 ml under reduced pressure. Hexane was added to the residue, and the precipitate was then collected by filtration, so as to obtain the title compound (53.88 g) as a solid.

$^1$H-NMR (DMSO-D$_6$) δ: 1.22-1.32 (6H, m), 1.72-2.23 (2H, m), 2.50 (1H, s), 3.50 (1H, td, J=14.2, 6.9 Hz), 4.22-3.92 (2H, m), 5.06-5.36 (2H, m), 7.43 (2H, d, J=12.8 Hz).

ESI-MS m/z: 308 (M+H)$^+$.

(3) 1-(2-Amino-4,6-dichloropyrimidin-5-yl)-2-(2,2-dimethyl-[1,3]dioxolan-4-yl)ethan-1-one

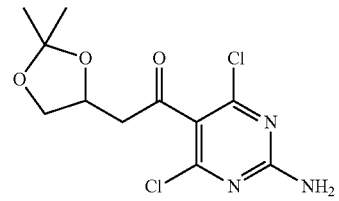 [SMILES: CC1(C)OCC(CC(=O)c2c(Cl)nc(N)nc2Cl)O1]

Acetic anhydride (149 ml) was added dropwise to a mixture composed of the above 1-(2-amino-4,6-dichloropyrimidin-5-yl)-2-(2,2-dimethyl-[1,3]dioxolan-4-yl)ethan-1-ol (74.70 g) and dimethyl sulfoxide (600 ml) at room temperature over 15 minutes under cooling in an ice bath. The reaction mixture was then stirred at the same temperature as above for 18 hours. After the disappearance of the materials had been confirmed, the reaction solution was poured into ice water. The precipitated solid was collected by filtration, so as to obtain the title compound (68.26 g).

$^1$H-NMR (CDCl$_3$) δ: 1.37 (3H, s), 1.42 (3H, s), 2.98-3.06 (1H, m), 3.32-3.40 (1H, m), 3.67-3.72 (1H, m), 4.25-4.30 (1H, m), 4.57-4.64 (1H, m), 5.72 (2H, s).

ESI-MS m/z: 306 (M+H)$^+$.

(4) 4-Chloro-3-[(2,2-dimethyl-1,3-dioxolan-4-yl)methyl]-1-(4-methoxybenzyl)-1H-pyrazolo[3,4-d]pyrimidine-6-amine

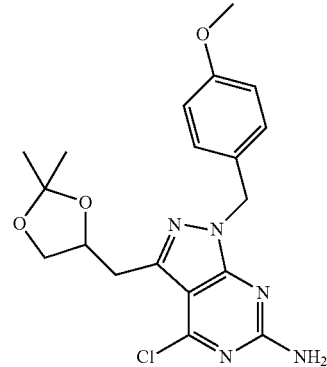 [SMILES: COc1ccc(Cn2nc(CC3COC(C)(C)O3)c3c(Cl)nc(N)nc32)cc1]

Triethylamine (83.68 ml) was added to a mixture composed of the above 1-(2-amino-4,6-dichloropyrimidin-5-yl)-2-(2,2-dimethyl-[1,3]dioxolan-4-yl)ethan-1-one (61.23 g), (4-methoxybenzyl)-hydrazine hydrochloride (41.50 g) produced by the method described in U.S. Patent No. US2003/18197, and dichloromethane (600 ml) over 30 minutes under cooling in an ice bath. Thereafter, while the temperature of the reaction solution was gradually raised, it was stirred for 17 hours. Thereafter, a 10% citric acid aqueous solution was added to the reaction mixture, followed by extraction with dichloromethane. The organic layer was dried over anhydrous sodium sulfate and was then concentrated under reduced pressure. A 5% citric acid aqueous solution was added to the resulting residue, and the precipitate was then collected by filtration. The resultant was washed with water, so as to obtain the title compound (73.84 g) as a solid.

$^1$H-NMR (CDCl$_3$) δ: 1.36 (3H, s), 1.43 (3H, s), 3.11 (1H, dd, J=14.7, 8.1 Hz), 3.43 (1H, dd, J=14.7, 5.2 Hz), 3.73-3.78 (4H, m), 4.08 (1H, dd, J=8.1, 6.0 Hz), 4.54-4.61 (1H, m), 4.77 (2H, brs), 5.22 (2H, s), 6.83 (2H, d, J=8.5 Hz), 7.24 (2H, d, J=8.5 Hz).

ESI-MS m/z: 404 (M+H)$^+$.

(5) Di-tert-butyl{4-chloro-3-[(2,2-dimethyl-1,3-diox-olan-4-yl)methyl]-1-(4-methoxybenzyl)-1H-pyrazolo[3,4-d]pyrimidin-6-yl}imide dicarbonate

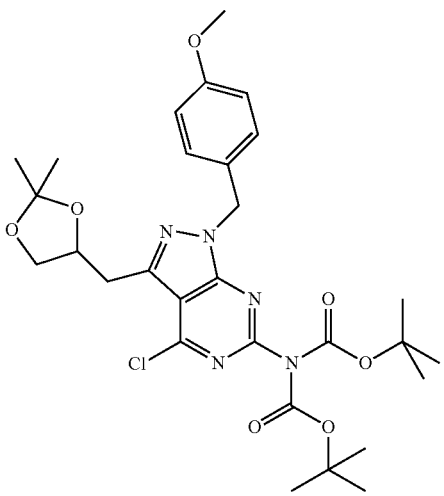 [SMILES: COc1ccc(Cn2nc(CC3COC(C)(C)O3)c3c(Cl)nc(N(C(=O)OC(C)(C)C)C(=O)OC(C)(C)C)nc32)cc1]

4-Dimethylaminopyridine (2.20 g) and di-tert-butyl dicarbonate (86.59 g) were added to a mixture composed of the above 4-chloro-3-[(2,2-dimethyl-1,3-dioxolan-4-yl)methyl]-1-(4-methoxybenzyl)-1H-pyrazolo[3,4-d]pyrimidine-6-amine (72.83 g) and tetrahydrofuran (700 ml), and the resulting mixture was then stirred at room temperature for 12 hours. Thereafter, the reaction mixture was filtered, and the filtrate was then concentrated under reduced pressure. The resulting residue was purified by silica gel column chromatography (ethyl acetate-hexane), so as to obtain the title compound (70.00 g) as an amorphous substance.

$^1$H-NMR (CDCl$_3$) δ: 1.37 (3H, s), 1.40 (3H, s), 1.44-1.46 (18H, m), 3.21-3.29 (1H, m), 3.48-3.55 (1H, m), 3.74-3.81 (4H, m), 4.09-4.15 (1H, m), 4.58-4.66 (1H, m), 5.48 (2H, dd, J=17.3, 15.1 Hz), 6.81 (2H, d, J=7.8 Hz), 7.27-7.30 (2H, m).
ESI-MS m/z: 604 (M+H)$^+$.

(6) Di-tert-butyl[4-chloro-3-(2,3-dihydroxypropyl)-1-(4-methoxybenzyl)-1H-pyrazolo[3,4-d]pyrimidin-6-yl]imide dicarbonate

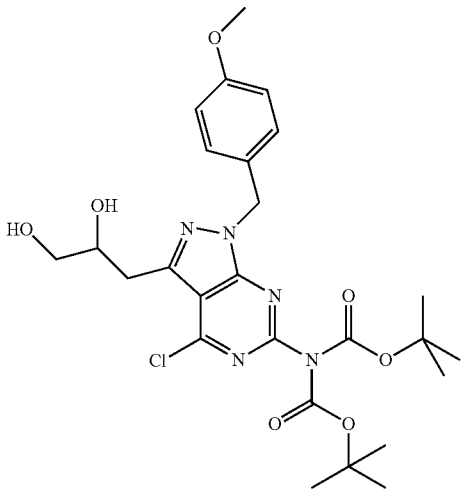 [SMILES: COc1ccc(Cn2nc(CC(O)CO)c3c(Cl)nc(N(C(=O)OC(C)(C)C)C(=O)OC(C)(C)C)nc32)cc1]

The above di-tert-butyl{4-chloro-3-[(2,2-dimethyl-1,3-dioxolan-4-yl)methyl]-1-(4-methoxybenzyl)-1H-pyrazolo[3,4-d]pyrimidin-6-yl}imide dicarbonate (53.85 g) was dissolved in acetonitrile (500 ml), and copper(II) chloride dihydrate (30.39 g) was then added to the solution. The resulting mixture was stirred at room temperature for 2 hours. Thereafter, a saturated ammonium chloride aqueous solution was added to the reaction solution, followed by extraction with ethyl acetate. The organic layer was washed with saturated saline, and it was then dried over anhydrous sodium sulfate, followed by concentration under reduced pressure. The resulting residue was purified by silica gel column chromatography (ethyl acetate-hexane), so as to obtain the title compound (37.70 g) as an amorphous substance.

$^1$H-NMR (CDCl$_3$) δ: 1.46 (18H, s), 3.15 (1H, d, J=3.7 Hz), 3.23-3.33 (2H, m), 3.62-3.82 (5H, m), 4.26-4.34 (1H, m), 5.49 (2H, t, J=15.9 Hz), 6.82 (2H, d, J=8.1 Hz), 7.25-7.30 (2H, m).
ESI-MS m/z: 564 (M+H)$^+$.

(7) Di-tert-butyl[8-hydroxy-2-(4-methoxybenzyl)-2,7,8,9-tetrahydro-6-thia-1,2,3,5-tetraazabenzo[cd]azulen-4-yl]imide dicarbonate

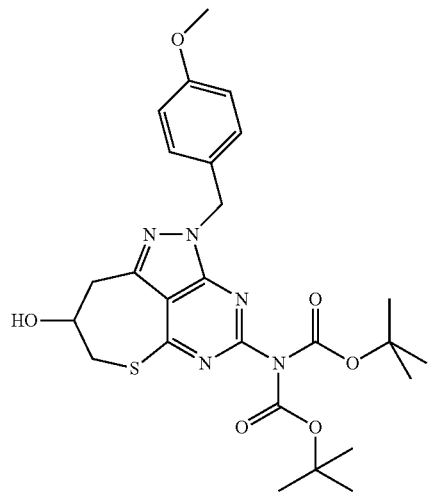 [SMILES: COc1ccc(Cn2nc3c4c(nc(N(C(=O)OC(C)(C)C)C(=O)OC(C)(C)C)nc42)SCC(O)C3)cc1]

Methanesulfonyl chloride (4.23 ml) was added dropwise to a mixture composed of the above di-tert-butyl[4-chloro-3-(2,3-dihydroxypropyl)-1-(4-methoxybenzyl)-1H-pyrazolo[3,4-d]pyrimidin-6-yl]imide dicarbonate (28.00 g), 2,4,6-collidine (16.53 ml) and anhydrous dichloromethane (400 ml) under cooling in an ice bath. The resulting mixture was then stirred at 4° C. for 15 hours. Thereafter, a 10% citric acid aqueous solution was added to the reaction mixture, followed by extraction with dichloromethane. The organic layer was dried over anhydrous sodium sulfate, and it was then concentrated under reduced pressure. The resulting residue was dissolved in N,N-dimethylformamide (300 ml), and sodium hydrogensulfide monohydrate (5.52 g) was then added to the solution under cooling in an ice bath. Thereafter, the resulting mixture was stirred at room temperature for 1.5 hours. Thereafter, potassium carbonate (10.29 mg) was added to the reaction mixture, and the resulting mixture was then heated to 50° C., followed by a further stirring operation for 5 hours. Subsequently, ethyl acetate was added to the reaction mixture, and the resultant was then successively washed with a 10% citric acid aqueous solution and then with a saturated saline. The resultant was dried over anhydrous sodium sulfate, and it was then concentrated under reduced pressure. The resulting residue was purified by silica gel column chromatography (ethyl acetate-hexane), so as to obtain the title compound (20.59 g) as a solid.

$^1$H-NMR (CDCl$_3$) δ: 1.45 (18H, s), 2.39 (1H, brs), 3.29-3.51 (4H, m), 4.58 (1H, brs), 3.76 (3H, s), 5.42-5.49 (2H, m), 6.82 (2H, d, J=8.6 Hz), 7.30 (2H, d, J=8.6 Hz).
ESI-MS m/z: 544 (M+H)$^+$.

(8) 4-[Bis(tert-butoxycarbonyl)amino]-2-(4-methoxybenzyl)-2,7-dihydro-6-thia-1,2,3,5-tetraazabenzo[cd]azulen-8-yl acetate

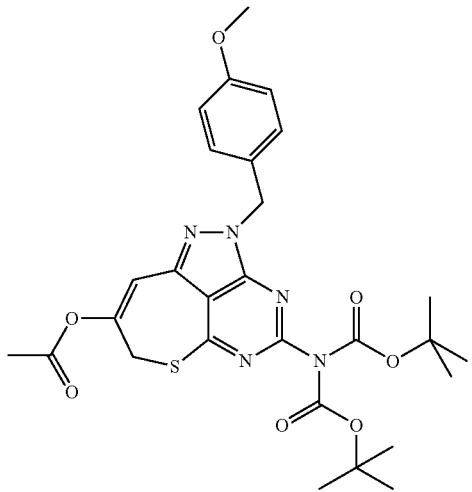 [SMILES: COc1ccc(Cn2nc3c4c(nc(N(C(=O)OC(C)(C)C)C(=O)OC(C)(C)C)nc42)SCC(OC(C)=O)=C3)cc1]

In a nitrogen atmosphere, acetic anhydride (14 ml) was added dropwise to a mixture composed of the above di-tert-butyl[8-hydroxy-2-(4-methoxybenzyl)-2,7,8,9-tetrahydro-6-thia-1,2,3,5-tetraazabenzo[cd]azulen-4-yl]imide dicarbonate (8.17 g), dimethyl sulfoxide (74 ml), and pyridine (12 ml) under cooling on ice, and the resulting mixture was then stirred for 30 minutes. Thereafter, the reaction solution was further stirred at room temperature for 15 hours. After the disappearance of the materials had been confirmed, the reaction mixture was diluted with ethyl acetate, and it was then washed with a saturated saline. The organic layer was dried over anhydrous sodium sulfate, followed by concentration under reduced pressure. The resulting residue was purified by silica gel column chromatography (ethyl acetate-hexane), so as to obtain the title compound (6.15 g) as an amorphous substance.

$^1$H-NMR (CDCl$_3$) δ: 1.44 (18H, s), 2.26 (3H, s), 3.77 (3H, s), 3.88 (2H, s), 5.50 (2H, s), 6.68 (1H, s), 6.83 (2H, d, J=8.8 Hz), 7.31 (2H, d, J=8.8 Hz).

ESI-MS m/z: 584 (M+H)$^+$.

(9) Di-tert-butyl[2-(4-methoxybenzyl)-8-oxo-2,7,8,9-tetrahydro-6-thia-1,2,3,5-tetraazabenzo[cd]azulen-4-yl]imide dicarbonate

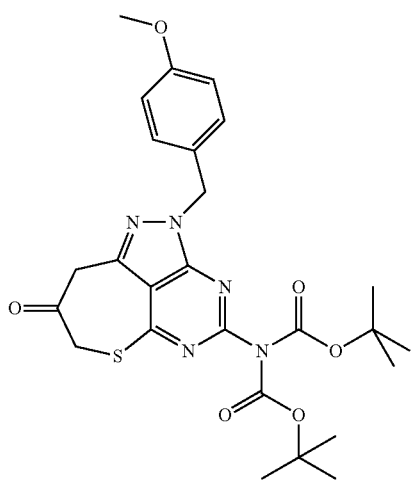 [SMILES: COc1ccc(Cn2nc3c4c(nc(N(C(=O)OC(C)(C)C)C(=O)OC(C)(C)C)nc42)SCC(=O)C3)cc1]

A mixture composed of the above 4-[bis(tert-butoxycarbonyl)amino]-2-(4-methoxybenzyl)-2,7-dihydro-6-thia-1,2,3,5-tetraazabenzo[cd]azulen-8-yl acetate (6.15 g), methanol (200 ml), and potassium carbonate (0.73 g) was stirred for 1.5 hours under cooling in an ice bath. After the disappearance of the materials had been confirmed, a saturated ammonium chloride aqueous solution was added to the reaction mixture, followed by extraction with ethyl acetate. The organic layer was washed with a saturated saline, and it was then dried over anhydrous sodium sulfate, followed by concentration under reduced pressure, so as to obtain the title compound (5.70 g) as an amorphous substance.

$^1$H-NMR (CDCl$_3$) δ: 1.46 (18H, s), 3.84 (2H, s), 3.77 (3H, s), 4.23 (2H, s), 5.48 (2H, s), 6.83 (2H, d, J=8.6 Hz), 7.32 (2H, d, J=8.6 Hz).

ESI-MS m/z: 542 (M+H)$^+$.

(10) Ethyl {4-[bis(tert-butoxycarbonyl)amino]-2-(4-methoxybenzyl)-2,7-dihydro-6-thia-1,2,3,5-tetraazabenzo[cd]azulen-8-yl}acetate

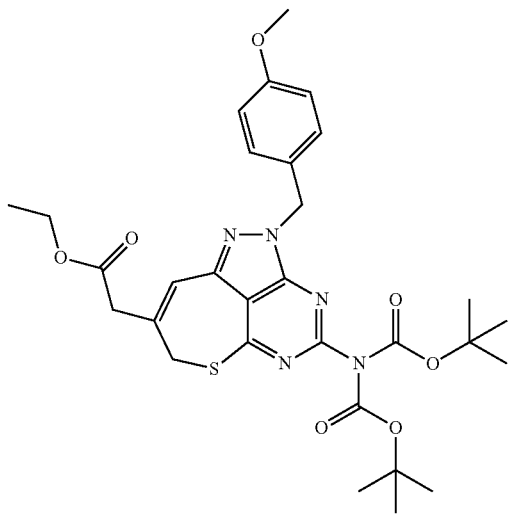 [SMILES: CCOC(=O)CC1=Cc2nn(Cc3ccc(OC)cc3)c3nc(N(C(=O)OC(C)(C)C)C(=O)OC(C)(C)C)nc(c23)SC1]

A mixture composed of the above di-tert-butyl[2-(4-methoxybenzyl)-8-oxo-2,7,8,9-tetrahydro-6-thia-1,2,3,5-tetraazabenzo[cd]azulen-4-yl]imide dicarbonate (5.19 g), ethyl (triphenylphosphanylidene)acetate (3.51 g), and toluene (300 ml) was stirred at 65° C. for 13 hours. Thereafter, the reaction mixture was concentrated under reduced pressure, and the residue was then purified by silica gel column chromatography (ethyl acetate-hexane), so as to obtain the title compound (3.78 g) as an amorphous substance.

$^1$H-NMR (CDCl$_3$) δ: 1.29 (3H, t, J=7.1 Hz), 1.69-1.77 (1H, m), 2.37-2.40 (1H, m), 2.46-2.52 (1H, m), 2.68-2.71 (2H, m), 4.20 (2H, q, J=7.1 Hz), 5.10-5.13 (1H, m), 5.20 (2H, brs).

ESI-MS m/z: 612 (M+H)$^+$

(11) 2-(4-amino-2,7-dihydro-6-thia-1,2,3,5-tetraazabenzo[cd]azulen-8-yl)-N-methylacetamide trifluoroacetate

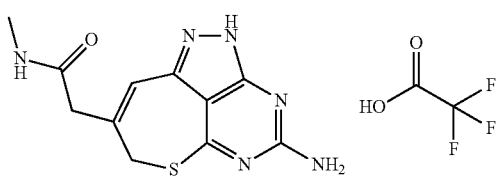 [SMILES: CNC(=O)CC1=Cc2n[nH]c3nc(N)nc(c23)SC1 ; O=C(O)C(F)(F)F]

The above ethyl {4-[bis(tert-butoxycarbonyl)amino]-2-(4-methoxybenzyl)-2,7-dihydro-6-thia-1,2,3,5-tetraazabenzo[cd]azulen-8-yl}acetate (2.2 g) was dissolved in a 40% methylamine/methanol solution (40 ml), and the mixed solution was then stirred at room temperature for 2 hours. The completion of the reaction was confirmed by LC-MS, and the solvent was then distilled away under reduced pressure. Thereafter, anisole (2 ml) and trifluoroacetic acid (40 ml) were added to the resulting residue, and the resulting mixture was then stirred at 65° C. for 15 hours. Thereafter, the reaction solution was concentrated under reduced pressure, and an isopropyl ether-ether mixed solution was then added to the residue. The precipitate was collected by filtration, so as to obtain the title compound (1.53 g) as a solid.

ESI-MS m/z: 277 (M+H)+.

(12) 5-Chloro-4-hydroxy-6-methylnicotinic acid

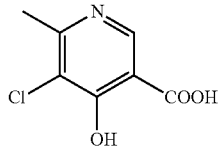

Commercially available 4-hydroxy-6-methyl-nicotinic acid (300 mg) was suspended in 3 ml of acetonitrile, and N-chlorosuccinimide (380 mg) was then added to the suspension. The resulting mixture was stirred at room temperature for 30 minutes. Thereafter, the reaction solution was heated under reflux for 45 minutes. After the disappearance of the materials had been confirmed, the reaction solution was cooled on ice, and the precipitate was then collected by filtration, so as to obtain the title compound (324 mg) as a solid.

$^1$H-NMR (CD$_3$OD) δ: 2.56 (3H, s), 8.50 (1H, s).

ESI-MS m/z: 188 (M+H)+

(13) Methyl 4,5-dichloro-6-methylnicotinate

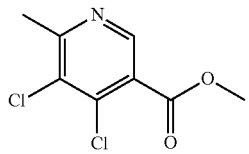

Phosphorus oxychloride (1.13 ml) was added to the above 5-chloro-4-hydroxy-6-methylnicotinic acid (320 mg), and the resulting mixture was then heated under reflux for 2 hours. Thereafter, the reaction solution was concentrated under reduced pressure, and methanol (3 ml) was then added dropwise to the residue under cooling on ice. The resulting mixture was stirred at room temperature for 30 minutes, followed by concentration under reduced pressure. A saturated sodium bicarbonate solution was added to the residue under cooling on ice, followed by extraction with ethyl acetate. The organic layer was dried over anhydrous sodium sulfate, and the solvent was then distilled away, so as to obtain a crude product of the title compound (436 mg) as a solid.

ESI-MS m/z: 220 (M+H)+

(14) Methyl 5-chloro-4-methoxy-6-methylnicotinate

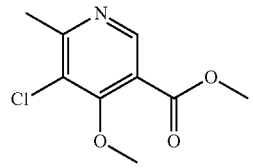

Crude methyl 4,5-dichloro-6-methylnicotinate (380 mg) was dissolved in 3 ml of methanol and, in a nitrogen stream, sodium methoxide (120 mg) was then added to the solution under cooling on ice. The temperature of the reaction solution was gradually raised to room temperature, and it was stirred for 18 hours. After the disappearance of the materials had been confirmed, a saturated ammonium chloride aqueous solution was added to the reaction solution under cooling on ice, followed by extraction with chloroform. The organic layer was dried over anhydrous sodium sulfate, and the solvent was then distilled away. The residue was purified by silica gel chromatography (ethyl acetate-hexane), so as to obtain the title compound (210 mg) as a solid.

1H-NMR (CDCl$_3$) δ: 2.67 (3H, s), 3.95 (4H, s), 4.00 (3H, s), 8.76 (1H, s).

ESI-MS m/z: 216 (M+H)+

(15) (5-Chloro-4-methoxy-6-methylpyridin-3-yl)methanol

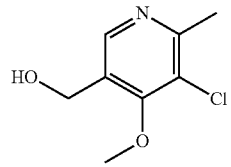

The above methyl 5-chloro-4-methoxy-6-methylnicotinate (1.0 g) was dissolved in 30 ml of methanol, and sodium borohydride (1.75 g) was then added to the solution. The resulting mixture was heated under reflux for 1 hour. Thereafter, a saturated ammonium chloride aqueous solution was added to the reaction solution under cooling on ice, followed by extraction with chloroform three times. The organic layer was dried over anhydrous sodium sulfate, and the solvent was then distilled away, so as to obtain the title compound (0.92 g) as an oily substance.

1H-NMR (CDCl$_3$) δ: 2.63 (3H, s), 4.00 (3H, s), 4.71 (2H, brs), 8.33 (1H, s)

ESI-MS m/z: 188 (M+H)+

(16) 3-Chloro-5-(chloromethyl)-4-methoxy-2-methylpyridine

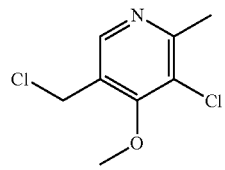

The above (5-chloro-4-methoxy-6-methylpyridin-3-yl)methanol (520 mg) was dissolved in 20 ml of chloroform, and thionyl chloride (0.38 ml) was then added to the solution under cooling on ice. The resulting mixture was stirred at the same temperature as above for 3 hours. Thereafter, the reaction solution was concentrated, and ethyl acetate was then added to the concentrate. The resulting mixture was washed with saturated sodium bicarbonate solution, water, and saturated saline in this order. The organic layer was dried over anhydrous sodium sulfate, and the solvent was then distilled away. The residue was purified by silica gel chromatography (ethyl acetate-hexane), so as to obtain the title compound (550 mg) as an oily substance.

1H-NMR (CDCl$_3$) δ: 2.64 (3H, s), 4.05 (3H, s), 4.61 (2H, s), 8.35 (1H, s).

ESI-MS m/z: 206 (M+H)+

(17) 3-Chloro-4-methoxy-2,5-dimethylpyridine

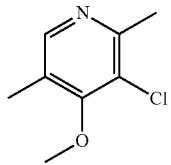

The above 3-chloro-5-(chloromethyl)-4-methoxy-2-methylpyridine (550 mg) was dissolved in 10 ml of methanol, and 10% Pd carbon (50 mg) was then added to the solution. Normal-pressure contact hydrogenation was performed on the mixture under cooling on ice for 3 hours. Thereafter, the catalyst was removed by filtration, and methanol was then distilled away under reduced pressure. The residue was extracted with chloroform. The organic layer was washed with a saturated sodium bicarbonate solution, and it was then dried over anhydrous sodium sulfate. The solvent was distilled away, and the residue was purified by silica gel chromatography (ethyl acetate-hexane), so as to obtain the title compound (365 mg) as an oily substance.

1H-NMR (CDCl$_3$) δ: 2.25 (3H, s), 2.59 (3H, s), 3.89 (3H, s), 8.16 (1H, s).

ESI-MS m/z: 172 (M+H)+

(18) 3-Chloro-4-methoxy-2,5-dimethylpyridine 1-oxide

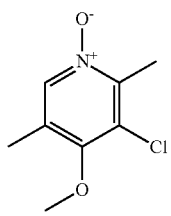

The above 3-chloro-4-methoxy-2,5-dimethylpyridine (181 mg) was dissolved in 5 ml of dichloromethane, and urea peroxide (169 mg) and phthalic anhydride (219 mg) were then added to the solution. The resulting mixture was stirred at room temperature for 2.5 hours. Thereafter, a saturated aqueous sodium thiosulfate solution was added to the reaction solution under cooling on ice, and the resulting mixture was then diluted with chloroform. The water layer was extracted with chloroform two times. The organic layer was dried over anhydrous sodium sulfate, and the solvent was then distilled away, so as to obtain the title compound (181 mg) as a solid.

1H-NMR (CDCl$_3$) δ: 2.24 (3H, s), 2.62 (3H, s), 3.87 (3H, s), 8.07 (1H, s).

ESI-MS m/z: 188 (M+H)+

(19) (3-Chloro-4-methoxy-5-methylpyridin-2-yl)methanol

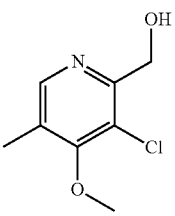

The above 3-chloro-4-methoxy-2,5-dimethylpyridine 1-oxide (530 mg) was suspended in 15 ml of dichloromethane, and trifluoroacetic anhydride (0.39 ml) was then added to the suspension under cooling on ice. The resulting mixture was stirred at room temperature for 3 hours. The reaction solution was diluted with chloroform, and was then washed with a saturated sodium bicarbonate solution. The water layer was extracted with chloroform. The organic layer was dried over anhydrous sodium sulfate, and the solvent was then distilled away, so as to obtain the title compound (521 mg) as an oily substance.

1H-NMR (CDCl$_3$) δ: 2.29 (3H, s), 3.93 (3H, s), 4.29 (1H, brs), 4.72-4.74 (2H, m), 8.26 (1H, s).

ESI-MS m/z: 188 (M+H)+

(20) 3-Chloro-2-(chloromethyl)-4-methoxy-5-methylpyridine hydrochloride

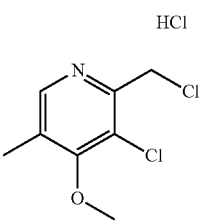

The above (3-chloro-4-methoxy-5-methylpyridin-2-yl)methanol (530 mg) was dissolved in 20 ml of chloroform, and thionyl chloride (1.03 ml) was then added dropwise to the solution under cooling on ice. The resulting mixture was stirred at room temperature for 3 hours. Thereafter, the reaction solution was concentrated, and it was then washed with a mixed solvent of ether-hexane, so as to obtain the title compound (410 mg) as a solid.

1H-NMR (CDCl$_3$) δ: 2.47 (3H, s), 4.32 (3H, s), 5.09 (2H, s), 8.54 (1H, s).

ESI-MS m/z: 206 (M+H)+

(21) 2-{4-Amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide

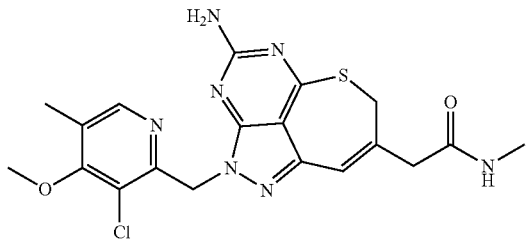

Dimethylformamide (1 ml) was added to 2-(4-amino-2,7-dihydro-6-thia-1,2,3,5-tetraazabenzo[cd]azulen-8-yl)-N-methylacetamide trifluoroacetate (28 mg), 3-chloro-2-(chloromethyl)-4-methoxy-5-methylpyridine hydrochloride (36 mg), and potassium carbonate (69 mg). The resulting mixture was stirred at 60° C. for 2.5 hours. Thereafter, the insoluble matter was removed by filtration, and the solvent was then distilled away in a nitrogen stream. The resulting residue was dissolved in dimethyl sulfoxide (1 ml), and it was then purified by preparatory reverse-phase HPLC. The solvent was distilled away under reduced pressure, so as to obtain the title compound (27.0 mg) as a solid.

$^1$H-NMR (CDCl$_3$) δ: 2.24 (4H, s), 2.82 (3H, d, J=4.9 Hz), 3.27 (2H, s), 3.80 (2H, s), 3.91 (3H, s), 5.21 (2H, s), 5.65 (2H, s), 5.87 (1H, s), 6.70 (1H, s), 8.16 (1H, s).

ESI-MS m/z: 446 (M+H)$^+$.

Example 1

2-{4-Amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide dihydrochloride Ethanol (29.3 ml) and water (0.74 ml) were added to 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide (1.034 g, 2.243 mmol), and the mixture was then stirred at 25° C. Thereafter, 2 M hydrochloric acid in ethanol (6.73 ml, 13.46 mmol) was added to the reaction mixture, and the resulting mixture was then stirred for 3 hours 45 minutes. Thereafter, the precipitated crystal was filtrated, was then washed with ethanol (5 ml), and was then dried under reduced pressure at 40° C. for 1 hour, so as to obtain the above title compound (1.118 g, 2.155 mmol). Yield: 96%.

Example 2

2-{4-Amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide dihydrochloride 3 M hydrochloric acid (369.6 mL) was added dropwise to an acetone (30 mL) suspension of 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide (493.48 mg, 1.11 mmol) at room temperature, while the suspension was stirred. The resulting mixture was further stirred for 12 hours. The obtained crystal was collected by filtration, was then washed with acetone, and was then dried under reduced pressure at 25° C. for 3 hours, so as to obtain the above title compound (531.01 mg, 1.02 mmol). Yield: 92%.

Example 3

2-{4-Amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide monohydrochloride 3 M hydrochloric acid (9.2 ml, 27.8 mmol) was added dropwise to an ethanol (200 ml) suspension of 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide (5446.6 mg, 11.6 mmol) at 25° C., while the suspension was stirred. The resulting mixture was stirred for 3.5 hours. The obtained crystal was collected by filtration, was then washed with ethanol (50 ml), and was then dried under reduced pressure at 40° C. for 14 hours, so as to obtain the above title compound (5436.1 mg, 116. mmol). Yield: 99%.

Example 4

2-{4-Amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide monohydrochloride 3 M hydrochloric acid prepared by diluting 36.2% concentrated hydrochloric acid (1.75 kg, 17.4 mol) with water (4.5 L) was added dropwise to an ethanol (123 L) suspension of 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide (3.53 kg, 7.74 mol) at a temperature from 21° C. to 22° C. over 30 minutes, while the suspension was stirred. The resulting mixture was stirred for 4 hours. The obtained crystal was collected by filtration, was then washed with ethanol (17.6 L), and was then dried under reduced pressure at 40° C. for 17 hours, so as to obtain the above title compound (3.50 kg, 7.2 mol). Yield: 93%.

Example 5

2-{4-Amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide monohydrochloride 3 M hydrochloric acid (0.527 ml, 1.58 mmol) was added dropwise to an ethanol (10.7 ml) suspension of 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide (306 mg, 0.686 mmol) at 25° C., while the suspension was stirred. The resulting mixture was stirred for 4 hours. The obtained crystal was collected by filtration, was then washed with ethanol (1.5 ml), and was then dried under reduced pressure at 40° C. for 1 hour, so as to obtain the above title compound (295 mg, 0.612 mmol). Yield: 89%.

Example 6

2-{4-Amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide monohydrochloride 3 M hydrochloric acid (0.393 ml, 1.18 mmol) was added dropwise, divided over twice, to an ethanol (30 ml) suspension of 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide (527.5 mg, 1.18 mmol) at room temperature, while the suspension was stirred. Thereafter, the resulting mixture was stirred for 1 hour. The obtained crystal was collected by filtration, was then washed with ethanol (6 ml), and was then dried under reduced pressure at 40° C. for 30 minutes, so as to obtain the above title compound (525.3 mg, 1.09 mmol). Yield: 92%.

Example 7

2-{4-Amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide monohydrochloride Ethanol (70 ml) was added to 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide (2.044 g, 4.584 mmol), and the resulting mixture was then stirred at 23° C. Thereafter, 1.5 M hydrochloric acid (3.59 ml, 5.39 mmol) was added to the reaction mixture, and the resulting mixture was then stirred for 4 hours. The precipitated crystal was filtrated, was then washed with ethanol (10 ml), and was then dried under reduced pressure at 40° C. for 1 hour, so as to obtain the above title compound (1.893 g, 3.924 mmol). Yield: 86%.

Example 8

2-{4-Amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide monohydrochloride Ethanol (72 ml) was added to 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide (2.068 g, 4.485 mmol), and the resulting mixture was then stirred at 23° C. Thereafter, 1.87 M hydrochloric acid (0.720 ml, 1.346 mmol) and 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide monohydrochloride serving as a seed crystal were added to the reaction mixture, and the resulting mixture was then stirred for 30 minutes. Thereafter, 3.28 M hydrochloric acid (0.273 ml, 0.897 mmol) was added to the reaction mixture, and the resulting mixture was then stirred for 8 minutes. This operation was repeated further eight times. Thereafter, 3.28 M hydrochloric acid (0.137 ml, 0.449 mmol) was added to the reaction mixture, and the resulting mixture was then stirred for 4 hours. The precipitated crystal was filtrated, was then washed with ethanol (10 ml), and was then dried under reduced pressure at 40° C. for 1 hour, so as to obtain the above title compound (2.057 g, 4.264 mmol). Yield: 95%.

Example 9

2-{4-Amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide monohydrochloride Ethanol (72 ml) was added to 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide (2.068 g, 4.485 mmol), and the resulting mixture was then stirred at 24° C. Thereafter, 1 M hydrochloric acid (2.691 ml, 2.691 mmol) and 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide monohydrochloride serving as a seed crystal were added to the reaction mixture, and the resulting mixture was then stirred for 30 minutes. Thereafter, 9 M hydrochloric acid (0.100 ml, 0.897 mmol) was added to the reaction mixture, and the resulting mixture was then stirred for 10 minutes. This operation was repeated further eight times and then stirred for 4 hours. The precipitated crystal was filtrated, was then washed with ethanol (10 ml), and was then dried under reduced pressure at 40° C. for 1 hour, so as to obtain the above title compound (2.044 g, 4.237 mmol). Yield: 95%.

Example 10

2-{4-Amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide monohydrochloride Ethanol (72 ml) was added to 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide (2.068 g, 4.485 mmol), and the resulting mixture was then stirred at 24° C. Thereafter, 1 M hydrochloric acid (1.346 ml, 1.346 mmol) and 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide monohydrochloride serving as a seed crystal were added to the reaction mixture, and the resulting mixture was then stirred for 30 minutes. Thereafter, 1 M hydrochloric acid (0.897 ml, 0.897 mmol) was added to the reaction mixture, and the resulting mixture was then stirred for 8 minutes. This operation was repeated further three times. Thereafter, 1 M hydrochloric acid (0.449 ml, 0.449 mmol) was added to the reaction mixture, and the resulting mixture was then stirred for 2.5 hours. Thereafter, 9 M hydrochloric acid (0.100 ml, 0.897 mmol) was added to the reaction mixture, and the resulting mixture was then stirred for 1.5 hours. Then, 9 M hydrochloric acid (0.050 ml, 0.449 mmol) was added to the reaction mixture, and the resulting mixture was then stirred for 1 hour. The precipitated crystal was filtrated, was then washed with ethanol (10 ml), and was then dried under reduced pressure at 40° C. for 30 minutes, so as to obtain the above title compound (1.742 g, 3.611 mmol). Yield: 81%.

Example 11

2-{4-Amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide monohydrochloride Ethanol (700 ml) was added to 2-{4-amino-2-[(3-chloro-4-methoxy-5-methylpyridin-2-yl)methyl]-2,7-dihydro-6- thia-1,2,3,5-tetraazabenzo[cd]azulen-8-yl}-N-methylacetamide (20.00 g, 44.85 mmol), and the resulting mixture was then stirred at 24° C. Thereafter, 1 M hydrochloric acid (13.46 ml, 13.46 mmol) and 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide monohydrochloride serving as a seed crystal were added to the reaction mixture, and the resulting mixture was then stirred for 30 minutes. Thereafter, 1 M hydrochloric acid (8.97 ml, 8.97 mmol) was added dropwise to the reaction mixture over 9 minutes. This operation was repeated further three times. Then, 1 M hydrochloric acid (4.49 ml, 4.49 mmol) was added to the reaction mixture, and the resulting mixture was then stirred for 1 hour. Thereafter, 9 M hydrochloric acid (1.00 ml, 8.97 mmol) was added to the reaction mixture, and the resulting mixture was then stirred for 1 hour 50 minutes. The precipitated crystal was filtrated, was then washed with ethanol (100 ml), and was then dried under reduced pressure at 40° C. for 1 hour, so as to obtain the above title compound (18.95 g, 39.28 mmol). Yield: 88%.

Example 12

2-{4-Amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide monohydrochloride Ethanol (2800 ml) was added to 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide (80.00 g, 173.48 mmol), and the resulting mixture was then stirred at 20° C. Thereafter, 1 M hydrochloric acid (52.06 ml, 52.06 mmol) and 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide monohydrochloride serving as a seed crystal were added to the reaction mixture, and the resulting mixture was then stirred for 30 minutes. Thereafter, 1 M hydrochloric acid (34.69 ml, 34.69 mmol) was added dropwise to the reaction mixture over 8 minutes, and the resulting mixture was then stirred for 4 minutes. This operation was repeated further three times. Then, 1 M hydrochloric acid (17.37 ml, 17.37 mmol) was added dropwise to the reaction mixture over 5 minutes, and the resulting mixture was then stirred for 4 hours. Thereafter, 9 M hydrochloric acid (3.87 ml, 34.83 mmol) was added dropwise to the reaction mixture over 5 minutes, and the resulting mixture was stirred for 2 hours 40 minutes. The precipitated crystal was filtrated, was then washed with ethanol (400 ml), and was then dried under reduced pressure at room temperature for 30 minutes and then at 40° C. for 2.5 hours, so as to obtain the above title compound (68.9 g, 142.8 mmol). Yield: 82%.

Example 13

2-{4-Amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide monohydrochloride Ethanol (72 ml) was added to 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide (2.068 g, 4.485 mmol), and the resulting mixture was then stirred at 24° C. Thereafter, 1 M hydrochloric acid (1.346 ml, 1.346 mmol) was added to the reaction mixture, and the resulting mixture was then stirred for 30 minutes. Then, 1 M hydrochloric acid (0.897 ml, 0.897 mmol) was added to the reaction mixture over 5 minutes, and the resulting mixture was then stirred for 5 minutes. This operation was repeated further three times. Thereafter, 1 M hydrochloric acid (0.449 ml, 0.449 mmol) was added to the reaction mixture, and the resulting mixture was then stirred for 30 minutes. Concentrated hydrochloric acid (0.299 ml, 3.588 mmol) was added to the reaction mixture, and the resulting mixture was then stirred for 4 hours. The precipitated crystal was filtrated, was then washed with ethanol (10 ml), and was then dried under reduced pressure at 40° C. for 30 minutes, so as to obtain the above title compound (1.942 g, 4.026 mmol). Yield: 90%.

Example 14

2-{4-Amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide monohydrochloride Ethanol (72 ml) was added to 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide (2.068 g, 4.485 mmol), and the resulting mixture was then stirred at 23° C. Thereafter, 1 M hydrochloric acid (1.346 ml, 1.346 mmol) was added to the reaction mixture, and the resulting mixture was then stirred for 25 minutes. Then, 1 M hydrochloric acid (0.897 ml, 0.897 mmol) was added to the reaction mixture over 4 minutes, and the resulting mixture was then stirred for 6 minutes. This operation was repeated further three times. Thereafter, 1 M hydrochloric acid (0.449 ml, 0.449 mmol) was added to the reaction mixture, and the resulting mixture was then stirred for 30 minutes. Concentrated hydrochloric acid (0.299 ml, 3.588 mmol) was added to the reaction mixture, and the resulting mixture was then stirred for 1 hour. The reaction mixture was cooled to 2° C. over 1 hour. Two hours later, the precipitated crystal was filtrated, was then washed with ethanol (10 ml), and was then dried under reduced pressure at 40° C. for 30 minutes, so as to obtain the above title compound (2.011 g, 4.169 mmol). Yield: 93%.

Example 15

2-{4-Amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide monohydrochloride Ethanol (72 ml) and water (3.052 ml) were added to 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide (2.068 g, 4.485 mmol), and the resulting mixture was then stirred at 23° C. Thereafter, concentrated hydrochloric acid (0.045 ml, 0.54 mmol) was added to the reaction mixture over 2 minutes, and the resulting mixture was then stirred for 10 minutes. This operation was repeated further nine times. Thereafter, the reaction mixture was stirred for 30 minutes, and concentrated hydrochloric acid (0.299 ml, 3.588 mmol) was added thereto. The resulting mixture was then stirred for 4 hours. The precipitated crystal was filtrated, was then washed with ethanol (10 ml), and was then dried under reduced pressure at 40° C. for 30 minutes, so as to obtain the above title compound (2.022 g, 4.192 mmol). Yield: 94%.

Example 16

2-{4-Amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide monohydrochloride Ethanol (36 ml) and water (3.052 ml) were added to 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide (2.068 g, 4.485 mmol), and the resulting mixture was then stirred at 25° C. Thereafter, concentrated hydrochloric acid (0.045 ml, 0.54 mmol) was added to the reaction mixture over 1 minute, and the resulting mixture was then stirred for 9 minutes. This operation was repeated further nine times. Thereafter, the reaction mixture was stirred for 30 minutes, and concentrated hydrochloric acid (0.299 ml, 3.588 mmol) was added thereto. Then, ethanol (36 ml) was added thereto over 45 minutes, and the resulting mixture was then stirred for 4 hours. The precipitated crystal was filtrated, was then washed with ethanol (10 ml), and was then dried under reduced pressure at 40° C. for 30 minutes, so as to obtain the above title compound (2.020 g, 4.187 mmol). Yield: 93%.

Example 17

2-{4-Amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide monohydrochloride Ethanol (72 ml) was added to 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide (2.068 g, 4.485 mmol), and the resulting mixture was then stirred at 24° C. Thereafter, 1 M hydrochloric acid (1.346 ml, 1.346 mmol) was added to the reaction mixture, and the resulting mixture was then stirred for 25 minutes. Then, 1 M hydrochloric acid (0.897 ml, 0.897 mmol) was added to the reaction mixture over 4 minutes, and the resulting mixture was then stirred for 7 minutes. This operation was repeated further three times. Concentrated hydrochloric acid (0.037 ml, 0.444 mmol) was added to the reaction mixture, and the resulting mixture was then stirred for 30 minutes. Thereafter, concentrated hydrochloric acid (0.374 ml, 4.488 mmol) was added to the reaction mixture over 8 minutes, and the resulting mixture was then stirred for 1 hour 20 minutes. The reaction mixture was cooled to 8° C. over 1 hour. Two hours later, the precipitated crystal was filtrated, was then washed with ethanol (10 ml), and was then dried under reduced pressure at 40° C. for 30 minutes, so as to obtain the above title compound (2.026 g, 4.200 mmol). Yield: 94%.

Example 18

2-{4-Amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide monohydrochloride Ethanol (72 ml) was added to 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide (2.068 g, 4.485 mmol), and the resulting mixture was then stirred at 24° C. Thereafter, 1 M hydrochloric acid (1.346 ml, 1.346 mmol) was added to the reaction mixture, and the resulting mixture was then stirred for 25 minutes. Then, 1 M hydrochloric acid (0.897 ml, 0.897 mmol) was added to the reaction mixture over 4 minutes, and the resulting mixture was then stirred for 7 minutes. This operation was repeated further twice. Thereafter, concentrated hydrochloric acid (0.037 ml, 0.444 mmol) was added to the reaction mixture over 1 minute, and the resulting mixture was then stirred for 9 minutes. This operation was repeated further twice, and the reaction mixture was then stirred for 30 minutes. Concentrated hydrochloric acid (0.374 ml, 4.488 mmol) was added to the reaction mixture, and the resulting mixture was then stirred for 1 hour. The reaction mixture was cooled to 10° C. over 1 hour. Two hours later, the precipitated crystal was filtrated, was then washed with ethanol (10 ml), and was then dried under reduced pressure at 40° C. for 30 minutes, so as to obtain the above title compound (2.048 g, 4.246 mmol). Yield: 95%.

Example 19

2-{4-Amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide monohydrochloride Ethanol (72 ml) was added to 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide (2.068 g, 4.485 mmol), and the resulting mixture was then stirred at 24° C. Thereafter, 1.2 M hydrochloric acid (1.346 ml, 1.615 mmol) was added to the reaction mixture, and the resulting mixture was then stirred for 25 minutes. Then, 1.2 M hydrochloric acid (0.897 ml, 1.076 mmol) was added to the reaction mixture over 5 minutes, and the resulting mixture was then stirred for 5 minutes. This operation was repeated further twice. Thereafter, concentrated hydrochloric acid (0.037 ml, 0.444 mmol) was added to the reaction mixture over 1 minute, and the resulting mixture was then stirred for 9 minutes. This operation was repeated further twice, and the reaction mixture was then stirred for 30 minutes. Concentrated hydrochloric acid (0.374 ml, 4.488 mmol) was added to the reaction mixture, and the resulting mixture was then stirred for 1 hour. The reaction mixture was cooled to 10° C. over 1 hour. Two hours later, the precipitated crystal was filtrated, was then washed with ethanol (10 ml), and was then dried under reduced pressure at 40° C. for 30 minutes, so as to obtain the above title compound (2.050 g, 4.250 mmol). Yield: 95%.

Example 20

2-{4-Amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide monohydrochloride Ethanol (41 ml) was added to 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide (2.068 g, 4.485 mmol), and the resulting mixture was then stirred at 23° C. Thereafter, 1.8 M hydrochloric acid (0.748 ml, 1.346 mmol) was added to the reaction mixture, and the resulting mixture was then stirred for 27 minutes. Then, 1.8 M hydrochloric acid (0.498 ml, 0.896 mmol) was added to the reaction mixture over 5 minutes, and the resulting mixture was then stirred for 5 minutes. This operation was repeated further three times. 1.8 M hydrochloric acid (0.249 ml, 0.448 mmol) was added to the reaction mixture, and the resulting mixture was then stirred for 30 minutes. Concentrated hydrochloric acid (0.299 ml, 3.588 mmol) was added to the reaction mixture, and the resulting mixture was then stirred for 1 hour. The reaction mixture was cooled to 3° C. over 50 minutes. Two hours 20 minutes later, the precipitated crystal was filtrated, was then washed with ethanol (10 ml), and was then dried under reduced pressure at 40° C. for 30 minutes, so as to obtain the above title compound (2.070 g, 4.291 mmol). Yield: 96%.

Example 21

2-{4-Amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide monohydrochloride Ethanol (51 ml) was added to 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide (2.068 g, 4.485 mmol), and the resulting mixture was then stirred at 23° C. Thereafter, 1.4 M hydrochloric acid (0.961 ml, 1.345 mmol) was added to the reaction mixture, and the resulting mixture was then stirred for 26 minutes. Then, 1.4 M hydrochloric acid (0.641 ml, 0.897 mmol) was added to the reaction mixture over 4 minutes, and the resulting mixture was then stirred for 6 minutes. This operation was repeated further three times. Thereafter, 1.4 M hydrochloric acid (0.320 ml, 0.448 mmol) was added to the reaction mixture, and the resulting mixture was then stirred for 30 minutes. Concentrated hydrochloric acid (0.299 ml, 3.588 mmol) was added to the reaction mixture, and the resulting mixture was then stirred for 1 hour. The reaction mixture was cooled to 2° C. over 50 minutes. Two hours 30 minutes later, the precipitated crystal was filtrated, was then washed with ethanol (10 ml), and was then dried under reduced pressure at 40° C. for 30 minutes, so as to obtain the above title compound (2.048 g, 4.246 mmol). Yield: 95%.

Example 22

2-{4-Amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide monohydrochloride Ethanol (72 ml) was added to 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide (2.068 g, 4.485 mmol), and the resulting mixture was then stirred at 25° C. Thereafter, 1 M hydrochloric acid (4.037 ml, 4.037 mmol) was added to the reaction mixture over 1 hour. Then, concentrated hydrochloric acid (0.111 ml, 1.332 mmol) was further added to the reaction mixture over 30 minutes, and the resulting mixture was then stirred for 30 minutes. Thereafter, concentrated hydrochloric acid (0.374 ml, 4.488 mmol) was added to the reaction mixture over 6 minutes, and the resulting mixture was then stirred for 1 hour. The reaction mixture was cooled to 5° C. over 1 hour. Two hours later, the precipitated crystal was filtrated, was then washed with ethanol (10 ml), and was then dried under reduced pressure at 40° C. for 30 minutes, so as to obtain the above title compound (2.037 g, 4.223 mmol). Yield: 94%.

Example 23

2-{4-Amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide monohydrochloride Ethanol (72 ml) was added to 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide (2.068 g, 4.485 mmol), and the resulting mixture was then stirred at 26° C. Thereafter, 1 M hydrochloric acid (4.037 ml, 4.037 mmol) was added to the reaction mixture over 15 minutes. Then, concentrated hydrochloric acid (0.111 ml, 1.332 mmol) was further added to the reaction mixture over 30 minutes, and the resulting mixture was then stirred for 30 minutes. Thereafter, concentrated hydrochloric acid (0.374 ml, 4.488 mmol) was added to the reaction mixture over 7 minutes, and the resulting mixture was then stirred for 1 hour. The reaction mixture was cooled to 5° C. over 1 hour. Two hours later, the precipitated crystal was filtrated, was then washed with ethanol (10 ml), and was then dried under reduced pressure at 40° C. for 30 minutes, so as to obtain the above title compound (2.037 g, 4.223 mmol). Yield: 94%.

Example 24

2-{4-Amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide monohydrochloride Ethanol (72 ml) was added to 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide (2.068 g, 4.485 mmol), and the resulting mixture was then stirred at 26° C. Thereafter, 1 M hydrochloric acid (4.037 ml, 4.037 mmol) was added to the reaction mixture over 1 hour. Then, concentrated hydrochloric acid (0.111 ml, 1.332 mmol) was further added to the reaction mixture over 5 minutes, and the resulting mixture was then stirred for 30 minutes. Thereafter, concentrated hydrochloric acid (0.374 ml, 4.488 mmol) was added to the reaction mixture over 6 minutes, and the resulting mixture was then stirred for 1 hour. The reaction mixture was cooled to 5° C. over 1 hour. Two hours later, the precipitated crystal was filtrated, was then washed with ethanol (10 ml), and was then dried under reduced pressure at 40° C. for 30 minutes, so as to obtain the above title compound (2.042 g, 4.233 mmol). Yield: 94%.

Example 25

2-{4-Amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide monohydrochloride Ethanol (72 ml) was added to 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide (2.068 g, 4.485 mmol), and the resulting mixture was then stirred at 26° C. Thereafter, 1 M hydrochloric acid (4.037 ml, 4.037 mmol) was added to the reaction mixture over 1 hour. Then, concentrated hydrochloric acid (0.111 ml, 1.332 mmol) was further added to the reaction mixture over 30 minutes, and the resulting mixture was then stirred for 30 minutes. Thereafter, concentrated hydrochloric acid (0.374 ml, 4.488 mmol) was added to the reaction mixture over 6 minutes, and the resulting mixture was then stirred for 30 minutes. The reaction mixture was cooled to 6° C. over 30 minutes. Two hours later, the precipitated crystal was filtrated, was then washed with ethanol (10 ml), and was then dried under reduced pressure at 40° C. for 30 minutes, so as to obtain the above title compound (2.040 g, 4.229 mmol). Yield: 94%.

Example 26

2-{4-Amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide hydrochloride Ethanol (72 ml) was added to 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide (2.068 g, 4.485 mmol), and the resulting mixture was then stirred at 26° C. Thereafter, 1 M hydrochloric acid (4.037 ml, 4.037 mmol) was added to the reaction mixture over 1 hour. Then, concentrated hydrochloric acid (0.111 ml, 1.332 mmol) was further added to the reaction mixture over 30 minutes, concentrated hydrochloric acid (0.374 ml, 4.488 mmol) was added to the reaction mixture over 6 minutes, and the resulting mixture was then stirred for 1 hour. The reaction mixture was cooled to 5° C. over 1 hour. Two hours later, the precipitated crystal was filtrated, was then washed with ethanol (10 ml), and was then dried under reduced pressure at 40° C. for 30 minutes, so as to obtain the above title compound (2.039 g, 4.227 mmol). Yield: 94%.

Example 27

2-{4-Amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide monohydrochloride Ethanol (180 ml) was added to 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide (5.252 g, 11.21 mmol), and the resulting mixture was then stirred at 26° C. Thereafter, 1 M hydrochloric acid (10.09 ml, 10.09 mmol) was added to the reaction mixture over 1 hour. Then, concentrated hydrochloric acid (0.280 ml, 3.360 mmol) was further added to the reaction mixture over 30 minutes, and the resulting mixture was then stirred for 30 minutes. Thereafter, concentrated hydrochloric acid (0.934 ml, 11.21 mmol) was added to the reaction mixture over 7 minutes, and the resulting mixture was then stirred for 1 hour. The reaction mixture was cooled to 5° C. over 1 hour. Twenty hours later, the precipitated crystal was filtrated, was then washed with ethanol (25 ml), and was then dried under reduced pressure at 40° C. for 1 hour, so as to obtain the above title compound (5.145 g, 10.67 mmol). Yield: 95%.

Example 28

2-{4-Amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide monohydrochloride Ethanol (36.7 L) was added to 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide (1.07 kg, 2.28 mmol), and the resulting mixture was then stirred at 25° C. Thereafter, 1 M hydrochloric acid (2.06 L, 2.06 mol) was added to the reaction mixture over 55 minutes. Then, concentrated hydrochloric acid (57 ml, 0.68 mol) was further added to the reaction mixture over 33 minutes, and the resulting mixture was then stirred for 30 minutes. Thereafter, concentrated hydrochloric acid (191 ml, 2.29 mol) was added to the reaction mixture over 11 minutes, and the resulting mixture was then stirred for 1 hour. The reaction mixture was cooled to 5° C. over 76 minutes. Twenty-two hours later, the precipitated crystal was filtrated, was then washed with ethanol (5 L), and was then dried under reduced pressure at 40° C. for 18 hours, so as to obtain the above title compound (1.05 kg, 2.18 mol). Yield: 95%.

Example 29

2-{4-Amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide monohydrochloride Ethanol (36.7 L) was added to 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide (1.07 kg, 2.28 mol), and the resulting mixture was then stirred at 24° C. Thereafter, 1 M hydrochloric acid (2.06 L, 2.06 mol) was added to the reaction mixture over 68 minutes. Then, concentrated hydrochloric acid (57 ml, 0.68 mol) was further added to the reaction mixture over 34 minutes, and the resulting mixture was then stirred for 30 minutes. Thereafter, concentrated hydrochloric acid (191 ml, 2.29 mol) was added to the reaction mixture over 9 minutes, and the resulting mixture was then stirred for 1 hour. The reaction mixture was cooled to 5° C. over 76 minutes. Twenty-two hours 30 minutes later, the precipitated crystal was filtrated, was then washed with ethanol (5 L), and was then dried under reduced pressure at 40° C. for 18 hours, so as to obtain the above title compound (1.05 kg, 2.18 mol). Yield: 95%.

Example 30

2-{4-Amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide monohydrochloride Ethanol (72 ml) was added to 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide (2.068 g, 4.485 mmol), and the resulting mixture was then stirred at 30° C. Thereafter, 1 M hydrochloric acid (4.037 ml, 4.037 mmol) was added to the reaction mixture over 1 hour. Then, concentrated hydrochloric acid (0.111 ml, 1.332 mmol) was further added to the reaction mixture over 30 minutes, and the resulting mixture was then stirred for 30 minutes. Thereafter, concentrated hydrochloric acid (0.374 ml, 4.488 mmol) was added to the reaction mixture over 6 minutes, and the resulting mixture was then stirred for 1 hour. The reaction mixture was cooled to 5° C. over 74 minutes. Two hours later, the precipitated crystal was filtrated, was then washed with ethanol (10 ml), and was then dried under reduced pressure at 40° C. for 30 minutes, so as to obtain the above title compound (2.031 g, 4.210 mmol). Yield: 94%.

Example 31

2-{4-Amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide monohydrochloride Ethanol (72 ml) was added to 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide (2.068 g, 4.485 mmol), and the resulting mixture was then stirred at 20° C. Thereafter, 1 M hydrochloric acid (4.037 ml, 4.037 mmol) was added to the reaction mixture over 1 hour. Then, concentrated hydrochloric acid (0.111 ml, 1.332 mmol) was further added to the reaction mixture over 30 minutes, and the resulting mixture was then stirred for 30 minutes. Thereafter, concentrated hydrochloric acid (0.374 ml, 4.488 mmol) was added to the reaction mixture over 5 minutes, and the resulting mixture was then stirred for 1 hour. The reaction mixture was cooled to 4° C. over 46 minutes. Two hours later, the precipitated crystal was filtrated, was then washed with ethanol (10 ml), and was then dried under reduced pressure at 40° C. for 30 minutes, so as to obtain the above title compound (2.043 g, 4.235 mmol). Yield: 94%.

Example 32

2-{4-Amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide monohydrochloride Ethanol (100.5 ml) and water (3.975 ml) were added to 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide (3.00 g, 6.40 mmol), and the resulting mixture was then stirred at 25° C. Thereafter, a water-ethanol solution (3.28 ml, 1.92 mmol) of 0.585 M hydrogen chloride that had been prepared by diluting concentrated hydrochloric acid (1.0 ml) with ethanol (19.0 ml) was added to the reaction mixture. A seed crystal (0.3 mg) was added to the mixture at the same temperature as described above, and a water-ethanol solution (6.56 ml, 3.84 mmol) of 0.585 M hydrogen chloride was added dropwise to the resulting mixture over 2 hours. The mixture was stirred for 30 minutes. Thereafter, concentrated hydrochloric acid (0.695 ml, 8.34 mmol) was added dropwise to the reaction mixture over 1 hour, and the resulting mixture was then stirred for 1 hour. The precipitated crystal was filtrated, was then washed with ethanol (15 ml), and was then dried under reduced pressure at 40° C. for 14 hours, so as to obtain the above title compound (2.89 g, 5.96 mmol). Yield: 93%.

Example 33

2-{4-Amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide monohydrochloride Ethanol (100.5 ml) and water (3.975 ml) were added to 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide (3.00 g, 6.40 mmol), and the resulting mixture was then stirred at 30° C. Thereafter, a water-ethanol solution (3.28 ml, 1.92 mmol) of 0.585 M hydrogen chloride that had been prepared by diluting concentrated hydrochloric acid (1.0 ml) with ethanol (19.0 ml) was added to the reaction mixture. A seed crystal (0.3 mg) was added to the resulting mixture at the same temperature as described above, and a water-ethanol solution (6.56 ml, 3.84 mmol) of 0.585 M hydrogen chloride was added dropwise to the resulting mixture over 2 hours. The resulting mixture was stirred for 30 minutes. Thereafter, concentrated hydrochloric acid (0.695 ml, 8.34 mmol) was added dropwise to the resulting mixture over 1 hour, and the resulting mixture was then stirred for 1 hour. The precipitated crystal was filtrated, was then washed with ethanol (15 ml), and was then dried under reduced pressure at 40° C. for 14 hours, so as to obtain the above title compound (2.86 g, 5.93 mmol). Yield: 93%.

Example 34

Measurement 1 of X-Ray Powder Diffraction

An X-ray diffraction device (model: D8 DISCOVER with GADDS CS, manufactured by Bruker AXS) was used. A sample was filled into a sample holder made of glass, and measurement was then carried out under the following conditions.

<Analysis Conditions>

X-ray: Cu Kα1/40 kV/40 mA

Goniometer: longitudinal type, biaxial (θ, θ)

2θ measurement range: 3° to 40°

Figure 4:
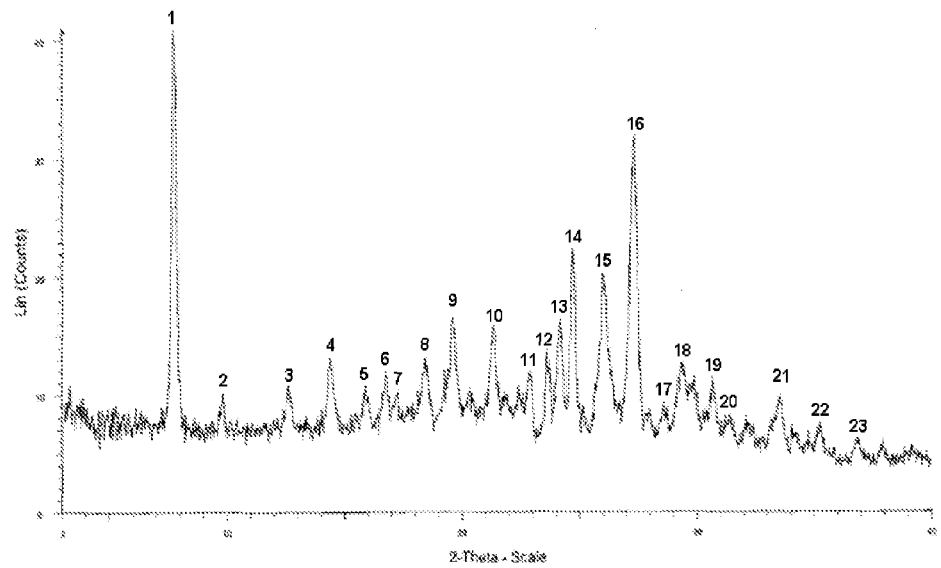
FIG. 4 shows an X-ray powder diffraction pattern of the crystal obtained in Example 2, to which peak numbers are added. The longitudinal axis of the pattern (numerical values added to the scale are 0, 10, 20, 30 and 40 from the bottom) shows diffraction intensity (Lin (Counts)), and the horizontal axis (numerical values added to the scale are 3, 10, 20, 30 and 40 from the left) shows the value of angle of diffraction 2θ.

An X-ray powder diffraction pattern of the crystal of the dihydrochloride obtained in Example 2, which was measured by the above-described method, is shown in FIG. 4. Peaks with a relative intensity of 15 or greater, when the maximum peak intensity is set at 100 in FIG. 4, are shown in Table 1.

TABLE 1

| Peak No. | 2θ | d value | Relative intensity |
|---|---|---|---|
| 1 | 7.73 | 11.44 | 100 |
| 2 | 9.78 | 9.05 | 25 |
| 3 | 12.58 | 7.04 | 26 |
| 4 | 14.36 | 6.17 | 32 |
| 5 | 15.84 | 5.59 | 26 |
| 6 | 16.71 | 5.31 | 30 |
| 7 | 17.17 | 5.17 | 24 |
| 8 | 18.40 | 4.82 | 32 |
| 9 | 19.58 | 4.53 | 40 |
| 10 | 21.31 | 4.17 | 39 |
| 11 | 22.85 | 3.89 | 29 |
| 12 | 23.62 | 3.77 | 30 |
| 13 | 24.13 | 3.69 | 40 |
| 14 | 24.70 | 3.60 | 55 |
| 15 | 26.01 | 3.43 | 50 |
| 16 | 27.29 | 3.27 | 78 |
| 17 | 28.58 | 3.12 | 23 |
| 18 | 29.37 | 3.04 | 31 |
| 19 | 30.65 | 2.92 | 28 |
| 20 | 31.38 | 2.85 | 20 |
| 21 | 33.52 | 2.67 | 24 |
| 22 | 35.25 | 2.55 | 18 |
| 23 | 36.87 | 2.44 | 15 |

Figure 5:
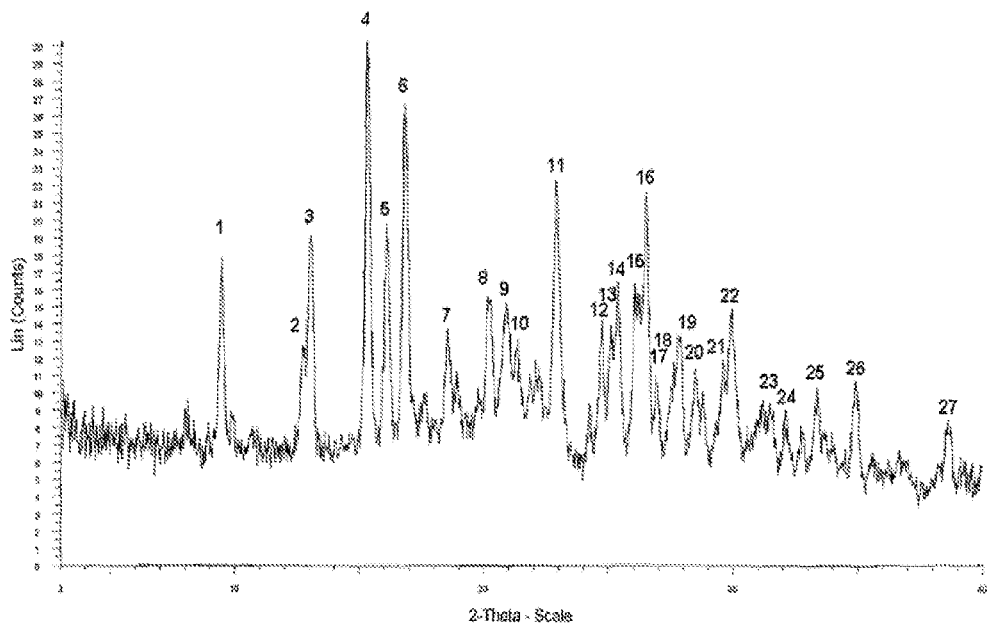
FIG. 5 shows an X-ray powder diffraction pattern of the crystal obtained in Example 3, to which peak numbers are added. The longitudinal axis of the pattern (numerical values added to the scale are 0, 1, 2, 3, 4, 5, 6, 7, 8, 9, 10, 11, 12, 13, 14, 15, 16, 17, 18, 19, 20, 21, 22, 23, 24, 25, 26, 27, 28, 29 and 30 from the bottom) shows diffraction intensity (Lin (Counts)), and the horizontal axis (numerical values added to the scale are 3, 10, 20, 30 and 40 from the left) shows the value of angle of diffraction 2θ.

An X-ray powder diffraction pattern of the crystal of the monohydrochloride obtained in Example 3, which was measured by the above-described method, is shown in FIG. 5. Peaks with a relative intensity of 30 or greater, when the maximum peak intensity is set at 100 in FIG. 5, are shown in Table 2.

TABLE 2

| Peak No. | 2θ | d value | Relative intensity |
|---|---|---|---|
| 1 | 9.43 | 9.38 | 58 |
| 2 | 12.70 | 6.97 | 42 |
| 3 | 13.03 | 6.80 | 63 |
| 4 | 15.33 | 5.78 | 100 |
| 5 | 16.10 | 5.50 | 65 |
| 6 | 16.84 | 5.26 | 88 |
| 7 | 18.55 | 4.78 | 45 |
| 8 | 20.21 | 4.39 | 50 |
| 9 | 20.89 | 4.25 | 50 |
| 10 | 21.32 | 4.17 | 42 |
| 11 | 22.93 | 3.88 | 74 |
| 12 | 24.73 | 3.60 | 47 |
| 13 | 25.10 | 3.55 | 46 |
| 14 | 25.40 | 3.51 | 54 |
| 15 | 26.10 | 3.41 | 54 |
| 16 | 26.53 | 3.36 | 71 |
| 17 | 26.95 | 3.31 | 35 |
| 18 | 27.60 | 3.23 | 39 |
| 19 | 27.88 | 3.20 | 44 |
| 20 | 28.52 | 3.13 | 37 |
| 21 | 29.63 | 3.02 | 39 |
| 22 | 29.95 | 2.98 | 49 |
| 23 | 31.55 | 2.84 | 30 |
| 24 | 32.13 | 2.79 | 30 |
| 25 | 33.40 | 2.68 | 34 |
| 26 | 34.95 | 2.57 | 35 |
| 27 | 38.70 | 2.33 | 30 |

Figure 6:
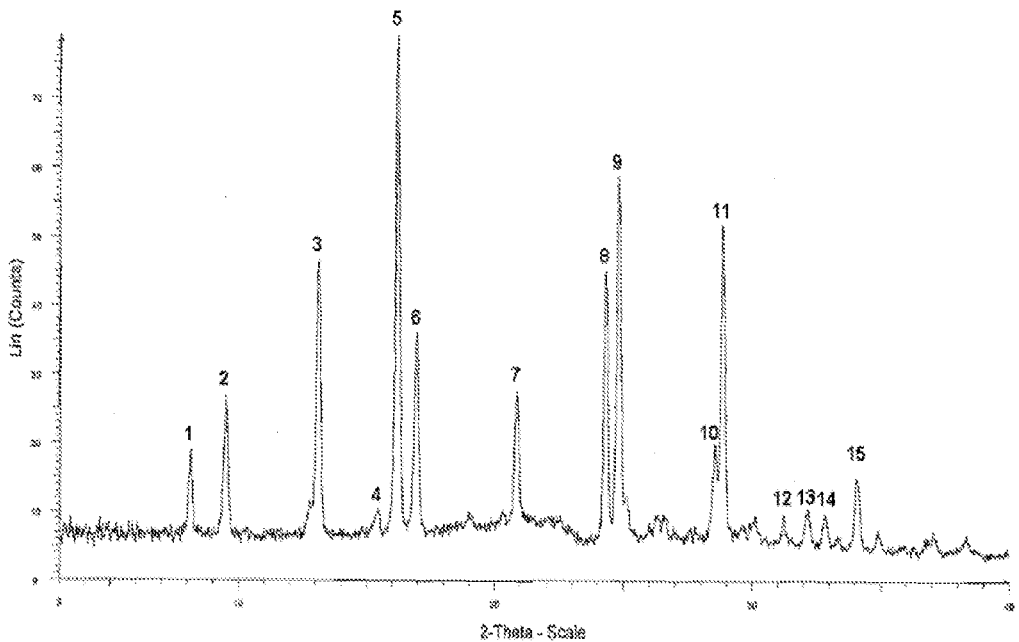
FIG. 6 shows an X-ray powder diffraction pattern of the crystal obtained in Example 6, to which peak numbers are added. The longitudinal axis of the pattern (numerical values added to the scale are 0, 10, 20, 30, 40, 50, 60 and 70 from the bottom) shows diffraction intensity (Lin (Counts)), and the horizontal axis (numerical values added to the scale are 3, 10, 20, 30 and 40 from the left) shows the value of angle of diffraction 2θ.

An X-ray powder diffraction pattern of the crystal of the monohydrochloride obtained in Example 6, which was measured by the above-described method, is shown in FIG. 6. Peaks with a relative intensity of 12 or greater, when the maximum peak intensity is set at 100 in FIG. 6, are shown in Table 3.

TABLE 3

| Peak No. | 2θ | d value | Relative intensity |
|---|---|---|---|
| 1 | 8.07 | 10.96 | 24 |
| 2 | 9.45 | 9.36 | 34 |
| 3 | 13.07 | 6.78 | 59 |
| 4 | 15.39 | 5.76 | 13 |
| 5 | 16.16 | 5.48 | 100 |
| 6 | 16.90 | 5.25 | 45 |
| 7 | 20.83 | 4.26 | 35 |
| 8 | 24.29 | 3.66 | 57 |
| 9 | 24.80 | 3.59 | 74 |
| 10 | 28.56 | 3.13 | 25 |
| 11 | 28.85 | 3.09 | 65 |
| 12 | 31.26 | 2.86 | 12 |
| 13 | 32.17 | 2.78 | 13 |
| 14 | 32.87 | 2.73 | 12 |
| 15 | 34.11 | 2.63 | 19 |

Example 35

Measurement 2 of X-Ray Powder Diffraction

Figure 7:
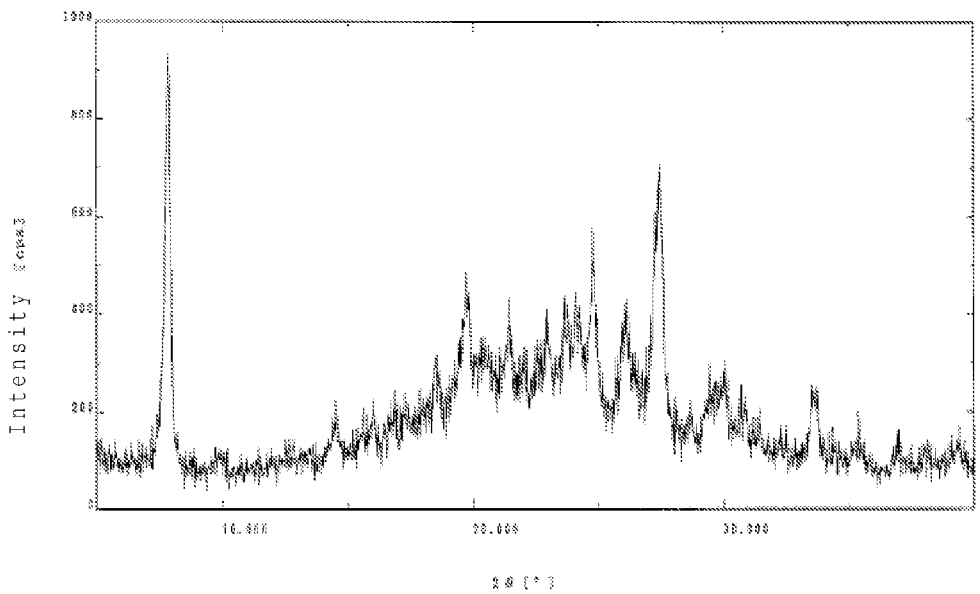
FIG. 7 shows an X-ray powder diffraction pattern of the crystal obtained in Example 1. The longitudinal axis of the pattern (numerical values added to the scale are 0, 200, 400, 600, 800 and 1000 from the bottom) shows diffraction intensity as a count/sec (cps) unit, and the horizontal axis (numerical values added to the scale are 10.000, 20.000 and 30.000 from the left) shows the value of angle of diffraction 2θ.

An X-ray diffraction device (model: RINT2200V, manufactured by Rigaku Corporation) was used. A sample was filled into a sample holder made of glass, and measurement was then carried out under the following conditions.
<Analysis Conditions>
X-ray: Cu Kα1/40 kV/40 mA
Goniometer: Ultima+horizontal goniometer type I
2θ scanning range: 5° to 40°
<Measurement Results>
An X-ray powder diffraction pattern of the crystal of the dihydrochloride obtained in Example 1, which was measured by the above-described method, is shown in FIG. 7.

Figure 8:
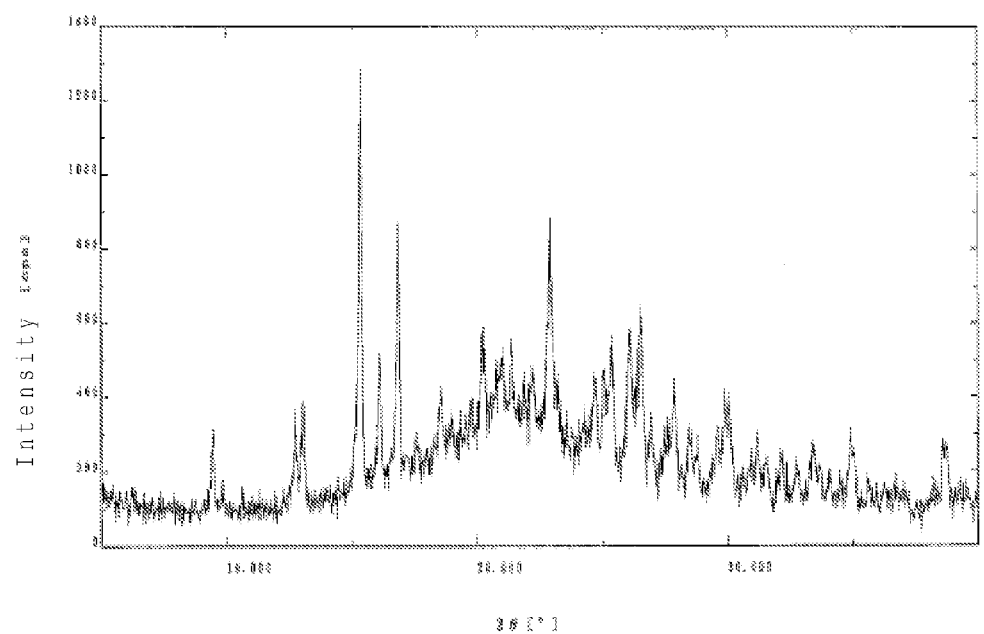
FIG. 8 shows an X-ray powder diffraction pattern of the crystal obtained in Example 4. The longitudinal axis of the pattern (numerical values added to the scale are 0, 200, 400, 600, 800, 1000, 1200 and 1400 from the bottom) shows diffraction intensity as a count/sec (cps) unit, and the horizontal axis (numerical values added to the scale are 10.000, 20.000 and 30.000 from the left) shows the value of angle of diffraction 2θ.

An X-ray powder diffraction pattern of the crystal of the monohydrochloride obtained in Example 4, which was measured by the above-described method, is shown in FIG. 8.

Figure 9:
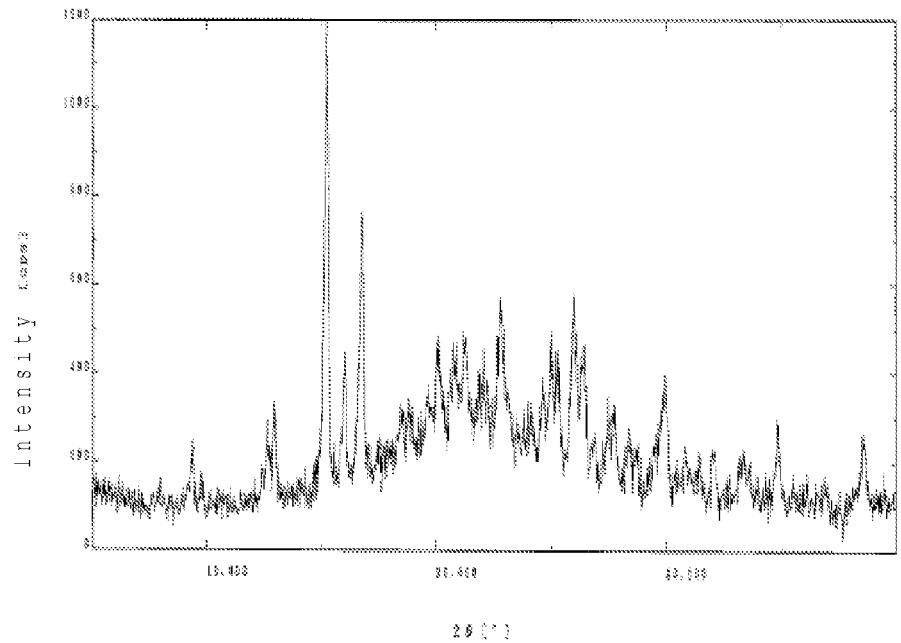
FIG. 9 shows an X-ray powder diffraction pattern of the crystal obtained in Example 5. The longitudinal axis of the pattern (numerical values added to the scale are 0, 200, 400, 600, 800, 1000 and 1200 from the bottom) shows diffraction intensity as a count/sec (cps) unit, and the horizontal axis (numerical values added to the scale are 10.000, 20.000 and 30.000 from the left) shows the value of angle of diffraction 2θ.

An X-ray powder diffraction pattern of the crystal of the monohydrochloride obtained in Example 5, which was measured by the above-described method, is shown in FIG. 9.

Figure 10:
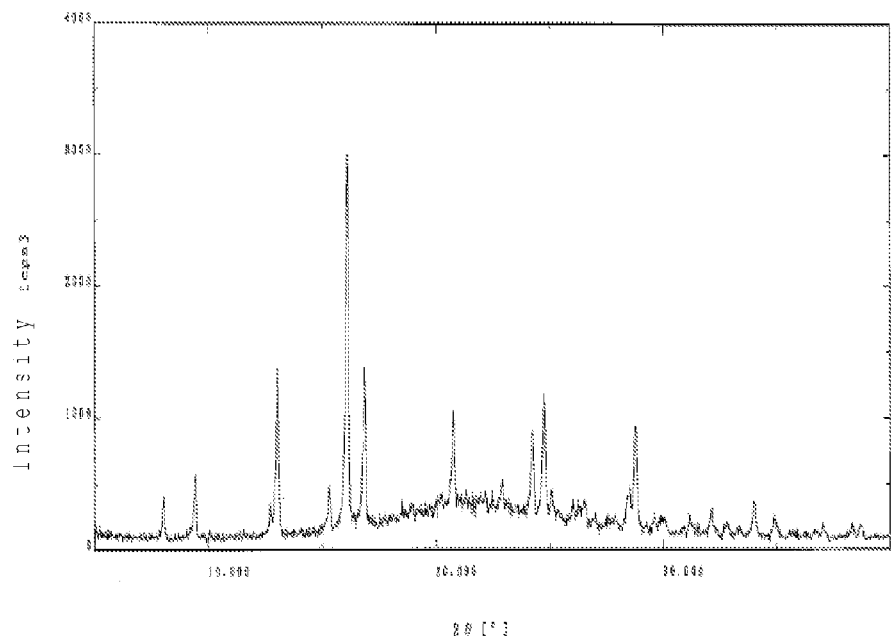
FIG. 10 is an X-ray powder diffraction pattern of the crystal obtained in Example 7. The longitudinal axis of the pattern (numerical values added to the scale are 0, 1000, 2000, 3000 and 4000 from the bottom) shows diffraction intensity as a count/sec (cps) unit, and the horizontal axis (numerical values added to the scale are 10.000, 20.000 and 30.000 from the left) shows the value of angle of diffraction 2θ.

An X-ray powder diffraction pattern of the crystal of the monohydrochloride obtained in Example 7, which was measured by the above-described method, is shown in FIG. 10.

Figure 11:
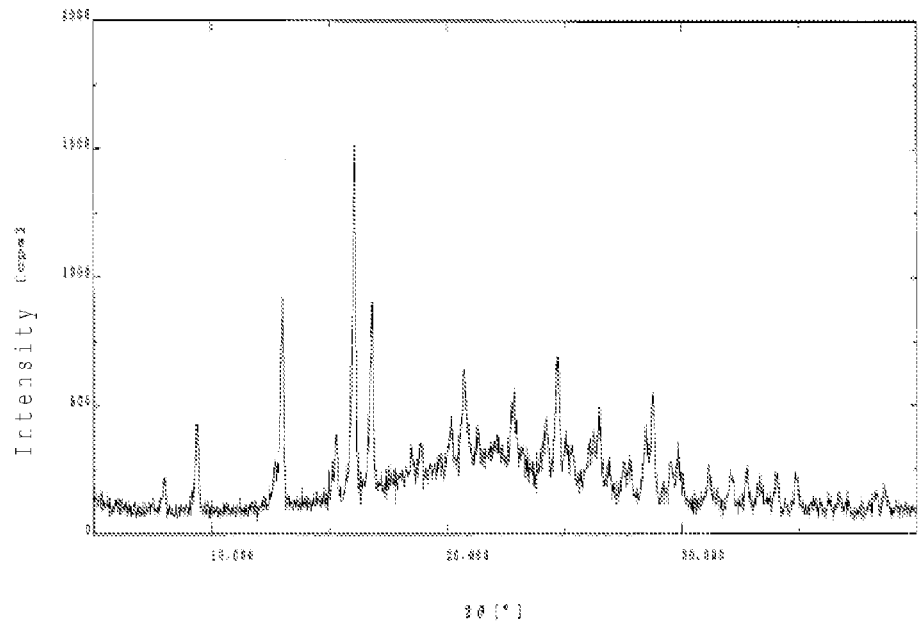
FIG. 11 shows an X-ray powder diffraction pattern of the crystal obtained in Example 8. The longitudinal axis of the pattern (numerical values added to the scale are 0, 500, 1000, 1500 and 2000 from the bottom) shows diffraction intensity as a count/sec (cps) unit, and the horizontal axis (numerical values added to the scale are 10.000, 20.000 and 30.000 from the left) shows the value of angle of diffraction 2θ.

An X-ray powder diffraction pattern of the crystal of the monohydrochloride obtained in Example 8, which was measured by the above-described method, is shown in FIG. 11.

Figure 12:
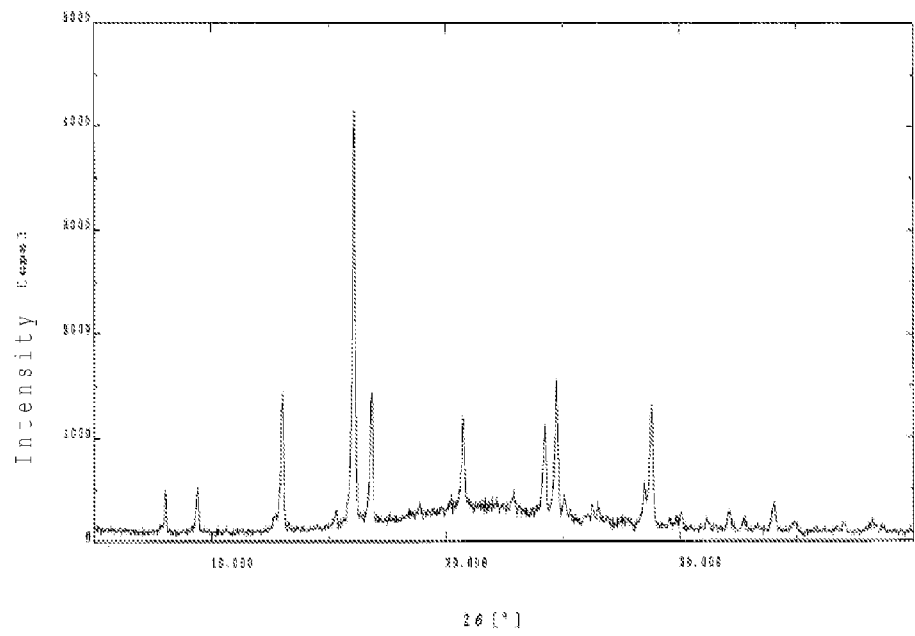
FIG. 12 shows an X-ray powder diffraction pattern of the crystal obtained in Example 9. The longitudinal axis of the pattern (numerical values added to the scale are 0, 1000, 2000, 3000, 4000 and 5000 from the bottom) shows diffraction intensity as a count/sec (cps) unit, and the horizontal axis (numerical values added to the scale are 10.000, 20.000 and 30.000 from the left) shows the value of angle of diffraction 2θ.

An X-ray powder diffraction pattern of the crystal of the monohydrochloride obtained in Example 9, which was measured by the above-described method, is shown in FIG. 12.

Figure 13:
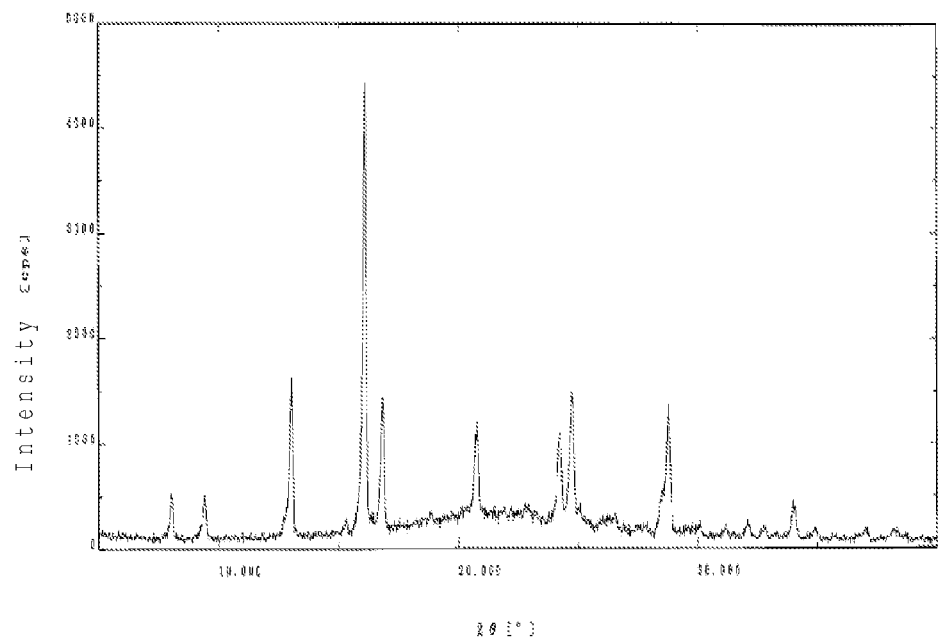
FIG. 13 shows an X-ray powder diffraction pattern of the crystal obtained in Example 10. The longitudinal axis of the pattern (numerical values added to the scale are 0, 1000, 2000, 3000, 4000 and 5000 from the bottom) shows diffraction intensity as a count/sec (cps) unit, and the horizontal axis (numerical values added to the scale are 10.000, 20.000 and 30.000 from the left) shows the value of angle of diffraction 2θ.

An X-ray powder diffraction pattern of the crystal of the monohydrochloride obtained in Example 10, which was measured by the above-described method, is shown in FIG. 13.

Figure 14:
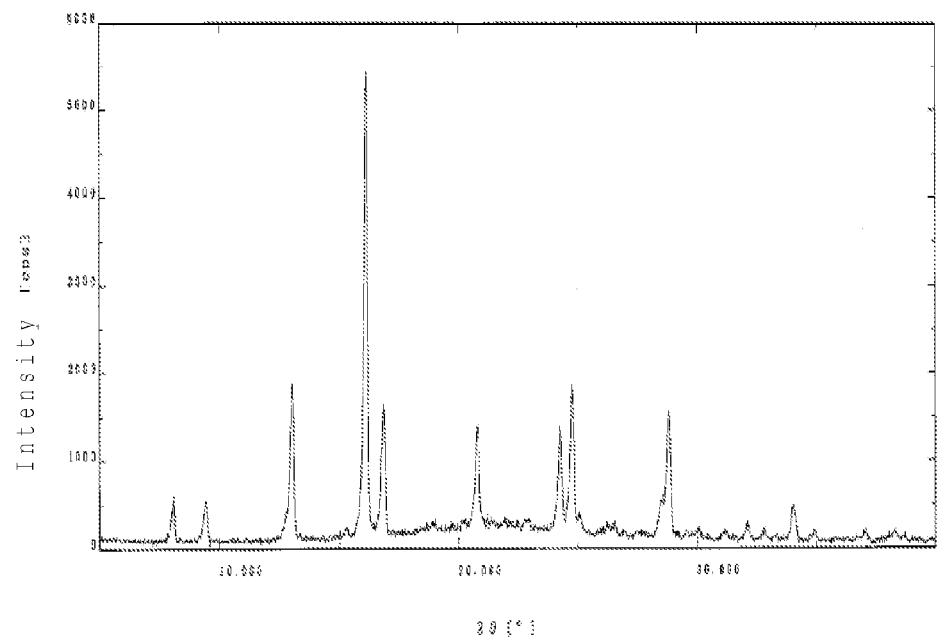
FIG. 14 shows an X-ray powder diffraction pattern of the crystal obtained in Example 11. The longitudinal axis of the pattern (numerical values added to the scale are 0, 1000, 2000, 3000, 4000, 5000 and 6000 from the bottom) shows diffraction intensity as a count/sec (cps) unit, and the horizontal axis (numerical values added to the scale are 10.000, 20.000 and 30.000 from the left) shows the value of angle of diffraction 2θ.

An X-ray powder diffraction pattern of the crystal of the monohydrochloride obtained in Example 11, which was measured by the above-described method, is shown in FIG. 14.

Figure 15:
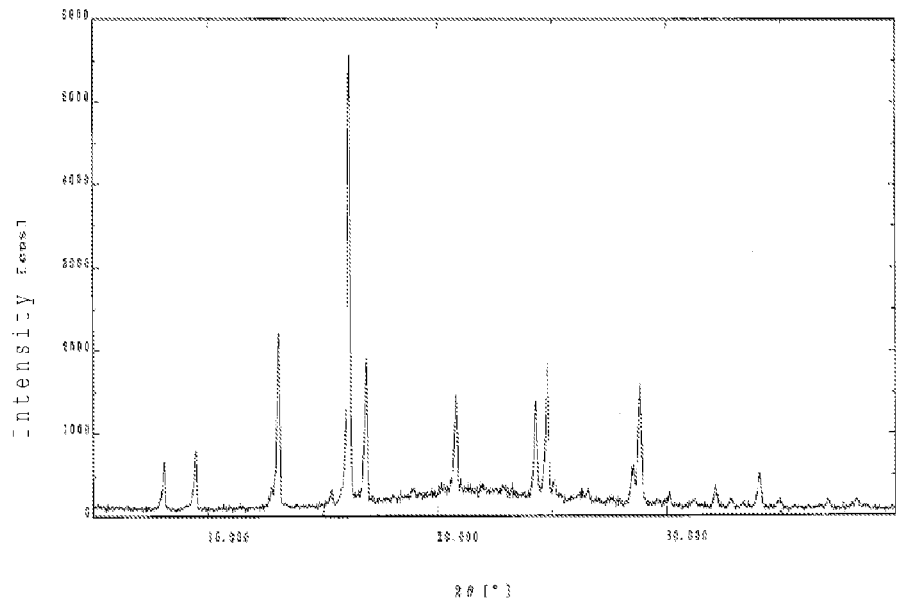
FIG. 15 shows an X-ray powder diffraction pattern of the crystal obtained in Example 12. The longitudinal axis of the pattern (numerical values added to the scale are 0, 1000, 2000, 3000, 4000, 5000 and 6000 from the bottom) shows diffraction intensity as a count/sec (cps) unit, and the horizontal axis (numerical values added to the scale are 10.000, 20.000 and 30.000 from the left) shows the value of angle of diffraction 2θ.

An X-ray powder diffraction pattern of the crystal of the monohydrochloride obtained in Example 12, which was measured by the above-described method, is shown in FIG. 15.

Figure 16:
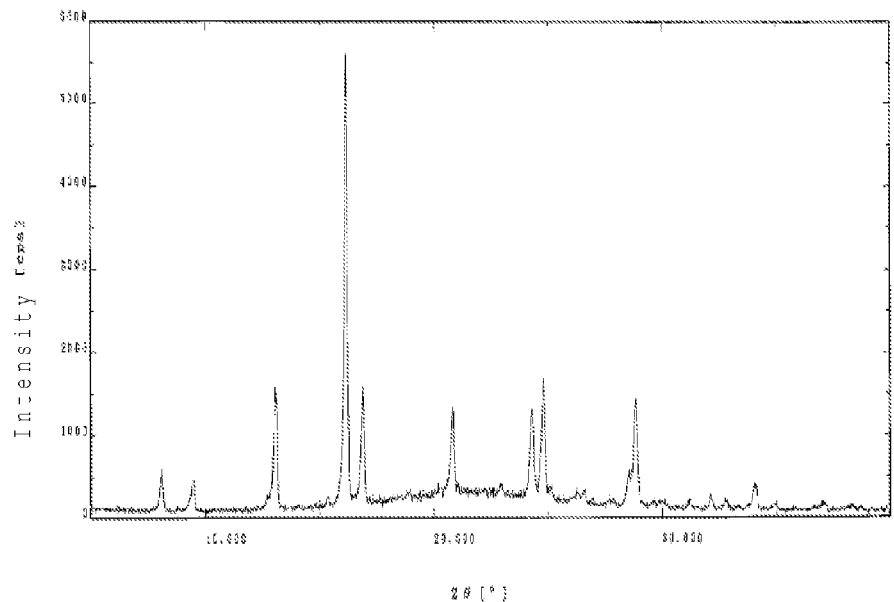
FIG. 16 shows an X-ray powder diffraction pattern of the crystal obtained in Example 13. The longitudinal axis of the pattern (numerical values added to the scale are 0, 1000, 2000, 3000, 4000, 5000 and 6000 from the bottom) shows diffraction intensity as a count/sec (cps) unit, and the horizontal axis (numerical values added to the scale are 10.000, 20.000 and 30.000 from the left) shows the value of angle of diffraction 2θ.

An X-ray powder diffraction pattern of the crystal of the monohydrochloride obtained in Example 13, which was measured by the above-described method, is shown in FIG. 16.

Figure 17:
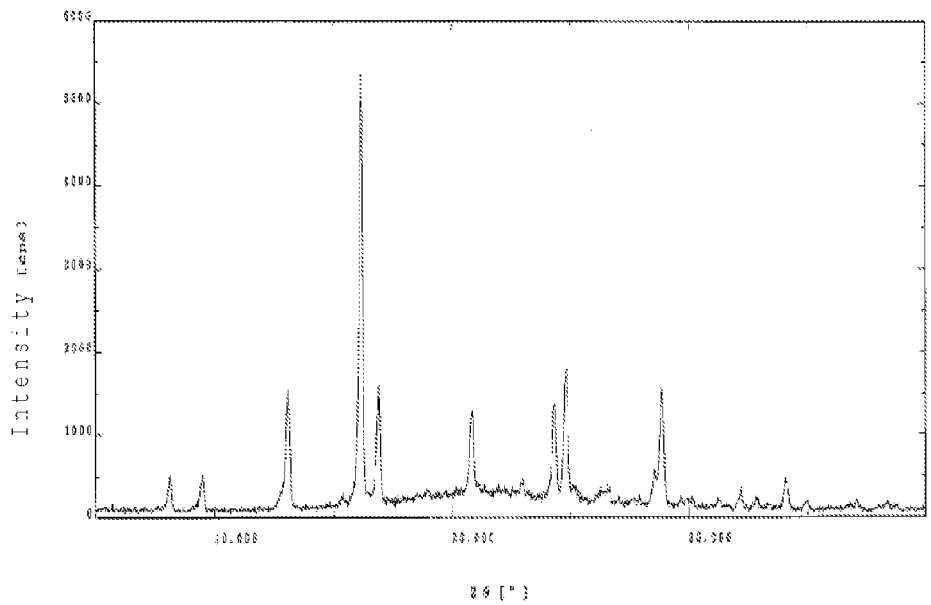
FIG. 17 shows an X-ray powder diffraction pattern of the crystal obtained in Example 14. The longitudinal axis of the pattern (numerical values added to the scale are 0, 1000, 2000, 3000, 4000, 5000 and 6000 from the bottom) shows diffraction intensity as a count/sec (cps) unit, and the horizontal axis (numerical values added to the scale are 10.000, 20.000 and 30.000 from the left) shows the value of angle of diffraction 2θ.

An X-ray powder diffraction pattern of the crystal of the monohydrochloride obtained in Example 14, which was measured by the above-described method, is shown in FIG. 17.

Figure 18:
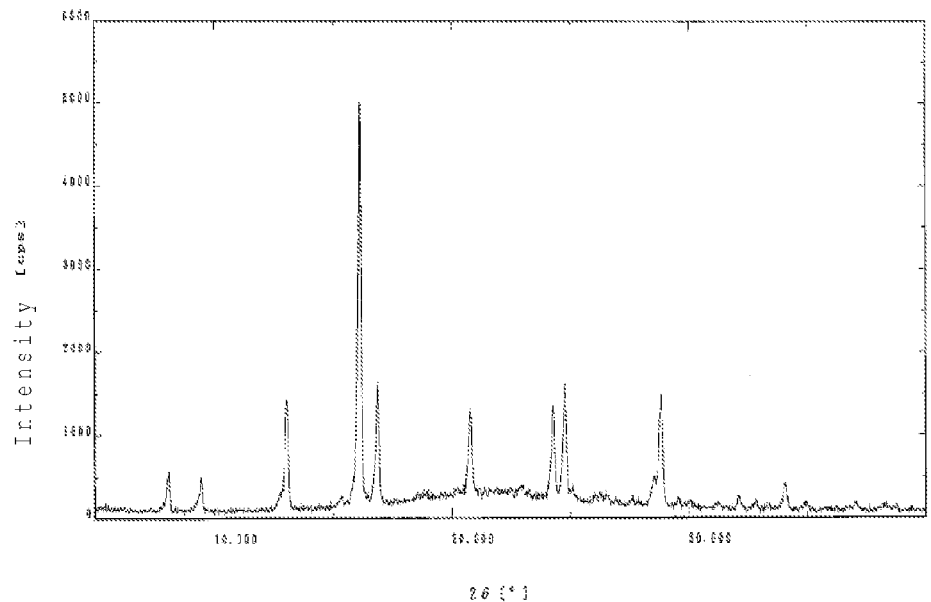
FIG. 18 shows an X-ray powder diffraction pattern of the crystal obtained in Example 15. The longitudinal axis of the pattern (numerical values added to the scale are 0, 1000, 2000, 3000, 4000, 5000 and 6000 from the bottom) shows diffraction intensity as a count/sec (cps) unit, and the horizontal axis (numerical values added to the scale are 10.000, 20.000 and 30.000 from the left) shows the value of angle of diffraction 2θ.

An X-ray powder diffraction pattern of the crystal of the monohydrochloride obtained in Example 15, which was measured by the above-described method, is shown in FIG. 18.

Figure 19:
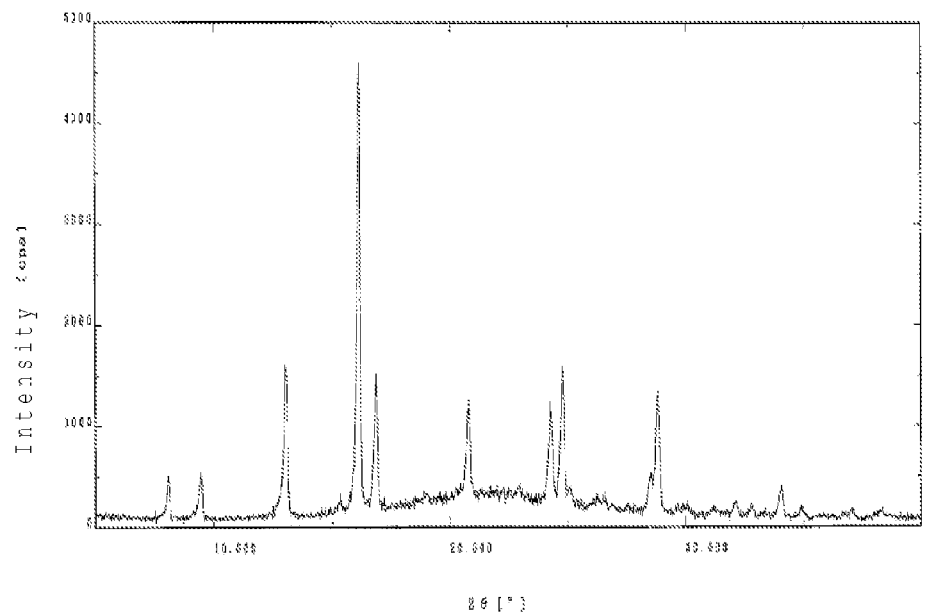
FIG. 19 shows an X-ray powder diffraction pattern of the crystal obtained in Example 16. The longitudinal axis of the pattern (numerical values added to the scale are 0, 1000, 2000, 3000, 4000 and 5000 from the bottom) shows diffraction intensity as a count/sec (cps) unit, and the horizontal axis (numerical values added to the scale are 10.000, 20.000 and 30.000 from the left) shows the value of angle of diffraction 2θ.

An X-ray powder diffraction pattern of the crystal of the monohydrochloride obtained in Example 16, which was measured by the above-described method, is shown in FIG. 19.

Figure 20:
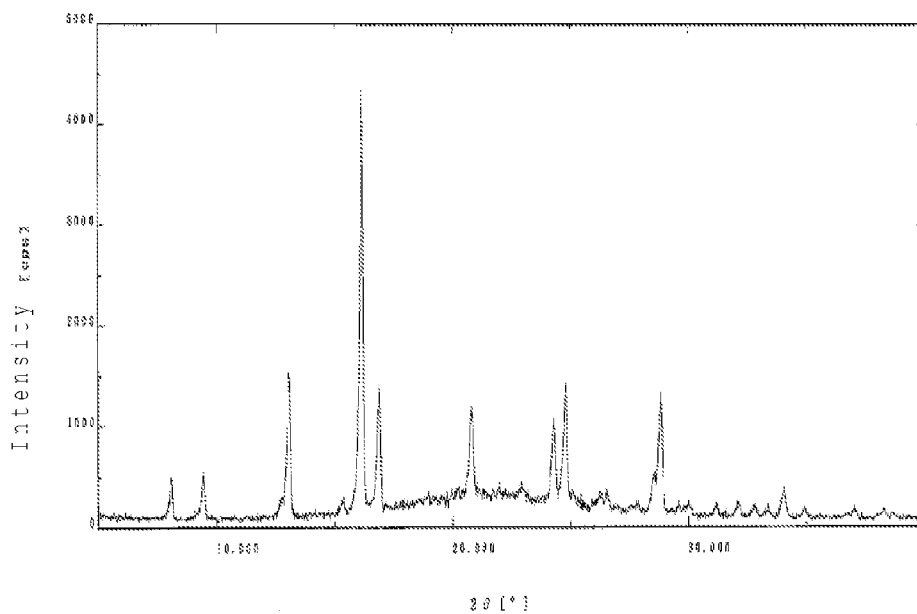
FIG. 20 shows an X-ray powder diffraction pattern of the crystal obtained in Example 17. The longitudinal axis of the pattern (numerical values added to the scale are 0, 1000, 2000, 3000, 4000 and 5000 from the bottom) shows diffraction intensity as a count/sec (cps) unit, and the horizontal axis (numerical values added to the scale are 10.000, 20.000 and 30.000 from the left) shows the value of angle of diffraction 2θ.

An X-ray powder diffraction pattern of the crystal of the monohydrochloride obtained in Example 17, which was measured by the above-described method, is shown in FIG. 20.

Figure 21:
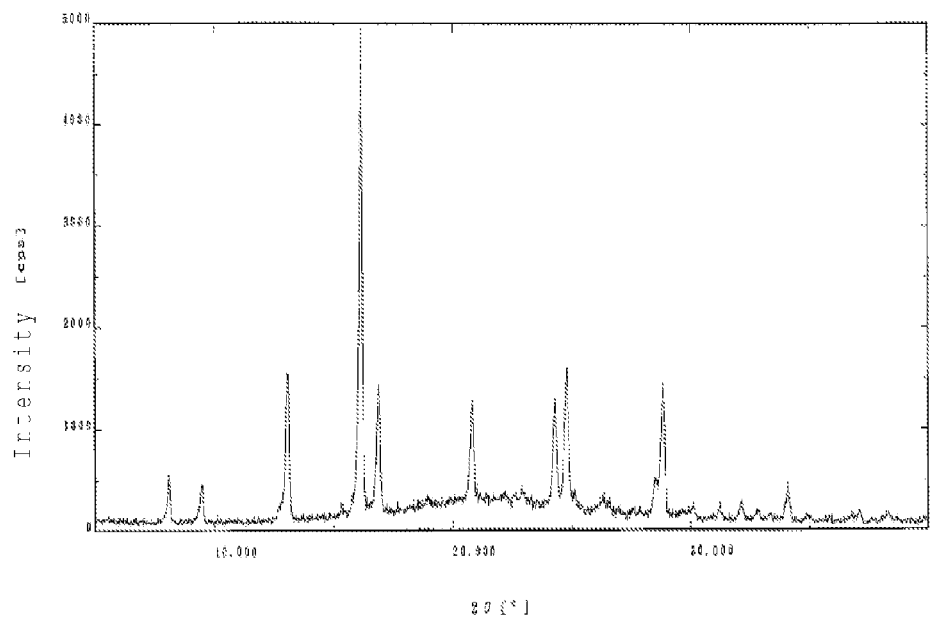
FIG. 21 shows an X-ray powder diffraction pattern of the crystal obtained in Example 18. The longitudinal axis of the pattern (numerical values added to the scale are 0, 1000, 2000, 3000, 4000 and 5000 from the bottom) shows diffraction intensity as a count/sec (cps) unit, and the horizontal axis (numerical values added to the scale are 10.000, 20.000 and 30.000 from the left) shows the value of angle of diffraction 2θ.

An X-ray powder diffraction pattern of the crystal of the monohydrochloride obtained in Example 18, which was measured by the above-described method, is shown in FIG. 21.

Figure 22:
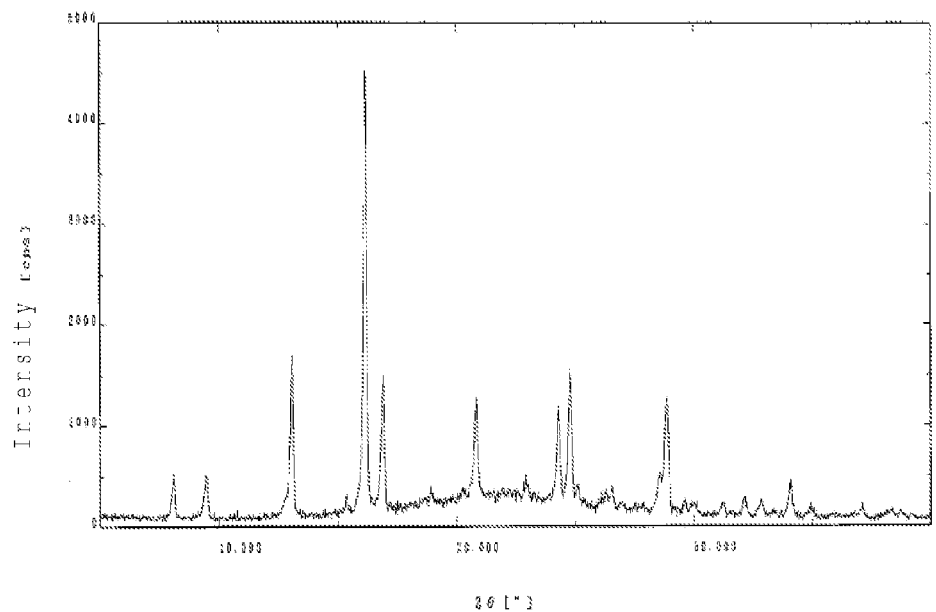
FIG. 22 shows an X-ray powder diffraction pattern of the crystal obtained in Example 19. The longitudinal axis of the pattern (numerical values added to the scale are 0, 1000, 2000, 3000, 4000 and 5000 from the bottom) shows diffraction intensity as a count/sec (cps) unit, and the horizontal axis (numerical values added to the scale are 10.000, 20.000 and 30.000 from the left) shows the value of angle of diffraction 2θ.

An X-ray powder diffraction pattern of the crystal of the monohydrochloride obtained in Example 19, which was measured by the above-described method, is shown in FIG. 22.

Figure 23:
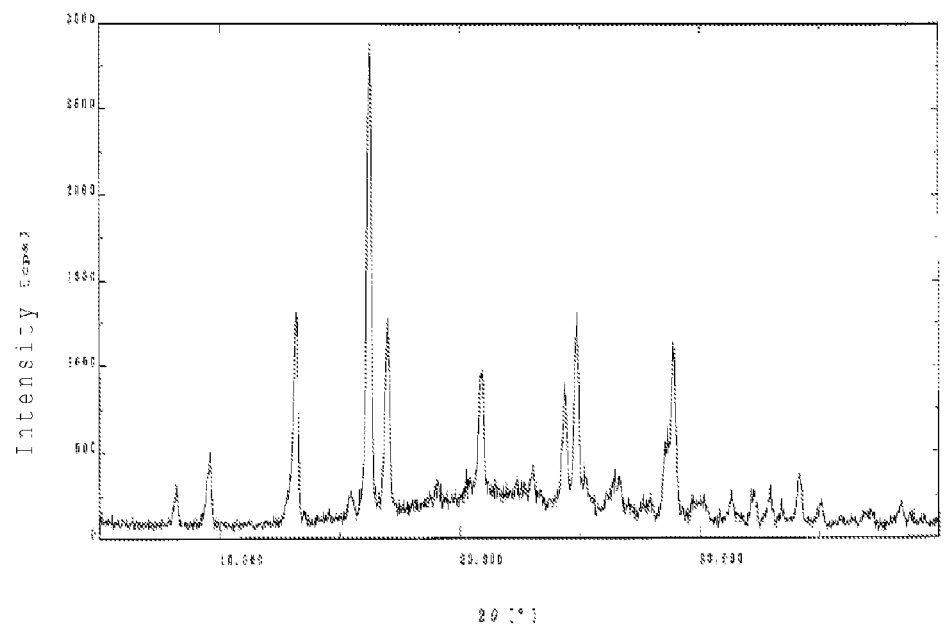
FIG. 23 shows an X-ray powder diffraction pattern of the crystal obtained in Example 20. The longitudinal axis of the pattern (numerical values added to the scale are 0, 500, 1000, 1500, 2000, 2500 and 3000 from the bottom) shows diffraction intensity as a count/sec (cps) unit, and the horizontal axis (numerical values added to the scale are 10.000, 20.000 and 30.000 from the left) shows the value of angle of diffraction 2θ.

An X-ray powder diffraction pattern of the crystal of the monohydrochloride obtained in Example 20, which was measured by the above-described method, is shown in FIG. 23.

Figure 24:
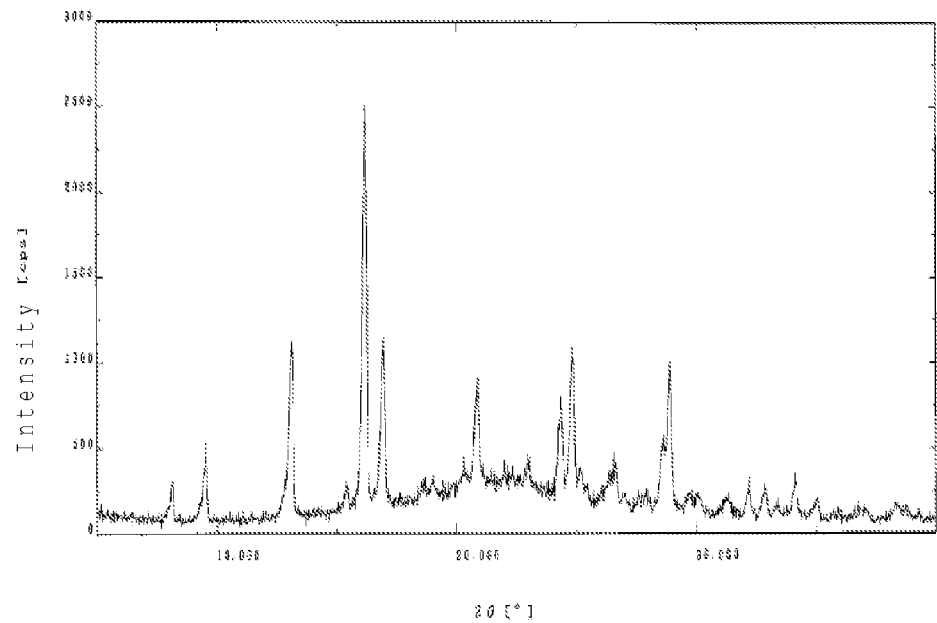
FIG. 24 shows an X-ray powder diffraction pattern of the crystal obtained in Example 21. The longitudinal axis of the pattern (numerical values added to the scale are 0, 500, 1000, 1500, 2000, 2500 and 3000 from the bottom) shows diffraction intensity as a count/sec (cps) unit, and the horizontal axis (numerical values added to the scale are 10.000, 20.000 and 30.000 from the left) shows the value of angle of diffraction 2θ.

An X-ray powder diffraction pattern of the crystal of the monohydrochloride obtained in Example 21, which was measured by the above-described method, is shown in FIG. 24.

Figure 25:
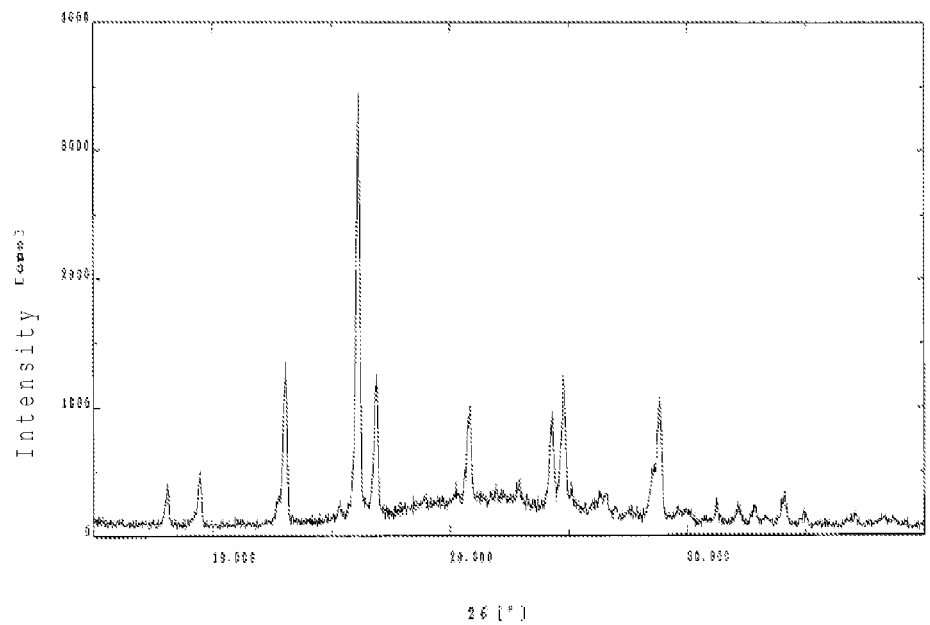
FIG. 25 shows an X-ray powder diffraction pattern of the crystal obtained in Example 22. The longitudinal axis of the pattern (numerical values added to the scale are 0, 1000, 2000, 3000 and 4000 from the bottom) shows diffraction intensity as a count/sec (cps) unit, and the horizontal axis (numerical values added to the scale are 10.000, 20.000 and 30.000 from the left) shows the value of angle of diffraction 2θ.

An X-ray powder diffraction pattern of the crystal of the monohydrochloride obtained in Example 22, which was measured by the above-described method, is shown in FIG. 25.

Figure 26:
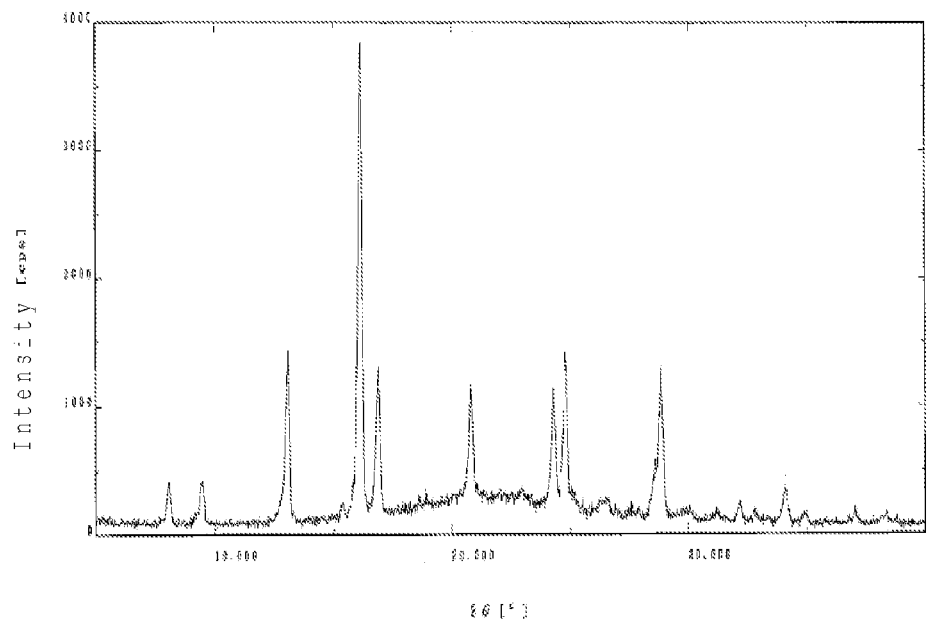
FIG. 26 shows an X-ray powder diffraction pattern of the crystal obtained in Example 23. The longitudinal axis of the pattern (numerical values added to the scale are 0, 1000, 2000, 3000 and 4000 from the bottom) shows diffraction intensity as a count/sec (cps) unit, and the horizontal axis (numerical values added to the scale are 10.000, 20.000 and 30.000 from the left) shows the value of angle of diffraction 2θ.

An X-ray powder diffraction pattern of the crystal of the monohydrochloride obtained in Example 23, which was measured by the above-described method, is shown in FIG. 26.

Figure 27:
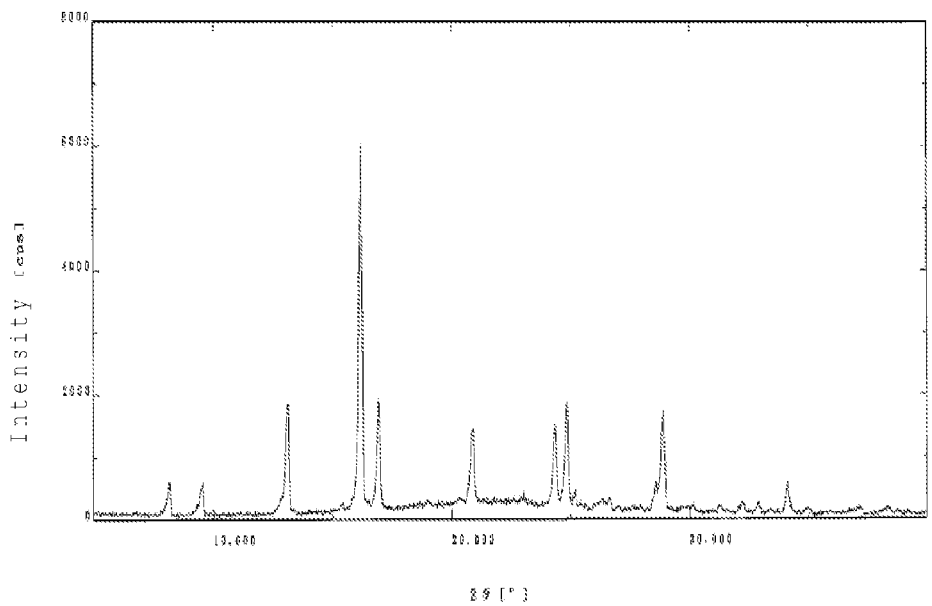
FIG. 27 shows an X-ray powder diffraction pattern of the crystal obtained in Example 24. The longitudinal axis of the pattern (numerical values added to the scale are 0, 2000, 4000, 6000 and 8000 from the bottom) shows diffraction intensity as a count/sec (cps) unit, and the horizontal axis (numerical values added to the scale are 10.000, 20.000 and 30.000 from the left) shows the value of angle of diffraction 2θ.

An X-ray powder diffraction pattern of the crystal of the monohydrochloride obtained in Example 24, which was measured by the above-described method, is shown in FIG. 27.

Figure 28:
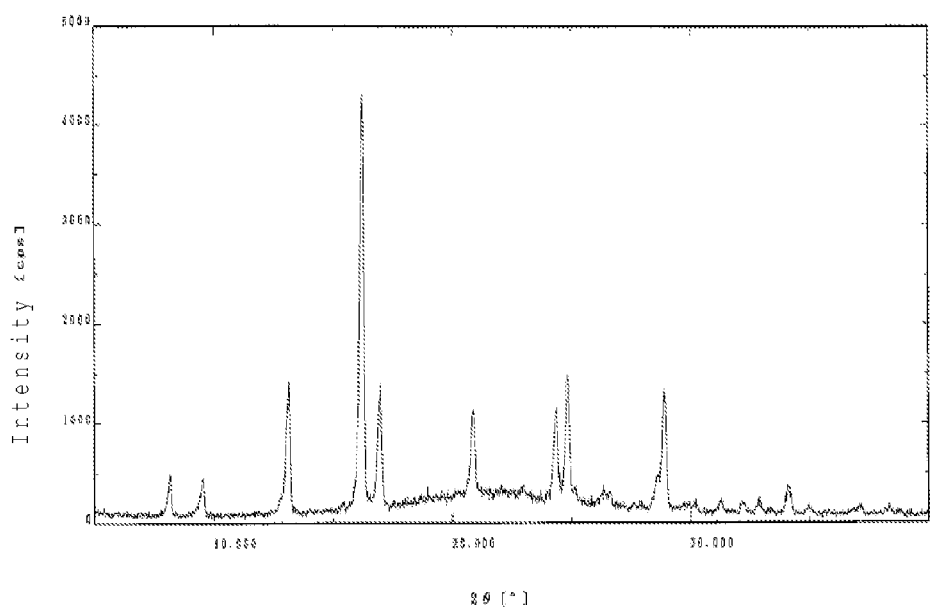
FIG. 28 shows an X-ray powder diffraction pattern of the crystal obtained in Example 25. The longitudinal axis of the pattern (numerical values added to the scale are 0, 1000, 2000, 3000, 4000 and 5000 from the bottom) shows diffraction intensity as a count/sec (cps) unit, and the horizontal axis (numerical values added to the scale are 10.000, 20.000 and 30.000 from the left) shows the value of angle of diffraction 2θ.

An X-ray powder diffraction pattern of the crystal of the monohydrochloride obtained in Example 25, which was measured by the above-described method, is shown in FIG. 28.

Figure 29:
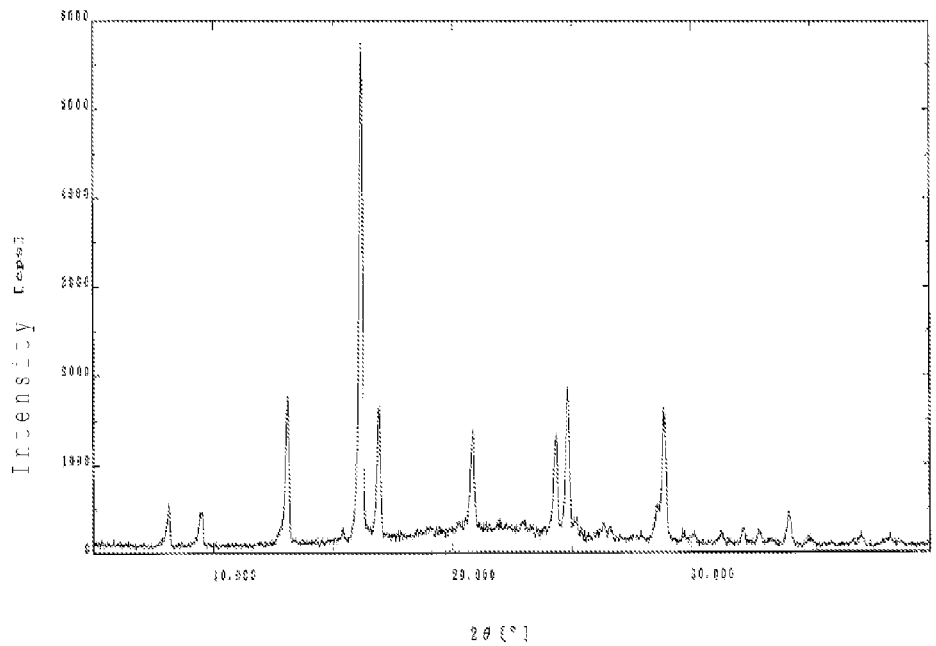
FIG. 29 shows an X-ray powder diffraction pattern of the crystal obtained in Example 26. The longitudinal axis of the pattern (numerical values added to the scale are 0, 1000, 2000, 3000, 4000, 5000 and 6000 from the bottom) shows diffraction intensity as a count/sec (cps) unit, and the horizontal axis (numerical values added to the scale are 10.000, 20.000 and 30.000 from the left) shows the value of angle of diffraction 2θ.

An X-ray powder diffraction pattern of the crystal of the monohydrochloride obtained in Example 26, which was measured by the above-described method, is shown in FIG. 29.

Figure 30:
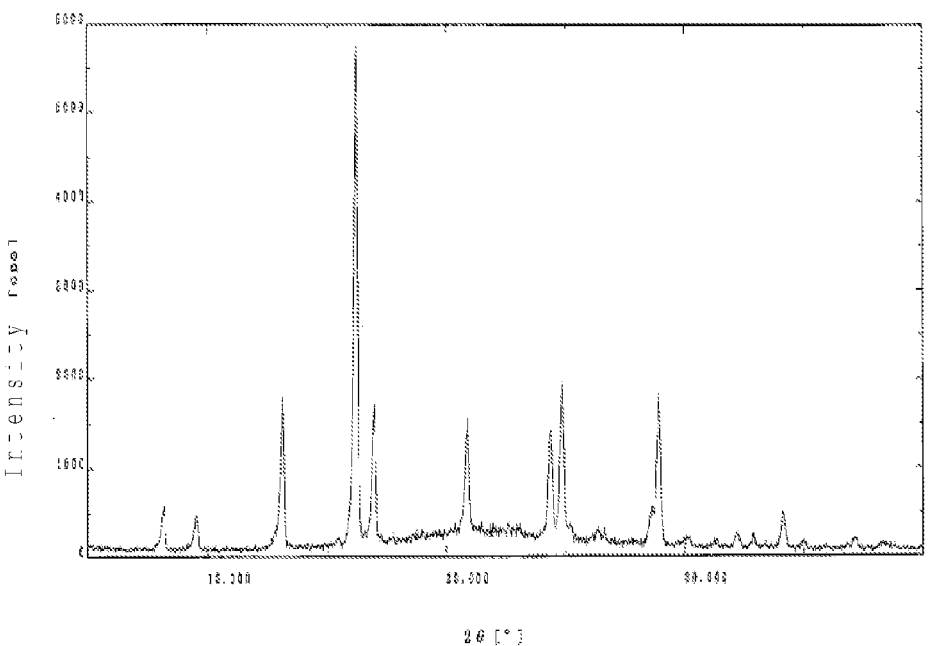
FIG. 30 shows an X-ray powder diffraction pattern of the crystal obtained in Example 27. The longitudinal axis of the pattern (numerical values added to the scale are 0, 1000, 2000, 3000, 4000, 5000 and 6000 from the bottom) shows diffraction intensity as a count/sec (cps) unit, and the horizontal axis (numerical values added to the scale are 10.000, 20.000 and 30.000 from the left) shows the value of angle of diffraction 2θ.

An X-ray powder diffraction pattern of the crystal of the monohydrochloride obtained in Example 27, which was measured by the above-described method, is shown in FIG. 30.

Figure 31:
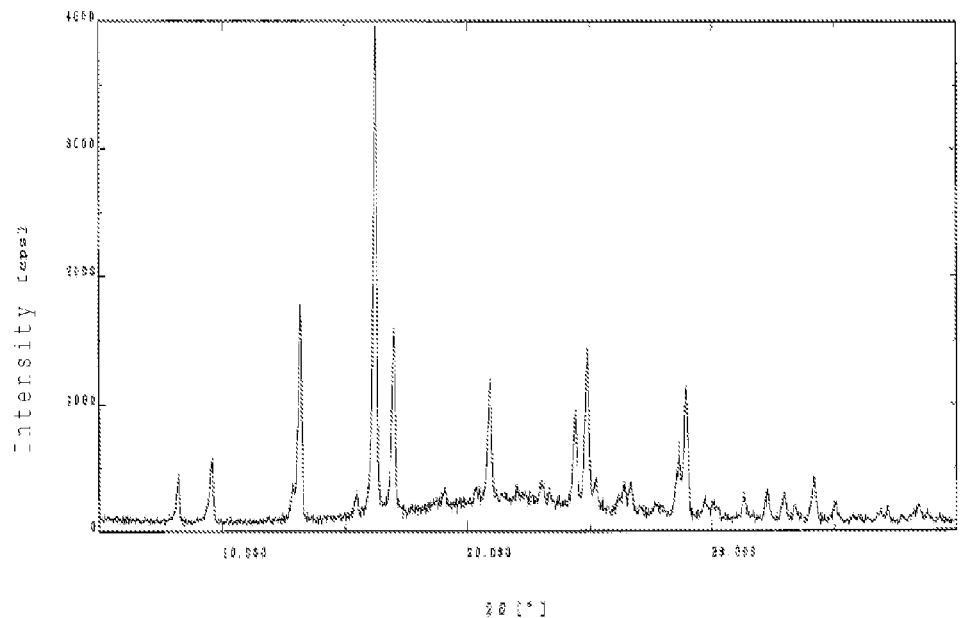
FIG. 31 shows an X-ray powder diffraction pattern of the crystal obtained in Example 28. The longitudinal axis of the pattern (numerical values added to the scale are 0, 1000, 2000, 3000 and 4000 from the bottom) shows diffraction intensity as a count/sec (cps) unit, and the horizontal axis (numerical values added to the scale are 10.000, 20.000 and 30.000 from the left) shows the value of angle of diffraction 2θ.

An X-ray powder diffraction pattern of the crystal of the monohydrochloride obtained in Example 28, which was measured by the above-described method, is shown in FIG. 31.

Figure 32:
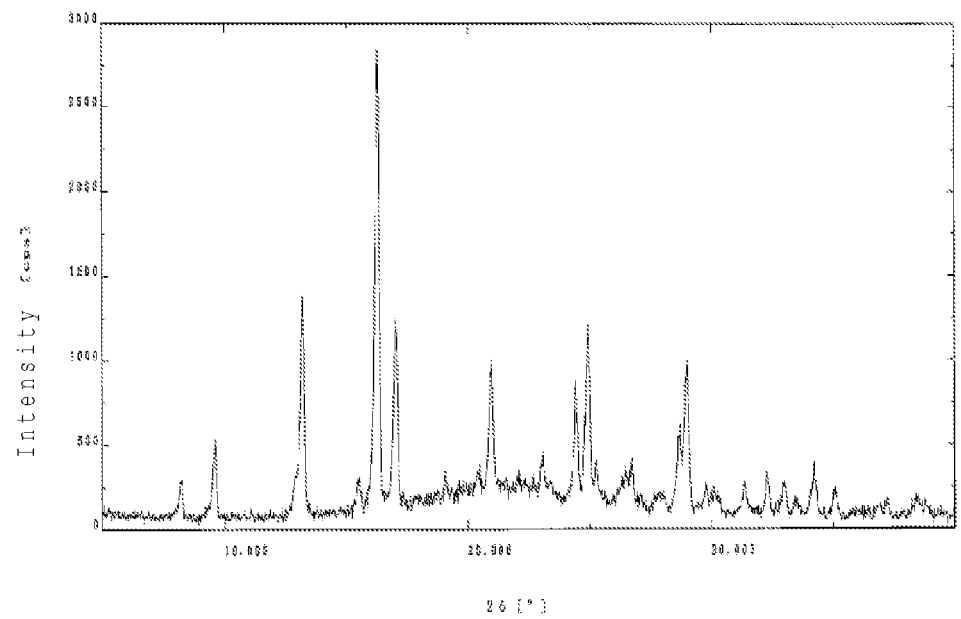
FIG. 32 shows an X-ray powder diffraction pattern of the crystal obtained in Example 29. The longitudinal axis of the pattern (numerical values added to the scale are 0, 500, 1000, 1500, 2000, 2500 and 3000 from the bottom) shows diffraction intensity as a count/sec (cps) unit, and the horizontal axis (numerical values added to the scale are 10.000, 20.000 and 30.000 from the left) shows the value of angle of diffraction 2θ.

An X-ray powder diffraction pattern of the crystal of the monohydrochloride obtained in Example 29, which was measured by the above-described method, is shown in FIG. 32.

Figure 33:
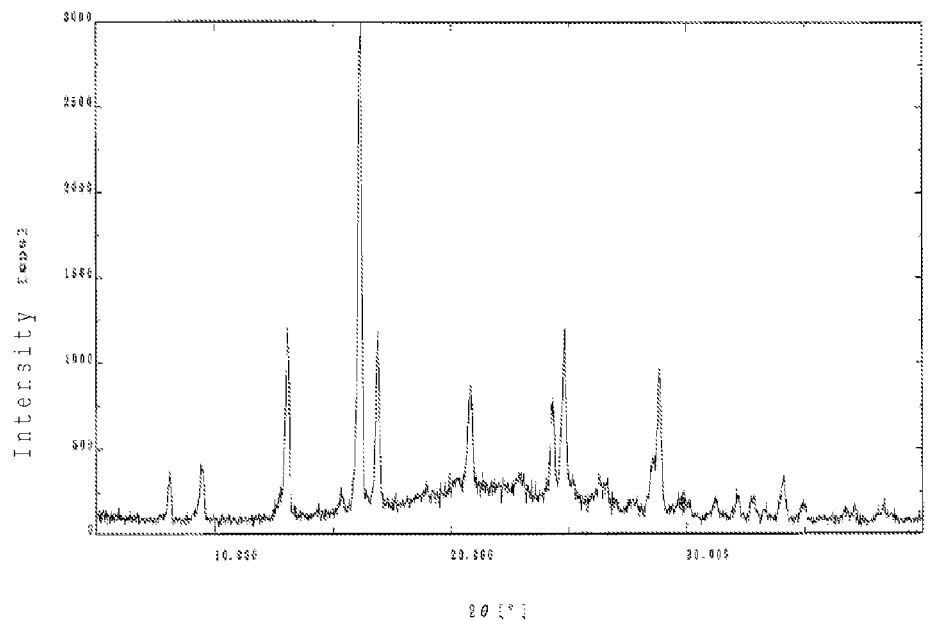
FIG. 33 shows an X-ray powder diffraction pattern of the crystal obtained in Example 30. The longitudinal axis of the pattern (numerical values added to the scale are 0, 500, 1000, 1500, 2000, 2500 and 3000 from the bottom) shows diffraction intensity as a count/sec (cps) unit, and the horizontal axis (numerical values added to the scale are 10.000, 20.000 and 30.000 from the left) shows the value of angle of diffraction 2θ.

An X-ray powder diffraction pattern of the crystal of the monohydrochloride obtained in Example 30, which was measured by the above-described method, is shown in FIG. 33.

Figure 34:
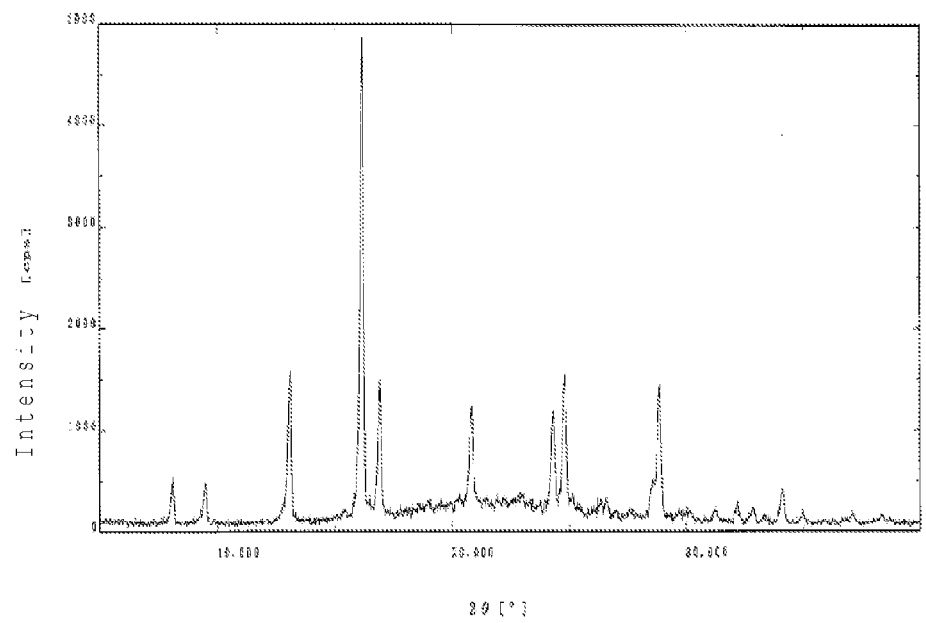
FIG. 34 shows an X-ray powder diffraction pattern of the crystal obtained in Example 31. The longitudinal axis of the pattern (numerical values added to the scale are 0, 1000, 2000, 3000, 4000 and 5000 from the bottom) shows diffraction intensity as a count/sec (cps) unit, and the horizontal axis (numerical values added to the scale are 10.000, 20.000 and 30.000 from the left) shows the value of angle of diffraction 2θ.

An X-ray powder diffraction pattern of the crystal of the monohydrochloride obtained in Example 31, which was measured by the above-described method, is shown in FIG. 34.

Figure 35:
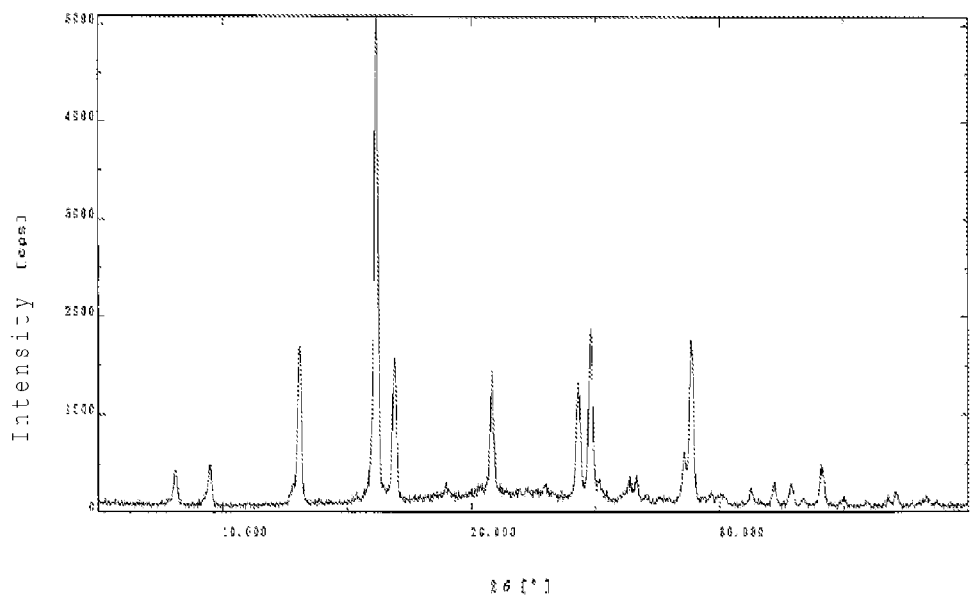
FIG. 35 shows an X-ray powder diffraction pattern of the crystal obtained in Example 32. The longitudinal axis of the pattern (numerical values added to the scale are 0, 1000, 2000, 3000, 4000 and 5000 from the bottom) shows diffraction intensity as a count/sec (cps) unit, and the horizontal axis (numerical values added to the scale are 10.000, 20.000 and 30.000 from the left) shows the value of angle of diffraction 2θ.

An X-ray powder diffraction pattern of the crystal of the monohydrochloride obtained in Example 32, which was measured by the above-described method, is shown in FIG. 35.

Figure 36:
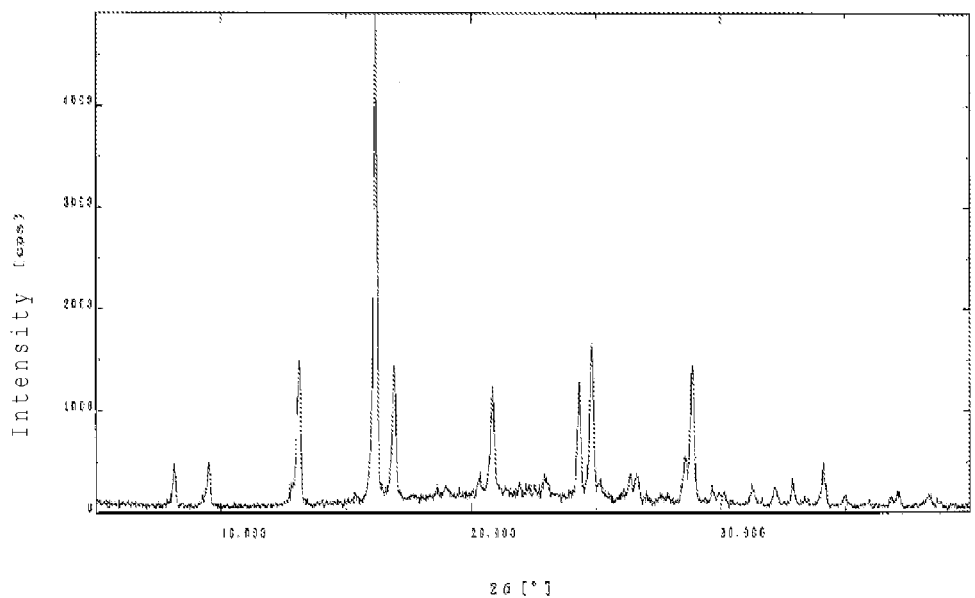
FIG. 36 shows an X-ray powder diffraction pattern of the crystal obtained in Example 33. The longitudinal axis of the pattern (numerical values added to the scale are 0, 1000, 2000, 3000 and 4000 from the bottom) shows diffraction intensity as a count/sec (cps) unit, and the horizontal axis (numerical values added to the scale are 10.000, 20.000 and 30.000 from the left) shows the value of angle of diffraction 2θ.

An X-ray powder diffraction pattern of the crystal of the monohydrochloride obtained in Example 33, which was measured by the above-described method, is shown in FIG. 36.

Example 36

Figure 37:
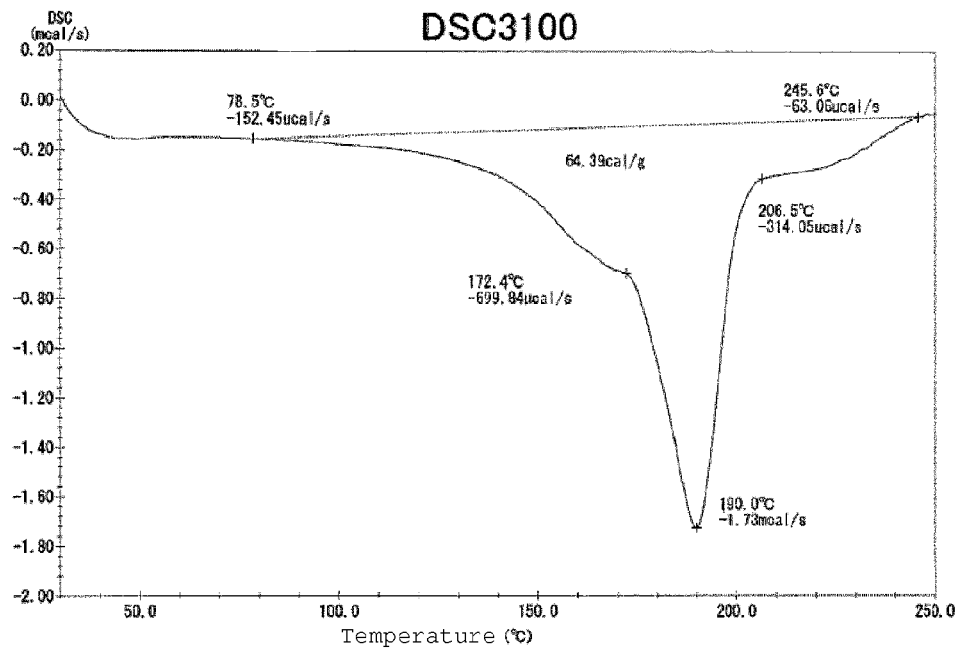
FIG. 37 shows a differential scanning calorimetry pattern of the crystal obtained in Example 1. The longitudinal axis of the pattern shows differential scanning calorie (DSC) (mcal/s), and the horizontal axis shows temperature (° C.).

Differential Scanning Calorimetry
<Measurement Method>
A differential scanning calorimeter (model: DSC3100, manufactured by Mac Science) was used. 5 mg of the hydrochloride of 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide was weighed into a measuring pan made of aluminum, and measurement was then carried out by increasing the temperature of the pan from room temperature to 250° C. at a temperature increasing rate of 10° C./min, while the pan was in an opened state.
<Measurement Results>
A differential scanning calorimetry pattern, which was obtained by measuring the crystal of the dihydrochloride obtained in Example 1 according to the above-described method, is shown in FIG. 37.

Figure 38:
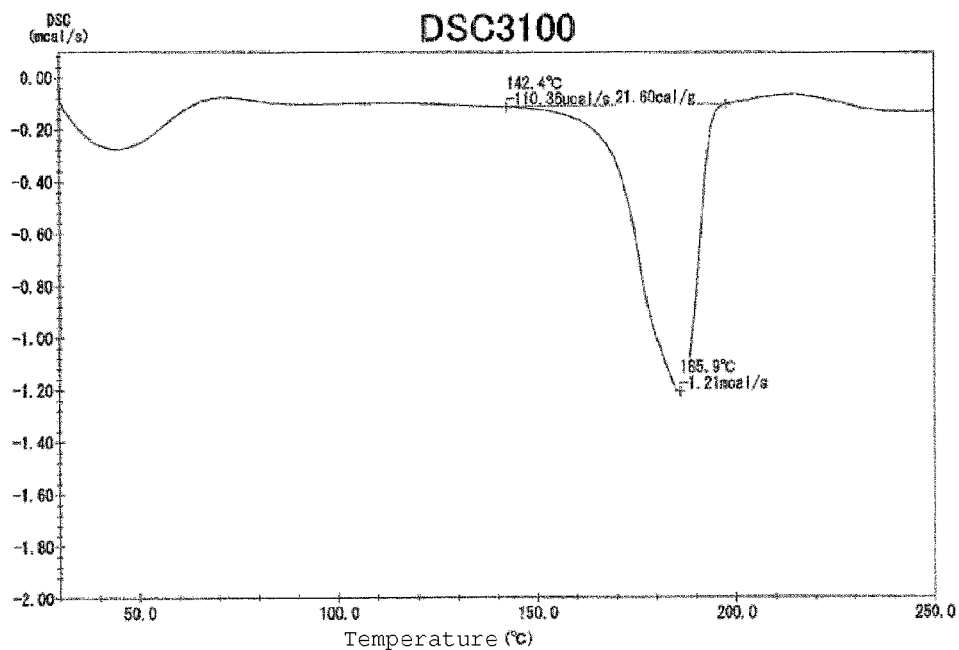
FIG. 38 shows a differential scanning calorimetry pattern of the crystal obtained in Example 4. The longitudinal axis of the pattern shows differential scanning calorie (DSC) (mcal/s), and the horizontal axis shows temperature (° C.).

A differential scanning calorimetry pattern, which was obtained by measuring the crystal of the monohydrochloride obtained in Example 4 according to the above-described method, is shown in FIG. 38.

Figure 39:
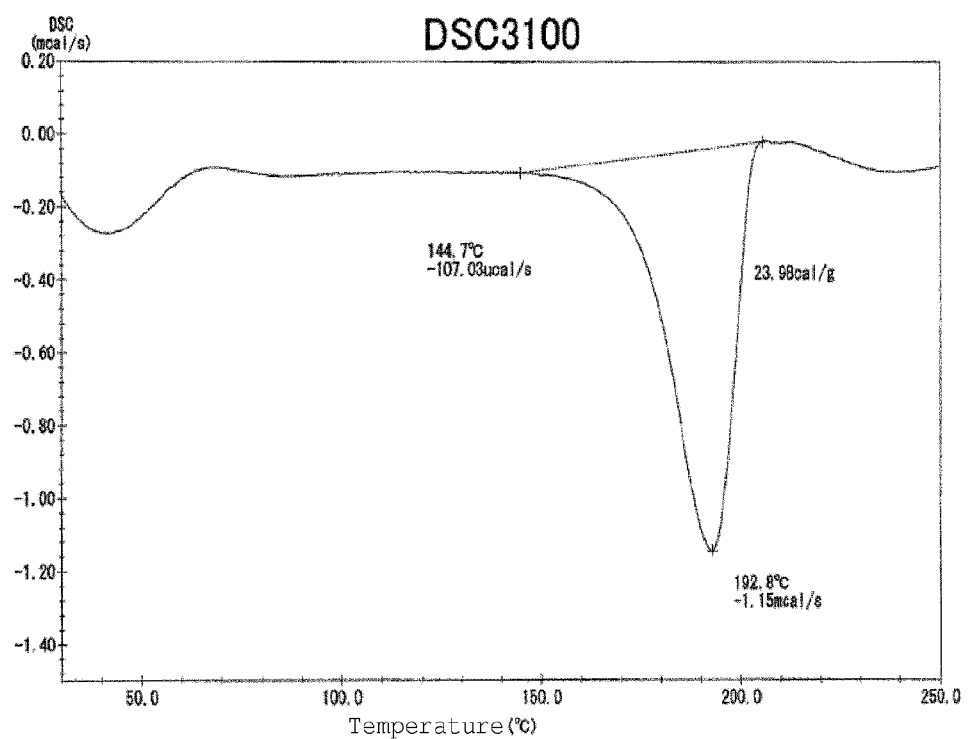
FIG. 39 shows a differential scanning calorimetry pattern of the crystal obtained in Example 11. The longitudinal axis of the pattern shows differential scanning calorie (DSC) (mcal/s), and the horizontal axis shows temperature (° C.).

A differential scanning calorimetry pattern, which was obtained by measuring the crystal of the monohydrochloride obtained in Example 11 according to the above-described method, is shown in FIG. 39.

Example 37

Analysis of Residual Ethanol
Residual ethanol was analyzed by gas chromatography as described below.
<Preparation of Standard Solution>
1) 500 mg of ethanol (=$W_{EtOH}$ [mg]) was precisely weighed, and dimethyl sulfoxide was then added to the ethanol, so as to precisely prepare a solution with a total amount of 20 ml. The obtained solution was defined as solution [1].
2) 4 mL of the solution [1] was precisely weighed, and dimethyl sulfoxide was then added to the solution [1], so as to precisely prepare a solution with a total amount of 20 ml. The obtained solution was defined as solution [2].
3) 4 mL of the solution [2] was precisely weighed, and dimethyl sulfoxide was then added to the solution [2], so as to precisely prepare a solution with a total amount of 20 ml. The obtained solution was defined as solution [3] (ethanol concentration=$W_{EtOH}/500$ [mg/ml]).
4) 2 mL of the solution [2] was precisely weighed, and dimethyl sulfoxide was then added to the solution [2], so as to precisely prepare a solution with a total amount of 20 ml. The obtained solution was defined as solution [4] (ethanol concentration=$W_{EtOH}/1000$ [mg/ml]).
5) 2 mL of the solution [4] was precisely weighed, and dimethyl sulfoxide was then added to the solution [4], so as to precisely prepare a solution with a total amount of 20 ml. The obtained solution was defined as solution [5] (ethanol concentration=$W_{EtOH}/10000$ [mg/ml]).
<Preparation of Sample Solution>
50 mg of 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide monohydrochloride or 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide dihydrochloride (=$W_{sample}$ [mg]) was precisely weighed. The thus obtained sample was dissolved in 1 ml of dimethyl sulfoxide, and the obtained solution was used as a sample solution.
<Analysis Conditions>
Detector: flame ionization detector
Column: DB-624 (0.32 mmID×30 m, film thickness: 1.8 μm, manufactured by Agilent)
Column temperature: The temperature of the column was retained at 40° C. for 5 minutes, and thereafter, the temperature was increased to 220° C. at a temperature increasing rate of 15° C./min. The temperature was retained at 220° C. for 3 minutes.
Injection port temperature: 200° C.
Detector temperature: 240° C.
Carrier gas: Helium
Column flow rate: 70 kpa
Split ratio: 1:20
Injection amount: 1 μL
<Measurement and Calculation>
1) 1 μL of the solution [3] was injected into the column so as to obtain the peak area of ethanol (=$A_{EtOH[3]}$).
2) 1 μL of the solution [4] was injected into the column so as to obtain the peak area of ethanol (=$A_{EtOH[4]}$).
3) 1 μL of the solution [5] was injected into the column so as to obtain the peak area of ethanol (=$A_{EtOH[5]}$).
4) The ethanol concentration was defined as y, and the ethanol peak area was defined as x. Based on the numerical values of the solution [3] (x=$A_{EtOH[3]}$, y=$W_{EtOH}/500$), the solution [4] (x=$A_{EtOH[4]}$, y=$W_{EtOH}/1000$), and the solution [5] (x=$A_{EtOH[5]}$, y=$W_{EtOH}/10000$), a regression equation of a linear function was produced.
5) 1 μL of the sample solution was injected into the column so as to obtain the peak area of ethanol (=$A_{sample}$). The obtained value was substituted into x in the above regression equation, so as to obtain the ethanol concentration of the sample solution (=$C_{sample}$ [mg/ml]) as y.
6) The amount of residual ethanol was calculated using the equation: [ppm]=1000000×$C_{sample}$ [mg/ml]×1 [ml]÷$W_{sample}$ [mg].
<Measurement Results>
The amount of residual ethanol in individual crystals obtained in Examples 1, 4, 7, 8, 9, 10, 11, 12, 13, 14, 15, 16, 17, 18, 19, 20, 21, 22, 23, 24, 25, 26, 27, 28, 29, 30, 31, 32 and 33 was measured by the above-described method. The results are shown in Table 4.

TABLE 4

| Example No. | Salt form | Amount of residual ethanol (ppm) |
|---|---|---|
| Example 1 | Dihydrochloride | 6150 |
| Example 4 | Monohydrochloride | 10980 |
| Example 7 | Monohydrochloride | 4730 |
| Example 8 | Monohydrochloride | 4790 |
| Example 9 | Monohydrochloride | 3830 |
| Example 10 | Monohydrochloride | 2060 |
| Example 11 | Monohydrochloride | 1910 |
| Example 12 | Monohydrochloride | 2150 |
| Example 13 | Monohydrochloride | 2120 |
| Example 14 | Monohydrochloride | 2420 |
| Example 15 | Monohydrochloride | 3620 |
| Example 16 | Monohydrochloride | 2550 |
| Example 17 | Monohydrochloride | 2430 |
| Example 18 | Monohydrochloride | 2520 |
| Example 19 | Monohydrochloride | 2990 |
| Example 20 | Monohydrochloride | 3480 |
| Example 21 | Monohydrochloride | 3680 |
| Example 22 | Monohydrochloride | 2370 |
| Example 23 | Monohydrochloride | 2670 |
| Example 24 | Monohydrochloride | 2650 |
| Example 25 | Monohydrochloride | 2360 |
| Example 26 | Monohydrochloride | 2460 |
| Example 27 | Monohydrochloride | 2380 |
| Example 28 | Monohydrochloride | 3190 |
| Example 29 | Monohydrochloride | 3140 |
| Example 30 | Monohydrochloride | 3010 |
| Example 31 | Monohydrochloride | 2820 |
| Example 32 | Monohydrochloride | 2465 |
| Example 33 | Monohydrochloride | 2064 |

Example 38

Purity Test and Stability Test
<Conditions for Accelerated Test>
Condition 1: 40° C., humidity: 75%
Condition 2: 60° C. (without humidity control)

Samples under the aforementioned accelerated test conditions were measured by high performance liquid chromatography as described below.
<Preparation of 20 mM Potassium Dihydrogen Phosphate Aqueous Solution>
2.72 g of potassium dihydrogen phosphate was dissolved in 1000 ml of water to prepare a 20 mM potassium dihydrogen phosphate aqueous solution.
<Preparation of 20 mM Dibasic Potassium Phosphate Aqueous Solution>
3.48 g of dibasic potassium phosphate was dissolved in 1000 ml of water to prepare a 20 mM dibasic potassium phosphate aqueous solution.
<Preparation of 20 mM Potassium Phosphate Buffer (pH=6.5)>
A 20 mM dibasic potassium phosphate aqueous solution was added to a 20 mM potassium dihydrogen phosphate aqueous solution, so that the pH of the mixed solution was adjusted to pH 6.5. The thus prepared solution was defined as a 20 mM potassium phosphate buffer (pH=6.5).
<Preparation of 20 mM Potassium Phosphate Buffer (pH=7.0)>
A 20 mM dibasic potassium phosphate aqueous solution was added to a 20 mM potassium dihydrogen phosphate aqueous solution, so that the pH of the mixed solution was adjusted to pH 7.0. The thus prepared solution was defined as a 20 mM potassium phosphate buffer (pH=7.0).
<Mobile Phase>
Mobile Phase A: 20 mM potassium phosphate buffer (pH=6.5)/acetonitrile=9/1 (v/v)
Mobile Phase B: 20 mM potassium phosphate buffer (pH=6.5)/acetonitrile=3/7 (v/v)

<Sample-Dissolved Solution>
A sample-dissolved solution was prepared from 20 mM potassium phosphate buffer (pH=7.0)/acetonitrile=3/7.
<Preparation of Sample Solution>
An analyte for the accelerated test was dissolved in the sample-dissolved solution to prepare an approximately 0.5 g/L solution.
<Analysis Conditions>
Column: YMC-Pack Pro C18RS, 3.0 mm ID×150 mm, particle diameter: 3 μm
Column temperature: approximately 40° C.
Gradient conditions:
  0 to 5 minutes, mobile phase A: 100→75/mobile phase B: 0→25
  5 to 15 minutes, mobile phase A: 75/mobile phase B: 25
  15 to 45 minutes, mobile phase A: 75→0/mobile phase B: 25→100
  45 to 55 minutes, mobile phase A: 0/mobile phase B: 100
Flow rate: 0.7 ml/min
Measurement range: 0 to 55 minutes
Detection wavelength: 240 nm
Amount of sample solution injected: 5 μl
<Calculation>
1) The sample solution was injected into the column, so as to obtain the peak area (A) of each related substance and the peak area (T) of compound (1).
2) The sample-dissolved solution was injected into the column, so as to obtain the peak area (B) of each blank.
3) The amount [%] of each related substance was calculated using the formula:

The amount [%] of each related substance=100×(A−B)÷T

<Measurement Results>
The results of the accelerated tests performed on the crystal of the monohydrochloride obtained in Example 4, the crystal of the monohydrochloride obtained in Example 12, and the crystal of the monohydrochloride obtained in Example 28, are shown in Table 5.

TABLE 5

| Sample crystal (Example No.) | Impurity (rrt*) | Purity test (Initial) | Accelerated condition 1 2 weeks | Accelerated condition 1 4 weeks | Accelerated condition 2 2 weeks | Accelerated condition 2 4 weeks |
|---|---|---|---|---|---|---|
| Example 4 | 0.43(%) | 0.75 | 0.94 | 1.04 | 1.09 | 1.21 |
| | Total of unspecified (%) | 1.64 | 1.83 | 2.08 | 2.31 | 2.42 |
| Example 12 | 0.43(%) | 0.27 | 0.30 | 0.33 | 0.32 | 0.33 |
| | Total of unspecified (%) | 1.00 | 1.08 | 1.09 | 1.20 | 1.20 |
| Example 28 | 0.43(%) | 0.37 | 0.41 | 0.44 | 0.44 | 0.45 |
| | Total of unspecified (%) | 1.07 | 1.14 | 1.12 | 1.25 | 1.18 |

*rrt indicates the relative retention time of the impurity, when the retention time of compound (1) is set at 1.

Test Example 1

Cell Growth Inhibition Assay

A cell growth inhibition assay was performed using two types of cells (human breast cancer cell line SK-BR-3 and human lung cancer cell line NCI-H460).

Cells of each type were suspended in a medium and seeded into a 96-well multi-well plate at 2000 cells/150 μL/well in the case of SK-BR-3 and at 500 cells/150 μL/well in the case of NCI-H460. Compound (1) was dissolved in DMSO, and this was diluted with medium to prepare a sample solution (DMSO concentration: 0.5% or less). On the day following the seeding, 50 μL of DMSO-containing medium to which the test compound was not added (hereinafter called DMSO diluted solution; DMSO concentration: 0.5% or less) or 50 μL of the sample solution was further added to the cells. An MTT assay was performed immediately after and 72 hours after adding the sample solution or the DMSO diluted solution to the cells. The MTT assay was performed as follows.

5 mg/mL of an MTT (3-(4,5-dimethylthiazol-2-yl)-2,5-diphenyltetrazolium bromide) solution was added at 20 μL per well. Thereafter, the plate was incubated at 37° C. in 5% $CO_2$ for four hours. The plate was centrifuged at 1200 rpm for five minutes, and then the culture supernatant was removed by suction using a dispenser. DMSO was added at 150 μL per well, and the generated formazan was dissolved. The plate was stirred using a plate mixer to uniformly color the respective wells. The absorbance of each well was measured using a plate reader at an OD of 540 nm with a reference of 660 nm.

T/C (%) for each concentration was determined by the following calculation formula and a dose-response curve was drawn to calculate the 50% growth inhibitory concentration ($GI_{50}$ value), based on the assumption that the OD value measured immediately after adding the sample solution was S, the OD value measured 72 hours after adding the sample solution was T, and the OD value measured 72 hours after adding the DMSO diluted solution was C.

$$T/C(\%) = (T-S)/(C-S) \times 100$$

Compound (1) exhibited a $GI_{50}$ value of 13 (nM) with respect to SK-BR-3 cells, and a $GI_{50}$ value of 26 (nM) with respect to NCI-H460 cells.

Formulation Example 1

Capsule 5 g of the crystal obtained in Example 2, 3 or 6, 115 g of lactose, 58 g of corn starch, and 2 g of magnesium stearate were mixed using a V-shape rotating mixer, and the obtained mixture was then filled in an amount of 180 mg each into capsule No. 3, so as to obtain a capsule.

Formulation Example 2

Tablet 5 g of the crystal obtained in Example 2, 3 or 6, 90 g of lactose, 34 g of corn starch, 20 g of crystalline cellulose, and 1 g of magnesium stearate were mixed using a V-shape rotating mixer, and the obtained mixture was then subjected to a tablet-making machine at a mass of 150 mg per tablet, so as to obtain a tablet.

Formulation Example 3

Suspension

Methyl cellulose was dispersed and dissolved in purified water to prepare a dispersion medium. The crystal obtained in Example 2, 3 or 6 was weighed in a mortar. The aforementioned dispersion medium was added by small amounts thereto, while they were fully blended. Purified water was added to the mixture to prepare 100 g of a suspension.

The invention claimed is:
1. A hydrochloride of 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide represented by formula (1):

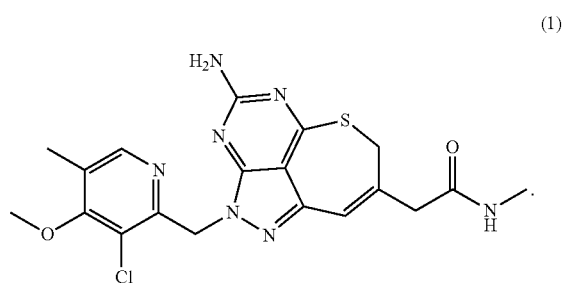

(1)

2. A crystal of a dihydrochloride of 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide represented by formula (1) according to claim 1.

3. A crystal according to claim 2 which has the X-ray diffraction pattern shown in FIG. 1, in an X-ray powder diffraction pattern obtained by irradiation with copper Kα radiation (wavelength λ=1.54 angstroms).

4. A crystal according to claim 2 which shows characteristic peaks at angles of diffraction 2θ of 7.73, 24.70, 26.01 and 27.29, in an X-ray powder diffraction pattern obtained by irradiation with copper Kα radiation (wavelength λ=1.54 angstroms).

5. A crystal according to claim 2 which shows principal peaks at angles of diffraction 2θ of 7.73, 9.78, 12.58, 14.36, 15.84, 16.71, 17.17, 18.40, 19.58, 21.31, 22.85, 23.62, 24.13, 24.70, 26.01, 27.29, 28.58, 29.37, 30.65, 31.38, 33.52, 35.25 and 36.87, in an X-ray powder diffraction pattern obtained by irradiation with copper Kα radiation (wavelength λ=1.54 angstroms).

6. A crystal of a monohydrochloride of 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide represented by formula (1) according to claim 1.

7. A crystal according to claim 6 which has the X-ray diffraction pattern shown in FIG. 2, in an X-ray powder diffraction pattern obtained by irradiation with copper Kα radiation (wavelength λ=1.54 angstroms).

8. A crystal according to claim 6 which shows principal peaks at angles of diffraction 2θ of 9.43, 12.70, 13.03, 15.33, 16.10, 16.84, 18.55, 20.21, 20.89, 21.32, 22.93, 24.73, 25.10, 25.40, 26.10, 26.53, 26.95, 27.60, 27.88, 28.52, 29.63, 29.95, 31.55, 32.13, 33.40, 34.95 and 38.70, in an X-ray powder diffraction pattern obtained by irradiation with copper Kα radiation (wavelength λ=1.54 angstroms).

9. A crystal according to claim 6 which has the X-ray diffraction pattern shown in FIG. 3, in an X-ray powder diffraction pattern obtained by irradiation with copper Kα radiation (wavelength λ=1.54 angstroms).

10. A crystal according to claim 6 which shows principal peaks at angles of diffraction 2θ of 8.07, 9.45, 13.07, 15.39, 16.16, 16.90, 20.83, 24.29, 24.80, 28.56, 28.85, 31.26, 32.17, 32.87 and 34.11, in an X-ray powder diffraction pattern obtained by irradiation with copper Kα radiation (wavelength λ=1.54 angstroms).

11. A crystal of a hydrochloride of 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide represented by formula (1) according to claim 1 having an ethanol content that is 5000 ppm or less.

12. A crystal according to claim 11, wherein the hydrochloride is a monohydrochloride.

13. A method for producing a hydrochloride which comprises adding a hydrogen chloride solution dropwise to a solution or suspension of 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide represented by formula (1) according to claim 1.

14. A method for producing a crystal of a dihydrochloride which comprises adding a hydrogen chloride solution dropwise to a solution or suspension of 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide represented by formula (1) according to claim 1 in an amount of 2 equivalents or more relative to the N-methylacetamide.

15. A method for producing a crystal of a monohydrochloride which comprises adding a hydrogen chloride solution dropwise to a solution or suspension of 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide represented by formula (1) according to claim 1 in an amount of 1 equivalent or more to 5 equivalents or less relative to the N-methylacetamide represented by formula (1).

16. A pharmaceutical composition comprising a crystal according to claim 2 and a pharmacologically acceptable carrier.

17. A pharmaceutical composition comprising a crystal according to claim 6 and a pharmacologically acceptable carrier.

* * * * *